United States Patent
Steinberg

(10) Patent No.: US 7,803,193 B2
(45) Date of Patent: Sep. 28, 2010

(54) KNEE PROSTHESIS HAVING A DEFORMABLE ARTICULATION SURFACE

(75) Inventor: Amiram Steinberg, Avihail (IL)

(73) Assignee: Active Implants Corporation, Memphis, TN (US)

( * ) Notice: Subject to any disclaimer, the term of this patent is extended or adjusted under 35 U.S.C. 154(b) by 1435 days.

(21) Appl. No.: 11/003,197

(22) Filed: Dec. 3, 2004

(65) Prior Publication Data

US 2005/0149199 A1     Jul. 7, 2005

Related U.S. Application Data

(63) Continuation of application No. 10/289,126, filed on Nov. 5, 2002, and a continuation of application No. 09/902,701, filed on Sep. 5, 2001, now abandoned, and a continuation of application No. 09/043,076, filed on Feb. 2, 1999, now abandoned.

(51) Int. Cl.
    *A61F 2/38*      (2006.01)
(52) U.S. Cl. ................. 623/20.21; 623/20.14
(58) Field of Classification Search .............. 623/20.14, 623/20.21, 20.27, 20.28, 20.31, 20.32, 20.34; 606/88

See application file for complete search history.

(56) References Cited

U.S. PATENT DOCUMENTS

| | | | |
|---|---|---|---|
| 2,765,787 A | 9/1954 | Pellet | |
| 3,875,594 A | 4/1975 | Swanson | |
| 3,916,451 A | 11/1975 | Buechel et al. | |
| 3,938,198 A | 2/1976 | Kahn et al. | |
| 3,992,726 A | 11/1976 | Freeman | |
| 4,031,570 A | 6/1977 | Frey | |
| 4,279,041 A | 7/1981 | Buholtz | |
| 4,292,695 A | 10/1981 | Koeneman | |
| 4,314,381 A | 2/1982 | Koeneman | |
| 4,327,449 A | 5/1982 | Charnley | |
| 4,344,193 A | 8/1982 | Kenny | |
| 4,470,158 A * | 9/1984 | Pappas et al. | 623/20.21 |
| 4,570,270 A | 2/1986 | Oechsle, III | |
| 4,624,674 A | 11/1986 | Pappas et al. | |

(Continued)

FOREIGN PATENT DOCUMENTS

CH            426096            12/1966

(Continued)

OTHER PUBLICATIONS

U.S. Appl. No. 09/043,076, filed Mar. 4, 1998, Steinberg, Amiram, Abandoned.

(Continued)

*Primary Examiner*—Brian E. Pellegrino
(74) *Attorney, Agent, or Firm*—Haynes and Boone LLP

(57) ABSTRACT

Knee prostheses are provided. In some embodiments, the knee prostheses include a body formed of a resilient polyurethane having contact surface area that changes during use according to physical loading factors. In some embodiments, the knee prostheses include a femoral component configured for secure engagement with a lower portion of a femur without penetrating the femur and a tibial component configured for secure engagement with an upper portion of a tibia without penetrating the tibia. In that regard, the tibial component is also configured for moving engagement with the femoral component in some instances.

13 Claims, 41 Drawing Sheets

U.S. PATENT DOCUMENTS

| | | | |
|---|---|---|---|
| 4,650,491 A | 3/1987 | Parchinski | |
| 4,655,778 A | 4/1987 | Koeneman | |
| 4,661,112 A | 4/1987 | Muller | |
| 4,662,889 A | 5/1987 | Zicher et al. | |
| 4,664,668 A | 5/1987 | Beck et al. | |
| 4,685,923 A | 8/1987 | Mathys | |
| 4,711,233 A | 12/1987 | Brown | |
| 4,715,859 A | 12/1987 | Schlehas et al. | |
| 4,735,625 A | 4/1988 | Davidson | |
| 4,795,470 A | 1/1989 | Goymann et al. | |
| 4,795,474 A | 1/1989 | Horvath | |
| 4,808,186 A | 2/1989 | Smith | |
| 4,813,962 A | 3/1989 | Deckner et al. | |
| 4,822,365 A | 4/1989 | Walker et al. | |
| 4,822,369 A | 4/1989 | Oueveau et al. | |
| 4,846,840 A | 7/1989 | Leclerq | |
| 4,865,604 A | 9/1989 | Rogozinski | |
| 4,888,020 A | 12/1989 | Horber | |
| 4,904,269 A | 2/1990 | Elloy et al. | |
| 4,908,035 A | 3/1990 | Deckner et al. | |
| 4,919,674 A | 4/1990 | Schelhas | |
| 4,919,678 A | 4/1990 | Kranz | |
| 4,936,856 A | 6/1990 | Keller | |
| 4,938,771 A | 7/1990 | Vescei et al. | |
| 4,938,773 A | 7/1990 | Strand | |
| 4,950,298 A | 8/1990 | Gustilo et al. | |
| 4,955,912 A | 9/1990 | Berchem | |
| 4,955,919 A | 9/1990 | Pappas et al. | |
| 4,963,153 A | 10/1990 | Noes Berger et al. | |
| 4,963,154 A | 10/1990 | Anapliotis et al. | |
| 4,969,910 A | 11/1990 | Frey et al. | |
| 4,997,447 A | 3/1991 | Shelley | |
| 5,002,581 A | 3/1991 | Paxson et al. | |
| 5,011,497 A | 4/1991 | Persson et al. | |
| 5,019,107 A | 5/1991 | Schelhas | |
| 5,041,140 A | 8/1991 | Teinturies | |
| 5,049,393 A | 9/1991 | Noon et al. | |
| 5,080,675 A | 1/1992 | Lawes et al. | |
| 5,080,677 A | 1/1992 | Shelley | |
| 5,080,678 A | 1/1992 | Spotorno et al. | |
| 5,108,446 A | 4/1992 | Wagner et al. | |
| 5,108,451 A | 4/1992 | Forte | |
| 5,116,374 A | 5/1992 | Stone | |
| 5,123,927 A * | 6/1992 | Duncan et al. | 623/20.21 |
| 5,133,763 A | 7/1992 | Mullers | |
| 5,146,933 A | 9/1992 | Boyd | |
| 5,147,406 A | 9/1992 | Houston et al. | |
| 5,151,521 A | 9/1992 | Morita et al. | |
| 5,156,631 A | 10/1992 | Merletee | |
| 5,171,276 A | 12/1992 | Caspari et al. | |
| 5,181,925 A | 1/1993 | Houston et al. | |
| 5,197,987 A | 3/1993 | Koch et al. | |
| 5,197,989 A | 3/1993 | Hinckfuss et al. | |
| 5,201,881 A | 4/1993 | Evans | |
| 5,201,882 A | 4/1993 | Paxson | |
| 5,217,498 A | 6/1993 | Henssge et al. | |
| 5,217,499 A | 6/1993 | Shelley | |
| 5,222,985 A | 6/1993 | Homsy | |
| 5,282,868 A | 2/1994 | Bahler | |
| 5,290,314 A | 3/1994 | Koch et al. | |
| 5,314,478 A | 5/1994 | Oka et al. | |
| 5,314,493 A | 5/1994 | Mikhail | |
| 5,314,494 A | 5/1994 | Huiskes et al. | |
| 5,316,550 A | 5/1994 | Forte | |
| 5,323,765 A | 6/1994 | Brown | |
| 5,326,376 A | 7/1994 | Warner et al. | |
| 5,330,534 A | 7/1994 | Herrington et al. | |
| 5,336,268 A | 8/1994 | Rispeter | |
| 5,344,459 A | 9/1994 | Swartz | |
| 5,358,525 A | 10/1994 | Fox et al. | |
| 5,370,699 A | 12/1994 | Hood et al. | |
| 5,376,064 A | 12/1994 | Cerny | |
| 5,376,125 A | 12/1994 | Winkler | |
| 5,387,244 A | 2/1995 | Breard | |
| 5,389,107 A | 2/1995 | Nassar et al. | |
| 5,405,402 A | 4/1995 | Dye et al. | |
| 5,405,403 A | 4/1995 | Mikhail | |
| 5,405,411 A | 4/1995 | McCoy | |
| 5,415,662 A | 5/1995 | Ferrante et al. | |
| 5,425,779 A | 6/1995 | Schlosser et al. | |
| 5,448,489 A | 9/1995 | Reuben | |
| 5,458,643 A | 10/1995 | Oka et al. | |
| 5,458,651 A | 10/1995 | Lawes | |
| 5,489,311 A | 2/1996 | Cippoletti | |
| 5,491,882 A | 2/1996 | Walston et al. | |
| 5,507,814 A | 4/1996 | Gilbert et al. | |
| 5,507,818 A | 4/1996 | McLaughlin | |
| 5,507,820 A | 4/1996 | Pappas | |
| 5,507,823 A | 4/1996 | Walston et al. | |
| 5,507,830 A | 4/1996 | DeMane et al. | |
| 5,507,833 A | 4/1996 | Bohn | |
| 5,507,836 A | 4/1996 | Pohling | |
| 5,514,182 A | 5/1996 | Shea | |
| 5,514,184 A | 5/1996 | Doi et al. | |
| 5,522,904 A | 6/1996 | Moran et al. | |
| 5,527,317 A | 6/1996 | Ashby et al. | |
| 5,549,686 A * | 8/1996 | Johnson et al. | 623/20.27 |
| 5,641,323 A | 6/1997 | Caldarise | |
| 5,658,345 A | 8/1997 | Willi | |
| 5,702,478 A | 12/1997 | Tornier | |
| 5,879,387 A | 3/1999 | Jones et al. | |
| 6,302,916 B1 | 10/2001 | Townley et al. | |
| 6,626,949 B1 | 9/2003 | Townley | |
| 2002/0143402 A1 | 10/2002 | Steinberg | |
| 2003/0114934 A1 | 6/2003 | Steinberg | |

FOREIGN PATENT DOCUMENTS

| | | |
|---|---|---|
| CH | 644511 | 8/1994 |
| DE | 2 247 721 | 4/1974 |
| DE | 3215583 | 12/1982 |
| EP | 46926 A2 * | 3/1982 |
| EP | 0 308 081 | 3/1989 |
| FR | 2061466 | 6/1971 |
| FR | 2290880 | 6/1976 |
| FR | 2707870 A1 * | 1/1995 |
| GB | 2 126 096 | 3/1984 |
| IL | 115168 | 9/1995 |
| WO | 9410941 | 5/1994 |
| WO | 9426204 | 11/1994 |

OTHER PUBLICATIONS

RM Isoelastic Bevelled Acetabular Cup.
Natural Lock Acetabular Component.
Mathys AG Bettlach: RM Pressfit Cup, Mathys-Orthopaedics website.
E. Morscher, R. Mathys, H.R. Henche, ISO-Elastic Endoprosthesis—a New Concept in Artificial Joint Replacement, 1976, Robert Mathys website.
J.B. Medley, R.M. Pilliar, E.W. Wong, A.B. Strong, Hydrophilic polyurethane elastomers for hemiarthroplasty: a preliminary in vitro wear study, Journal of Engineering in Medicine, 1980, pp. 59-65, vol. 9, No. 2.
E.W. Morscher, W. Dick, V. Kernen, Cementless Fixation of Polyethylene Acetabular Component in Total Hip Arthroplasty, Archives of Orthopaedic and Traumatic Surgery, 1982, pp. 223-230.
N.D. Reis, M.I.B. Besser, N. Antman, O. Israel, A. Yavor, The Robert Mathys Isolastic Cementless Primary Total Hip Replacement: The First 50 Cases after 5-6 years, , 1988, , Israel.
S.E. Clift, Finite-element analysis in cartilage biomechanics, Journal of Biomed. Eng., 1992, pp. 217-221, vol. 14, Butterworth-Heinemann for BES.

Adekunle Oloyede, Neil D. Broom, A Physical Model for the Time-Dependent Deformation of Articular Cartilage, Connective Tissue Research, 1993, pp. 251 261, vol. 29, Gordon and Breach Science Publishers S.A., United States.

Adekunle Oloyede, Neil D. Broom, Stress-Sharing Between the Fluid and Solid Components of Articular Cartilage under Varying Rates of Compression, Connective Tissue Research, 1993, pp. 127-141, vol. 30, Gordon and Breach Science Publishers S.A., United States.

Adekunle Oloyede, Neil D. Broom, The Generalized Consolidation of Articular Cartilage: An Investigation of Its Near-Physiological Response to Static Load, Connective Tissue Research, 1994, pp. 75-86, vol. 31, Gordon and Breach Science Publishers S.A.

Robert C. Schenck, Jr., Kyriacos A. Athanasiou, George Constantinides, Eduardo Gomez, A Biomechanical Analysis of Articular Cartilage of the Human Elbow and a Potential relationship to Osteochondritis Dissecans, Clinical Orthopaedics and Related Research, 1994, pp. 305-312, No. 299, J.B. Lippincott Company.

Wenbo Zhu, Kenneth Y. Chern, Van C. Mow, Anisotropic Viscoelastic Shear Properties of Bovine Meniscus, Clinical Orthopaedics and Related Research, 1994, pp. 34-45, No. 306, J.B. Lippincott Company.

D.D. Auger, D. Dowson, J. Fisher, Cushion form bearings for total knee joint replacement—part 2: wear and durability, Journal of Engineering in Medicine, Mar. 4, 1995, pp. 83-91, vol. 209, University of Leeds.

M. Tissakht, A.M. Ahmed, Tensile Stress-Strain Characteristics of the Human Meniscal Material, Journal of Biomechanics, 1995, pp. 411-422, vol. 28, Elsevier Science Ltd., Great Britain James W. Pritchett, M.D. Affidavit Apr. 21, 2007.

N. Nic An Ghaill, E.G. Little, Determination of the mechanical properties of Bionate 80A and Bionate 75D for the stress analysis of cushion form bearings, Journal of Engineering in Medicine, 2008, pp. 683-694, vol. 222, University of Limerick, Castletroy, Limerick, Ireland.

Michael P. Mandarino, The Use of a Polyurethane Polymer (Ostamer) in Fractured and Diseased Bones.

Steinberg, D.R. and Steinberg, M.E., The Early History of Arthroplasty in the United States. Clinical Orthopaedics and Related Research. 374:55-89, 2000.

Dawson, D. et al. Design considerations for cushion form bearings in artificial hip joints. Journal of Engineering in Medicine. 205:59-68, 1991.

Greco, R.S., Editor. Implantation Biology-The Host Response and Biomedical Devises. Correction Press. Boca Raton, 1994. pp. 6, 11, 12.

Whittick, W.J. and Bonar, C.J. Polyurethane Polymer—Its Use in Canine Orthopaedics. Can. Vet. Journal 3:308-316, 1962.

Townley, C.O. Hemi and Total Articular Replacement Arthroplasty of the Hip with the Fixed Femoral Cup. Orthopedic Clinics of North America. 12(4):869-894, 1982.

European Patent Office, Partial European Search Report for EP04078063, mailed Oct. 2, 2008, 7 pages.

* cited by examiner

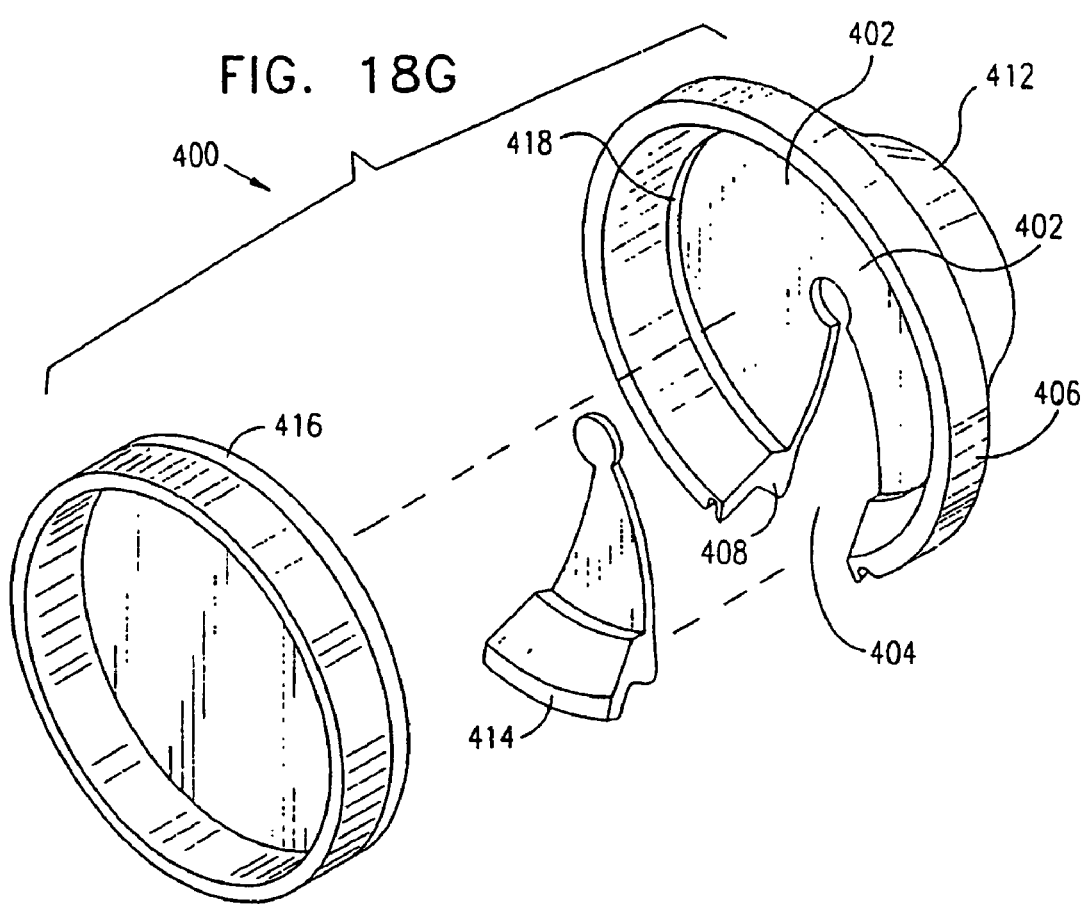

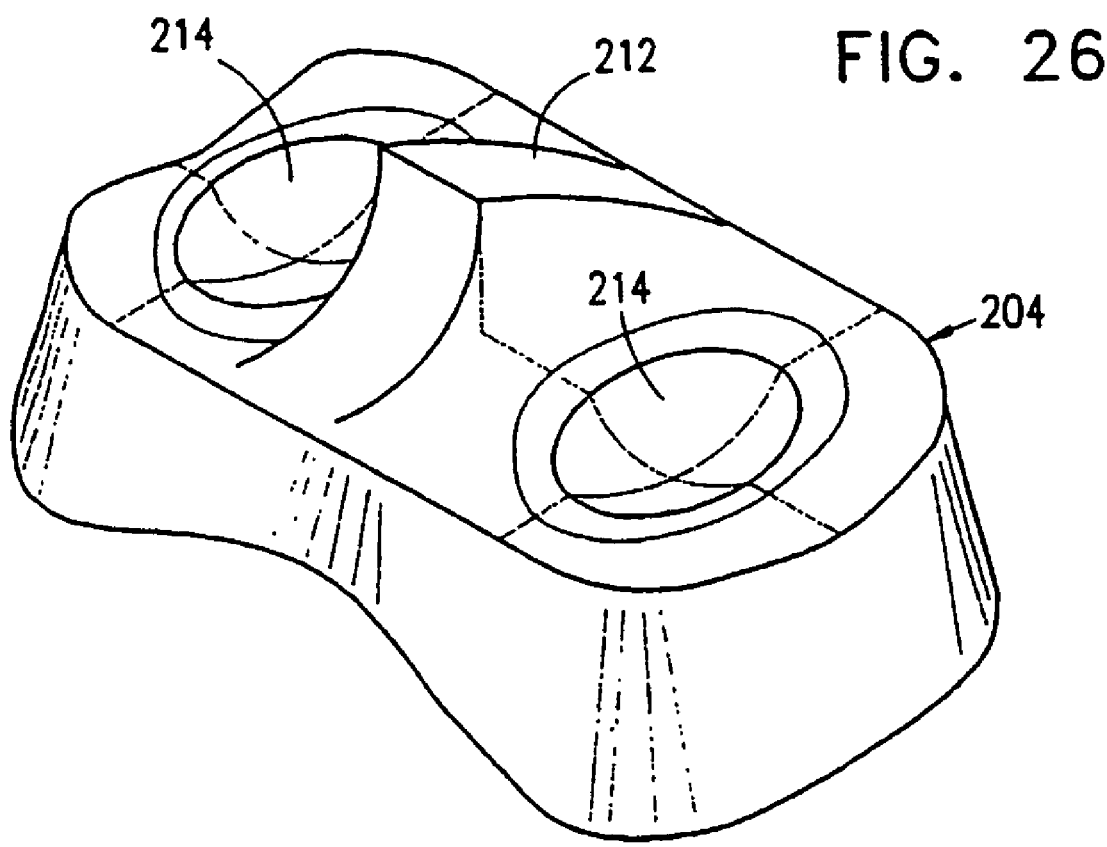

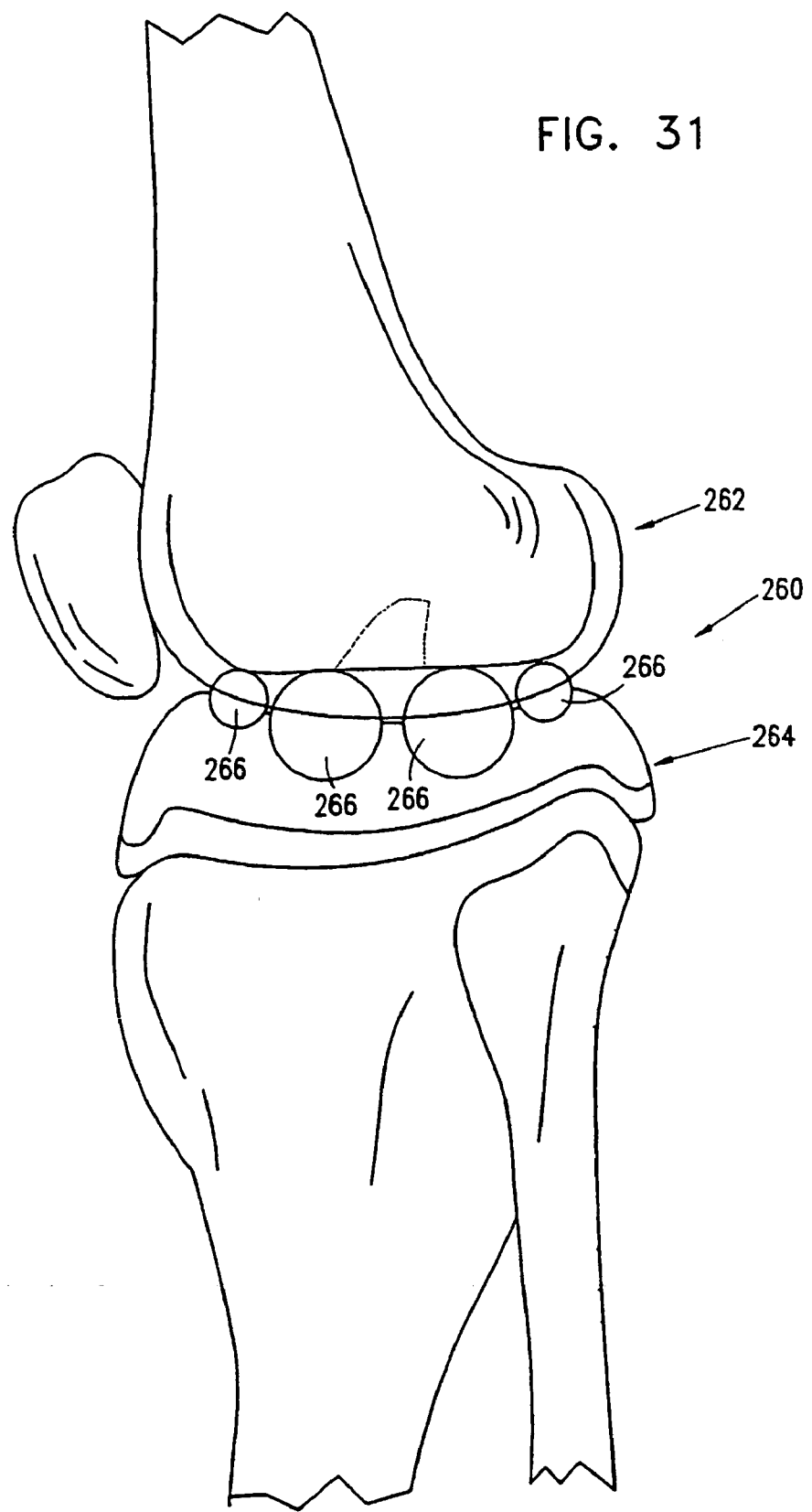

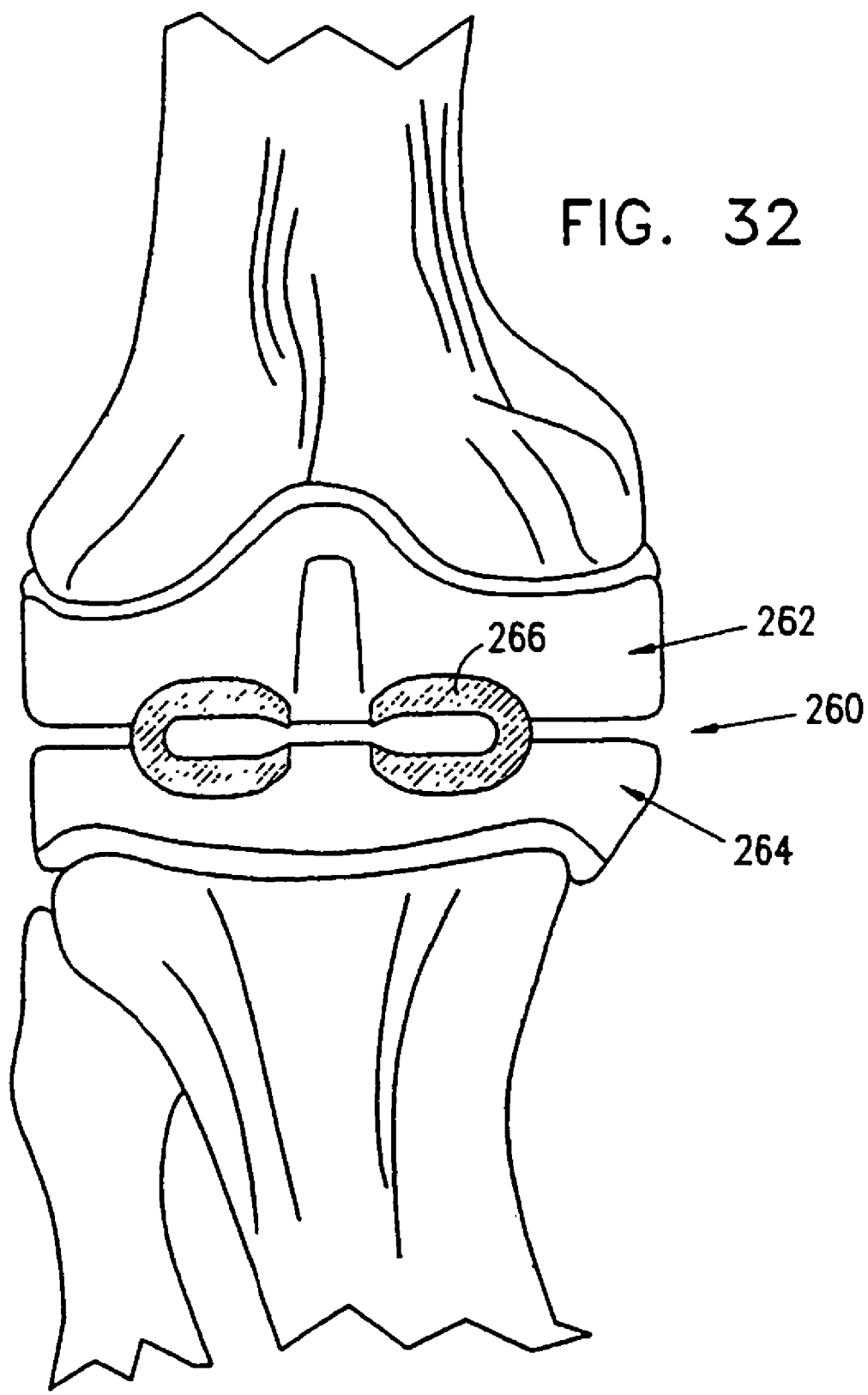

KNEE PROSTHESIS HAVING A DEFORMABLE ARTICULATION SURFACE

This application is a continuation of U.S. Non-Provisional application Ser. No. 10/289,126, filed on 5 Nov. 2002, U.S. Non-Provisional application Ser. No. 09/902,701, filed 5 Sep. 2001 now abandoned, U.S. Non-Provisional patent application Ser. No. 09/043,076, filed Feb. 2, 1999 now abandoned, which claims benefit of 35 U.S.C. §119(e) of Israeli Patent Application No.: 115168, filed 4 Sep. 1995, the contents of which are incorporated herewith by reference in their entirety.

FIELD OF THE INVENTION

The present invention relates to apparatus and methods for joint prosthesis surgery generally.

Joint prostheses are well known in the art. Generally joint prostheses include a metal portion, typically constructed of steel or titanium, which articulates with a bony portion of the body. Non-articulating portions of the prosthesis are generally fixedly attached to tissue or bone. For example, a hip joint prosthesis of the art generally includes a metallic femoral head which articulates with a portion of the hip bone, and a metallic stem which is fixedly attached to the femur.

Several problems are associated with prostheses of the art, for example, due to the mismatch between material properties of the prosthesis and bone. The contact between metal and bone may cause fretting wear of the bone. The difference in coefficient of thermal expansion between metal and bone may cause discomfort to the patient, especially during weather changes. The metallic prosthesis provides virtually no shock absorption or damping.

It is known that a bone grows or regenerates according to the stress which it must bear. The metal prosthesis generally bears a much larger portion of weight than the surrounding bone. The reduced stress on the surrounding bone may tend to contribute to degeneration and recession of the bone, and to create an undesirable gap between the bone and the prosthesis.

In order to overcome the aforementioned problems, a great variety of prostheses with resilient portions have been proposed and developed. The following U.S. Patents are believed to be representative of the art: U.S. Pat. Nos. 5,522,904, 5,514,184, 5,514,182, 5,507,836, 5,507,833, 5,507,830, 5,507,823, 5,507,820, 5,507,818, 5,507,814, 5,491,882, 5,489,311, 5,458,651, 5,458,643, 5,448,489, 5,425,779, 5,415,662, 5,405,411, 5,405,403, 5,389,107, 5,387,244, 5,376,125, 5,376,064, 5,370,699, 5,358,525, 5,344,459, 5,336,268, 5,330,534, 5,326,376, 5,316,550, 5,314,494, 5,314,493, 5,314,478, 5,290,314, 5,282,868, 5,222,985, 5,217,499, 5,217,498, 5,201,882, 5,201,881, 5,197,989, 5,197,987, 5,181,925, 5,171,276, 5,156,631, 5,151,521, 5,147,406, 5,146,933, 5,133,763, 5,116,374, 5,108,451, 5,108,446, 5,080,677, 5,490,393, 5,041,140, 5,019,107, 5,002,581, 4,997,447, 4,963,154, 4,963,153, 4,955,919, 4,955,912, 4,950,298, 4,938,773, 4,938,771, 4,936,856, 4,919,678, 4,919,674, 4,908,035, 4,904,269, 4,888,020, 4,822,365, 4,813,962, 4,808,186, 4,795,474, 4,795,470, 4,715,859, 4,664,668, 4,662,889, 4,661,112, 4,570,270, 4,344,193 and 3,875,594.

The present invention seeks to provide improved joint prostheses which, inter alia, help overcome the above mentioned problems of the prior art.

The prostheses provide shock absorption, damping and resiliency. Portions of the prostheses which interface with human tissue are preferably constructed of resilient materials which are compatible with human bone or tissue, such as certain types of polyurethane. Certain portions of the prostheses may be constructed of composite materials whose mechanical or physical properties may be optimized, such as to match properties of the local human bone or tissue. By matching properties of the local bone or tissue, the prosthesis behaves mechanically, structurally and thermally in a manner similar to the local bone or tissue, which helps make the prosthesis more efficient and comfortable.

An important feature of the prostheses is that they help distribute stresses optimally, thereby stimulating regeneration of bone.

The present invention is applicable for any joint in which there is free movement, known in technical terms as a true diarthrosis. True diarthroses include:

1. Gliding joints, known as arthrodias, in which the surfaces of the joint are flat, such as in the carpal bones;
2. Hinge joints, known as ginglymi, such as the knee or elbow;
3. Condyloid joints, known as condylarthroses, which allow flexion, extension and lateral movement, but no rotation, such as the wrist, and saddle-shaped joints which allow the same type of movement as condyloid joints, but are generally stronger, such as the carpometacarpal joint of the thumb;
4. Ball and socket joints, known as enarthroses, such as the hip and the shoulder; and
5. Pivot joints, known as trochoides, which only allow rotation, such as the radio-ulnar joints.

The present invention will be described in detail hereinbelow with respect to a prosthesis for an enarthrosis, such as the hip joint, and to a prosthesis for a ginglymus, such as the knee joint. It is appreciated, however, that a prosthesis for any true diarthrosis is in the scope of the present invention.

In a radical departure from the prior art, and in accordance with one embodiment of the present invention, a hip joint prosthesis is provided which includes an artificial femoral head which is not fixedly attached to the femur, but rather articulates with both the femur and the acetabulum. The artificial femoral head is generally spherical and may absorb shocks, provide damping and/or be resilient. A separate, artificial femoral head is easier to insert than the prostheses of the prior art which have a stem.

In addition, the artificial femoral head may be provided with delimiting rails or grooves which serve to define and limit the movement paths of the femur with respect to the body, if required, and dislocation of the joint is substantially prevented. The delimiting rails or grooves may also serve as bumpers which damp and cushion the femoral head at the limits of its articulation.

The prostheses of the present invention may also be provided with passageways for fluid, such as synovial fluid. Fluid present in these Passageways helps to lubricate the prosthesis and provides viscous damping.

Since the prostheses of the present invention are resilient, they geometrically adapt themselves to changes in static and dynamic forces borne by the joint. In the case of the hip joint prosthesis of the present invention, for example, normal raising of the thigh does not apply substantial forces on the hip joint, and the resilient hip Joint prosthesis allows the freedom of movement of a ball and socket Joint with substantially no deformation nor obstruction to movement due to friction between the prosthesis and human tissue or bone, or between adjacent regions of the prosthesis, such as between the artificial femoral head and an artificial socket.

In contrast, when the person is standing, the static force of the weight of the person on the hip joint causes the resilient prosthesis to deform somewhat. i.e., to be squashed a certain amount. This deformation provides a relatively larger area for supporting the weight on the joint, thereby reducing pressure on the joint. The deformation also increases the friction force between the prosthesis and human tissue or bone, or between adjacent regions of the prosthesis, such as between the artificial femoral head and an artificial socket. The increased friction is beneficial because it does not hinder the stationary person; on the contrary, the increased friction increases stability of the person.

The resiliency of the prosthesis is also beneficial during sudden slips or falls. The dynamic and/or static forces due to the sudden movement tend to deform or squash the resilient prosthesis. As described above, the deformation reduces pressure on the Joint, reduces danger of the prosthesis detaching from the bone, and increases friction which helps provide stability during the slip or fall.

There is thus provided in accordance with a preferred embodiment of the present invention, a joint prosthesis including at least a first and a second load carrying member, the first load carrying member being substantially more shock absorbing and resilient than the second load carrying member.

In accordance with a preferred embodiment of the present invention, at least one of the load carrying members is characterized in having at least one of strength and elasticity generally similar to that of human cartilage.

There is also provided in accordance with a preferred embodiment of the present invention, a joint prosthesis including a plurality of alternating adjacent portions of substantially rigid and substantially resilient materials.

There is also provided in accordance with a preferred embodiment of the present invention, a joint prosthesis including a plurality of alternating adjacent first and second portions, the first portion having a substantially rigid configuration and the second portion having a substantially resilient configuration.

Preferably at least one of the first and the second portions is generally omega shaped. The joint prosthesis may include at least one portion compatible with human tissue. The joint prosthesis may have at least one hollow portion.

Preferably, any of the joint prostheses includes at least one delimiting rail or groove.

Preferably, any of the joint prostheses includes at least one passageway for a fluid.

There is also provided in accordance with a preferred embodiment of the present invention, a hip joint prosthesis including an artificial, spherical femoral head which is adapted to articulate with an acetabulum and an upper portion of a thigh.

There is also provided in accordance with a preferred embodiment of the present invention, a hip joint prosthesis including an artificial, self-articulating femoral head, the head being attachable to at least one of an acetabulum and an upper portion of a thigh.

Preferably, the hip joint prosthesis includes an artificial femoral head which is shock absorbing, provides damping and/or is substantially resilient.

Preferably, the femoral head has at least one hollow portion.

Further in accordance with a preferred embodiment of the present invention, the hip joint prosthesis also includes an artificial acetabulum attachable to an innominate bone, the artificial femoral head articulating with the artificial acetabulum.

Still further in accordance with a preferred embodiment of the present invention, the hip joint prosthesis also includes an artificial femoral socket attachable to a femur, the artificial femoral head articulating with the artificial femoral socket.

Further in accordance with a preferred embodiment of the present invention, the artificial femoral head includes a device for substantially preventing dislocation of the artificial femoral head from the artificial acetabulum, the artificial femoral socket, or both.

Preferably the device for substantially preventing dislocation is shock absorbing or resilient.

Further in accordance with a preferred embodiment of the present invention, the artificial femoral head includes at least one delimiting rail or groove. The delimiting groove may have a different geometrical shape than that of the rail. This permits providing various predetermined ranges and paths of motion.

Still further in accordance with a preferred embodiment of the present invention, the artificial femoral head has at least one passageway for a fluid.

Additionally in accordance with a preferred embodiment of the present invention, the hip joint prosthesis includes a sleeve which envelops at least one portion of the prosthesis and which is attachable to at least one of a portion of an innominate bone and a thigh. Preferably the sleeve includes a relatively high strength fabric.

Further in accordance with a preferred embodiment of the present invention, the artificial femoral socket is adapted to fit substantially snugly with at least one upper portion of a femur.

Still further in accordance with a preferred embodiment of the present invention, the artificial femoral head includes a plurality of alternating adjacent portions of substantially rigid and substantially resilient materials.

Additionally in accordance with a preferred embodiment of the present invention, the hip joint prosthesis further includes a stem insertable into a femur.

Further in accordance with a preferred embodiment of the present invention, the hip joint prosthesis includes an outer layer attachable to a femur, the outer layer including a material compatible with human tissue.

There is also provided in accordance with a preferred embodiment of the present invention, a knee joint prosthesis including a femoral portion and a tibial portion, the femoral portion being attachable to a femur and the tibial portion being attachable to a tibia, the femoral portion articulating with the tibial portion, wherein at least one of the femoral portion and the tibial portion is shock absorbing, provides damping or is substantially resilient.

In accordance with a preferred embodiment of the present invention, the knee joint prosthesis includes a device operative to limit motion of the tibia with respect to the femur.

Preferably, the device operative to limit motion of the tibia with respect to the femur, is shock absorbing.

Additionally in accordance with a preferred embodiment of the present invention, the femoral portion is generally convex and the tibial portion is generally concave.

Alternatively in accordance with a preferred embodiment of the present invention, the femoral portion is generally convex and the tibial portion is generally convex.

Further in accordance with a preferred embodiment of the present invention, the knee joint prosthesis includes at least one roller element, the femoral portion articulating with the tibial portion via the at least one roller element.

Preferably, the knee joint prosthesis has at least one fluid passageway.

There is also provided in accordance with a preferred embodiment of the present invention, a bone fastener including a plurality of alternating adjacent portions of substantially rigid and substantially resilient materials.

There is also provided in accordance with a preferred embodiment of the present invention, a bone fastener including a plurality of alternating adjacent first and second portions, the first portion having a substantially rigid configuration and the second portion having a substantially resilient configuration.

There is also provided in accordance with a preferred embodiment of the present invention, a method of incision of a ligament including forming a substantially wave-like incision in the ligament.

There is also provided in accordance with a preferred embodiment of the present invention, a method of insertion of a hip joint prosthesis including:
fixedly attaching a first joint element to an upper portion of a femur, the first joint element fitting substantially snugly with the upper portion of the femur;
fixedly attaching a second joint element to a portion of an innominate bone; and
inserting an artificial femoral head intermediate the first and the second joint elements, such that the artificial femoral head articulates with at least one of the first and the second joint elements.

Preferably, one or more natural or artificial ligaments may be used to strengthen the hip joint.

There is also provided in accordance with a preferred embodiment of the present invention, a method for limiting a range of movement of a hip joint including:
implanting a hip joint prosthesis comprising at least one delimiting rail and at least one delimiting groove, the at least one delimiting rail articulating with the at least one delimiting groove, such that the at least one delimiting groove limits articulation of the at least one delimiting rail therein.

The present invention will be understood and appreciated from the following detailed description, taken in conjunction with the drawings in which.

Figures 18A, 18B:
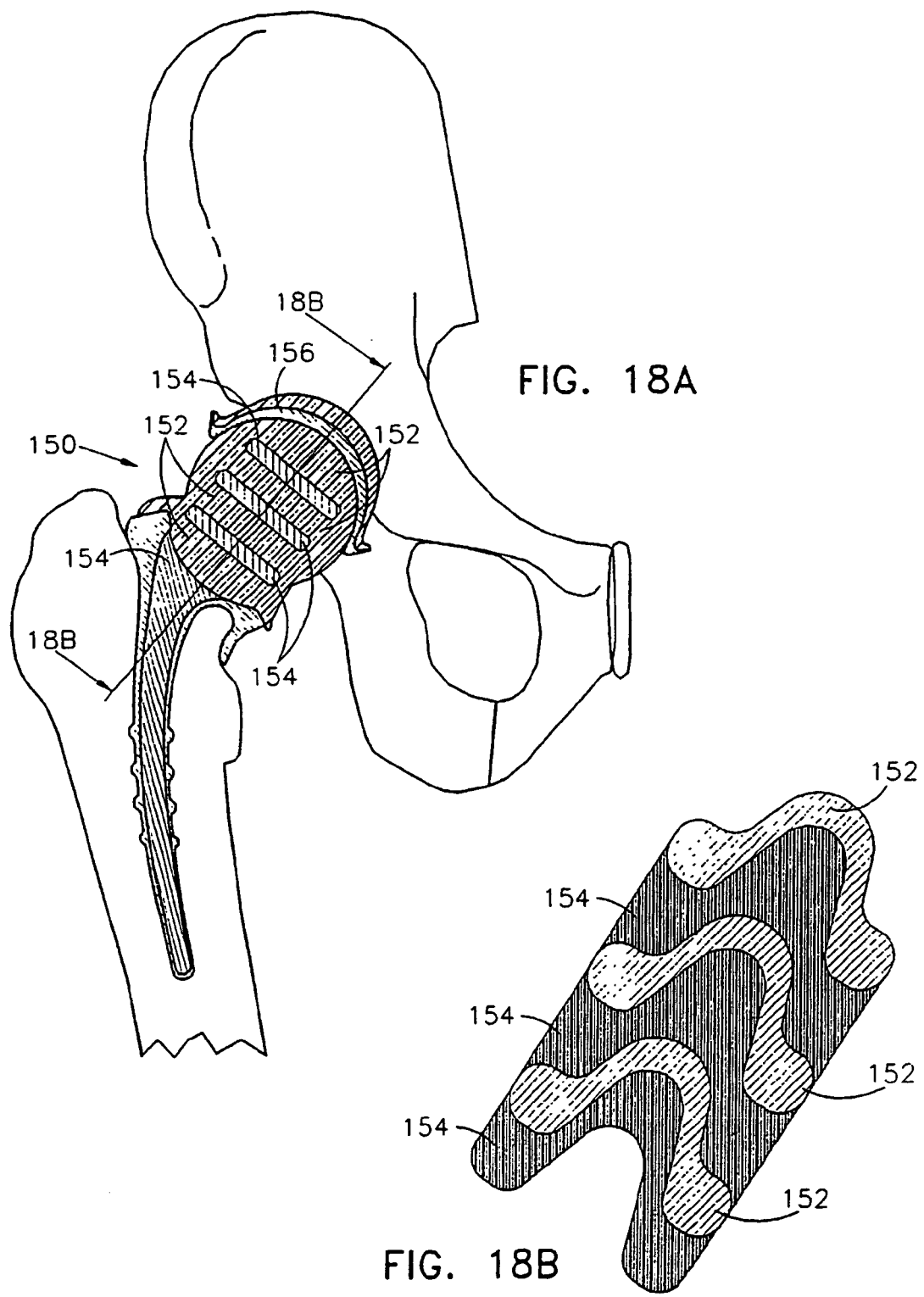
Figure 18C:
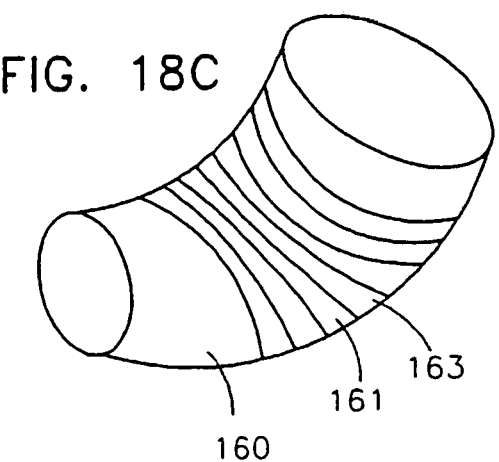
Figure 18D:
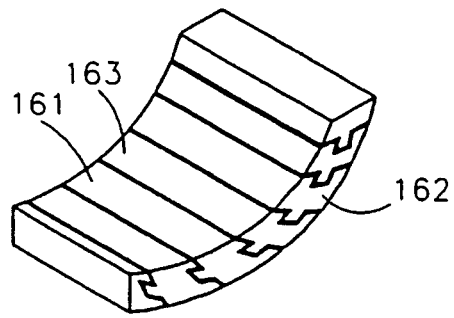
Figure 18E:
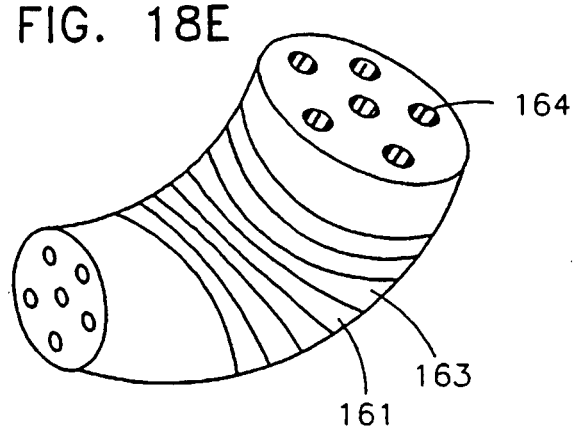
Figure 18F:
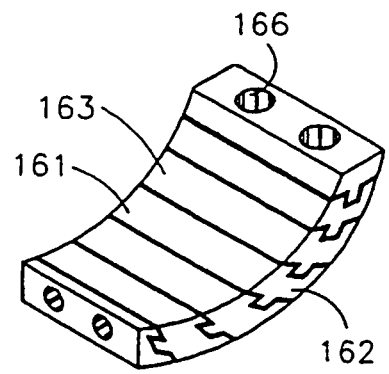
Figure 18H:
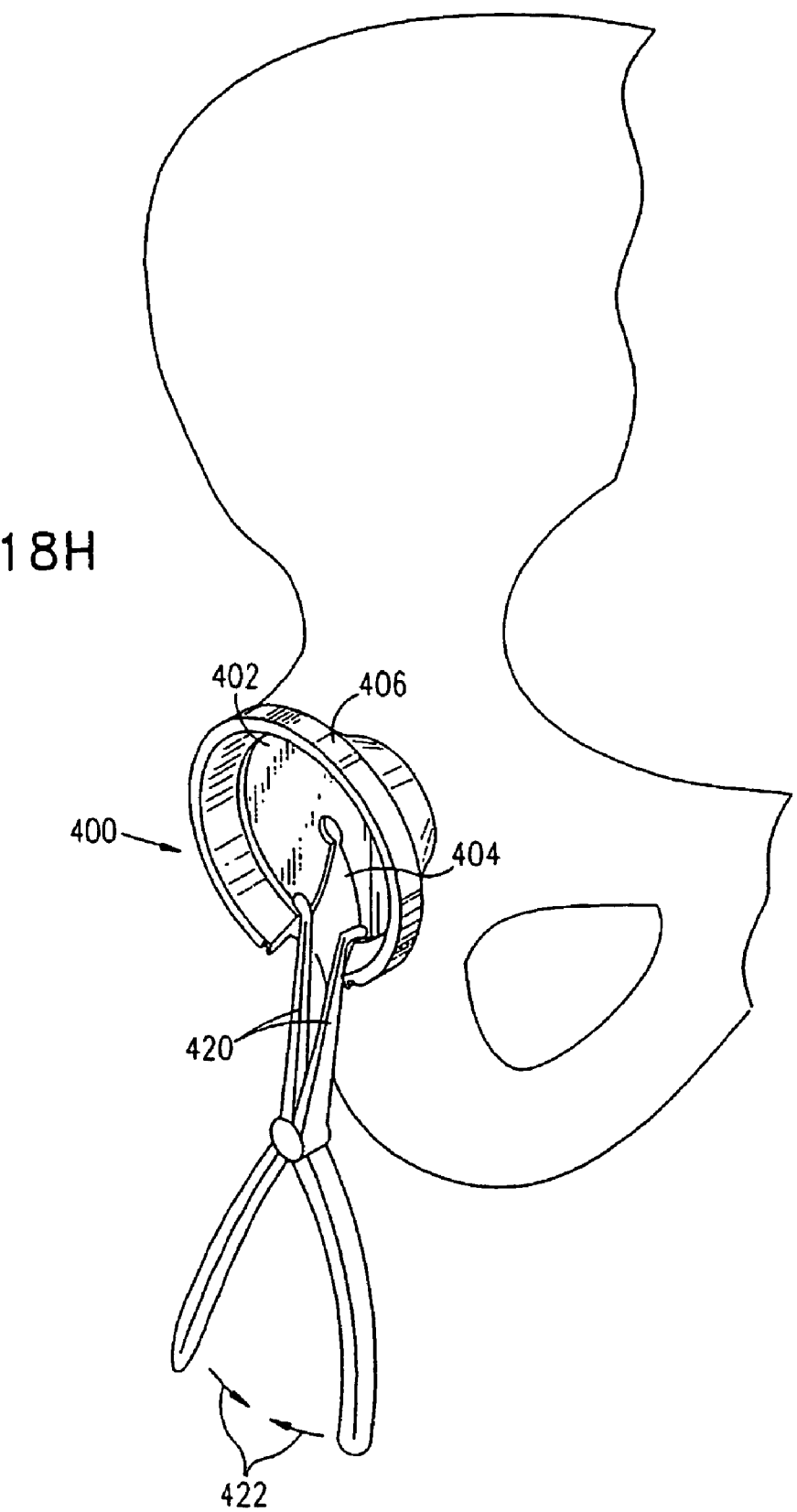
Figure 18I:
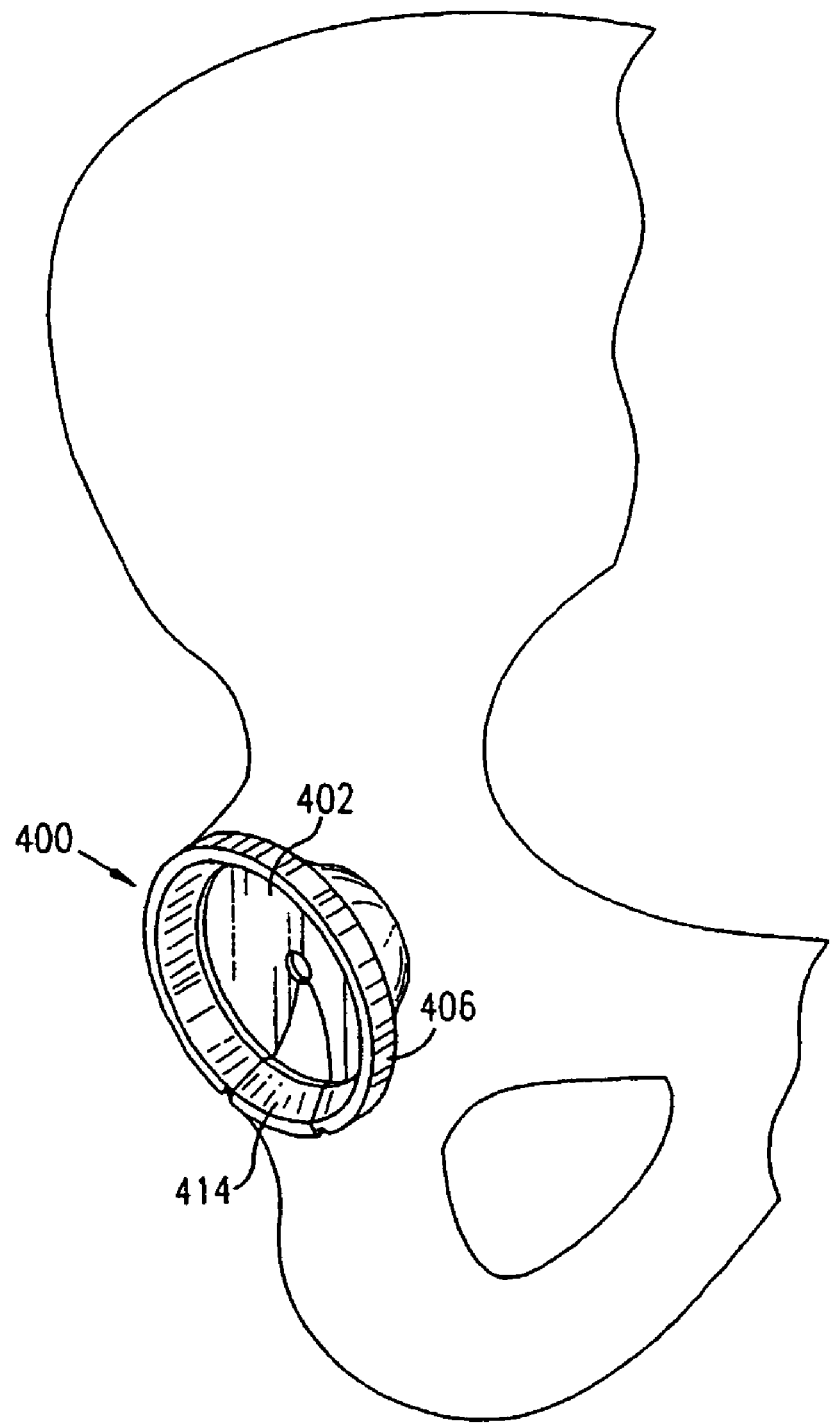
Figure 18J:
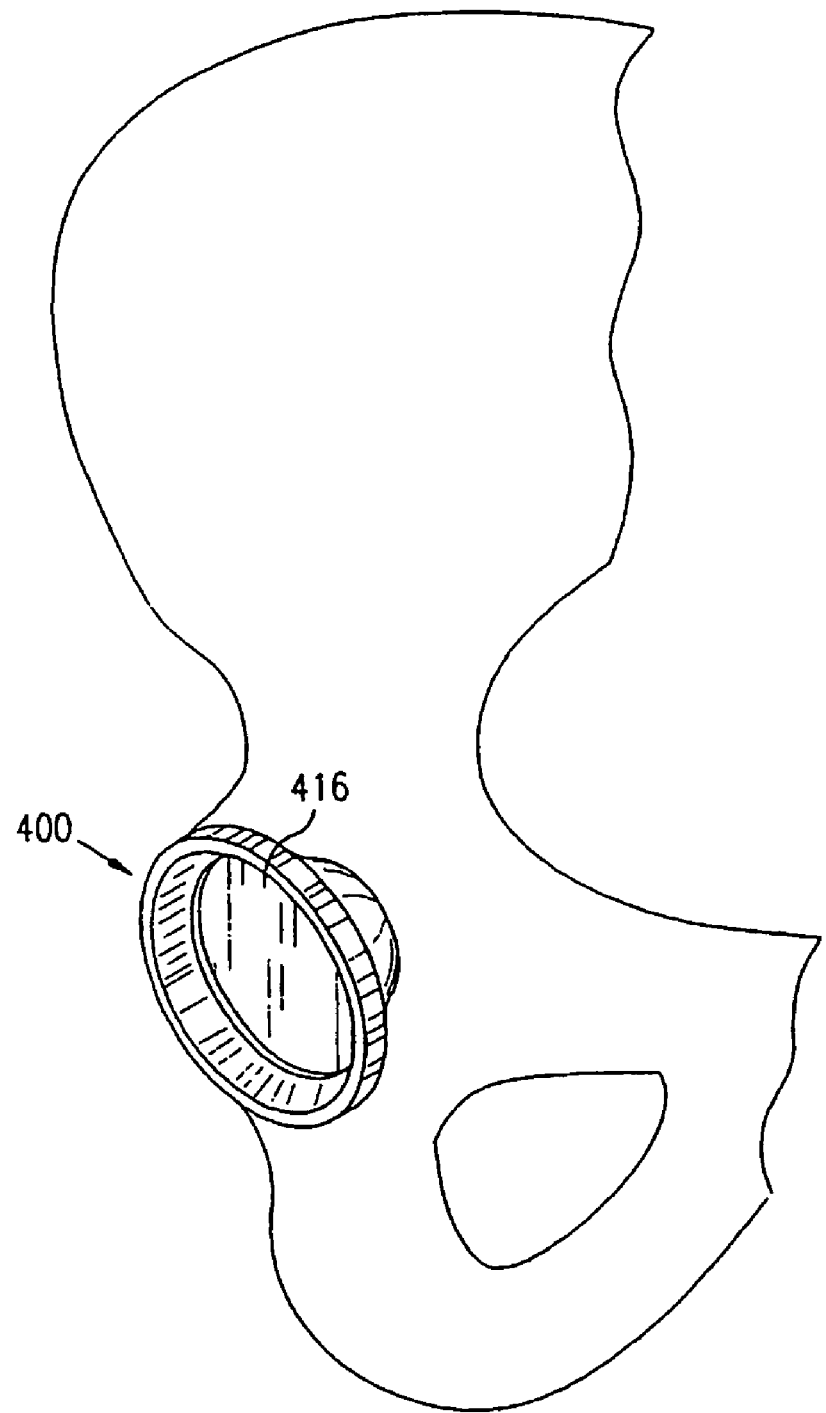
Figure 18K:
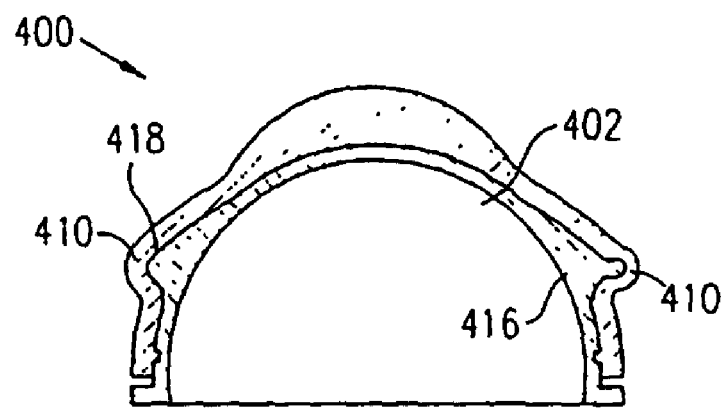
Figure 18L:
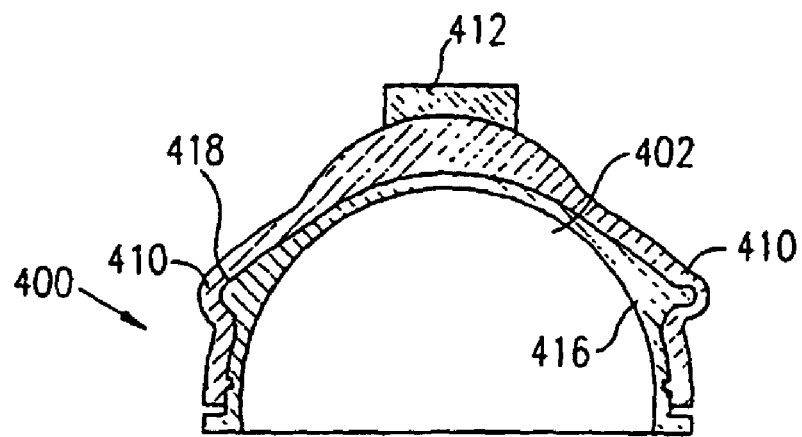
Figure 19C:
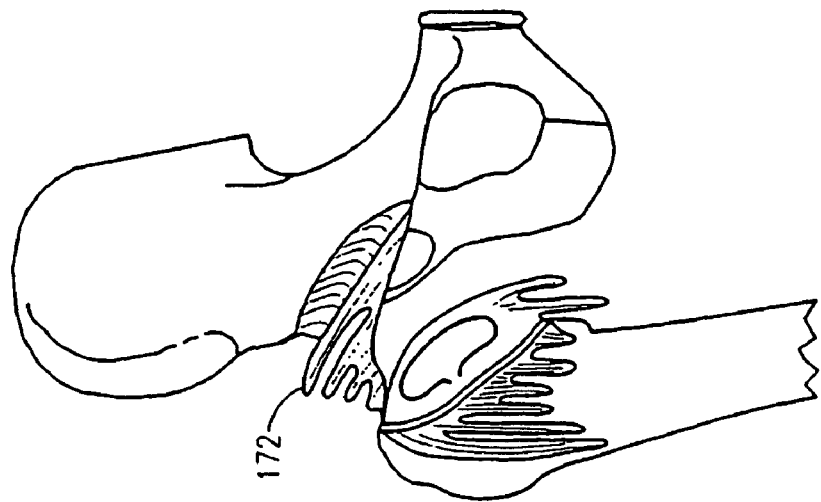
Figure 19B:
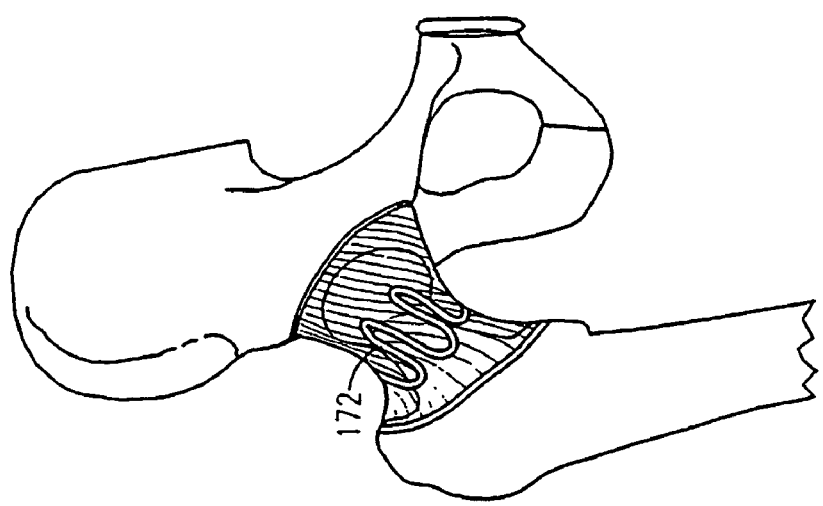
Figure 19A:
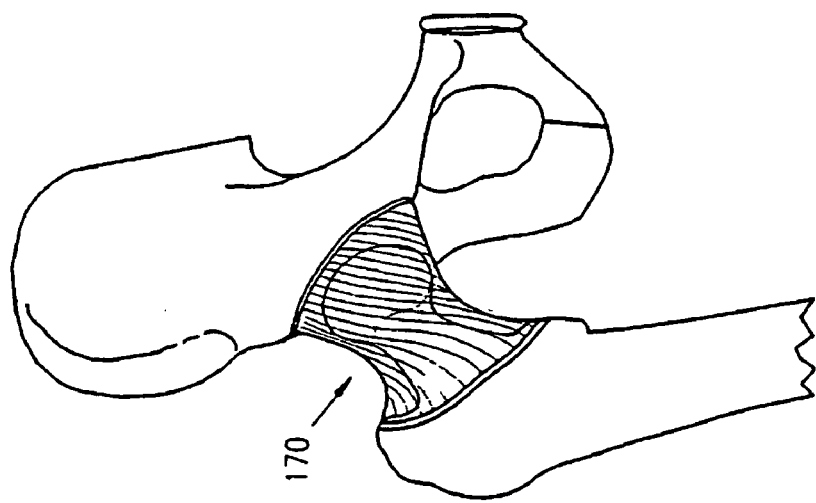
Figure 20:
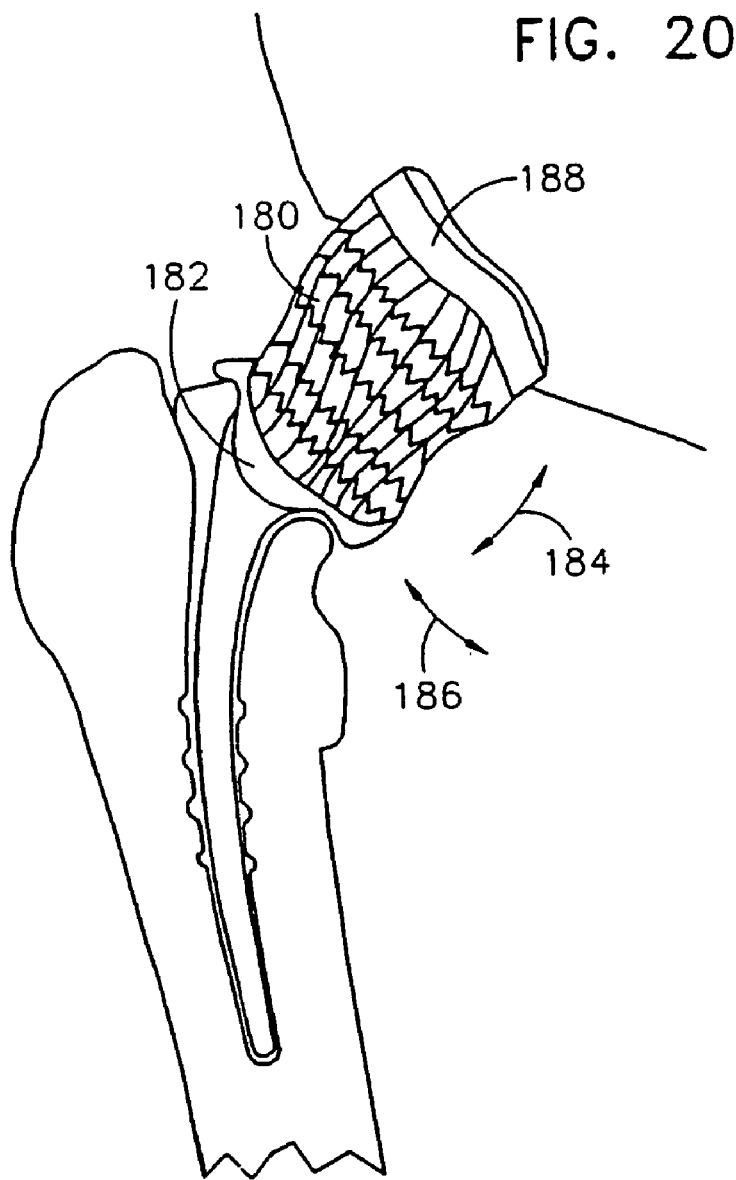
Figure 21:
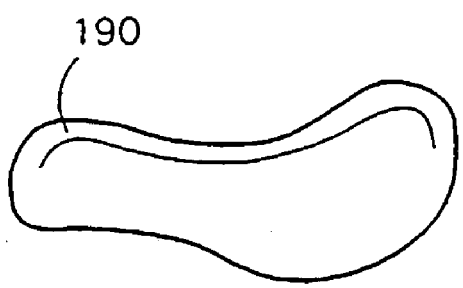
Figure 22:
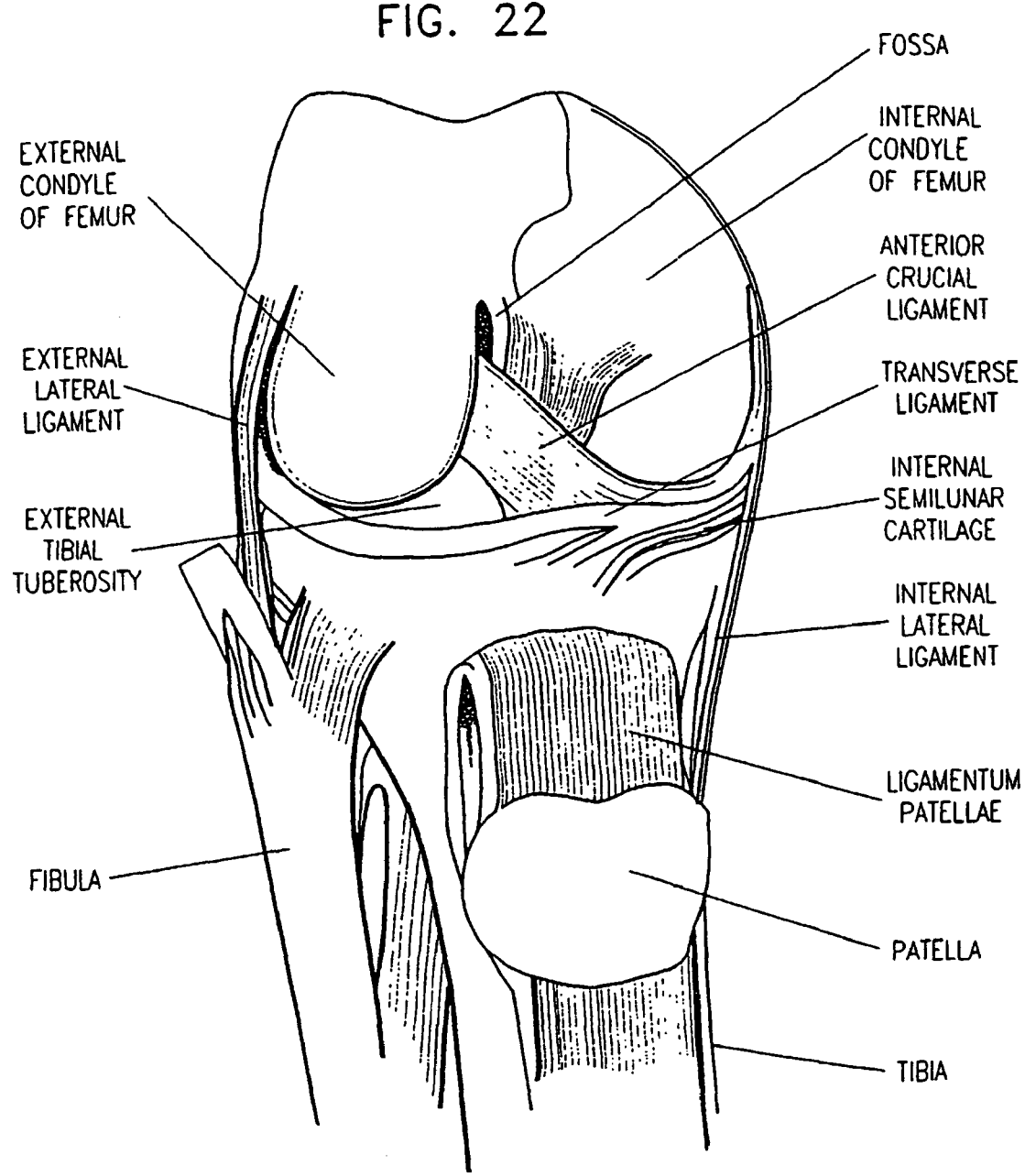
Figure 23:
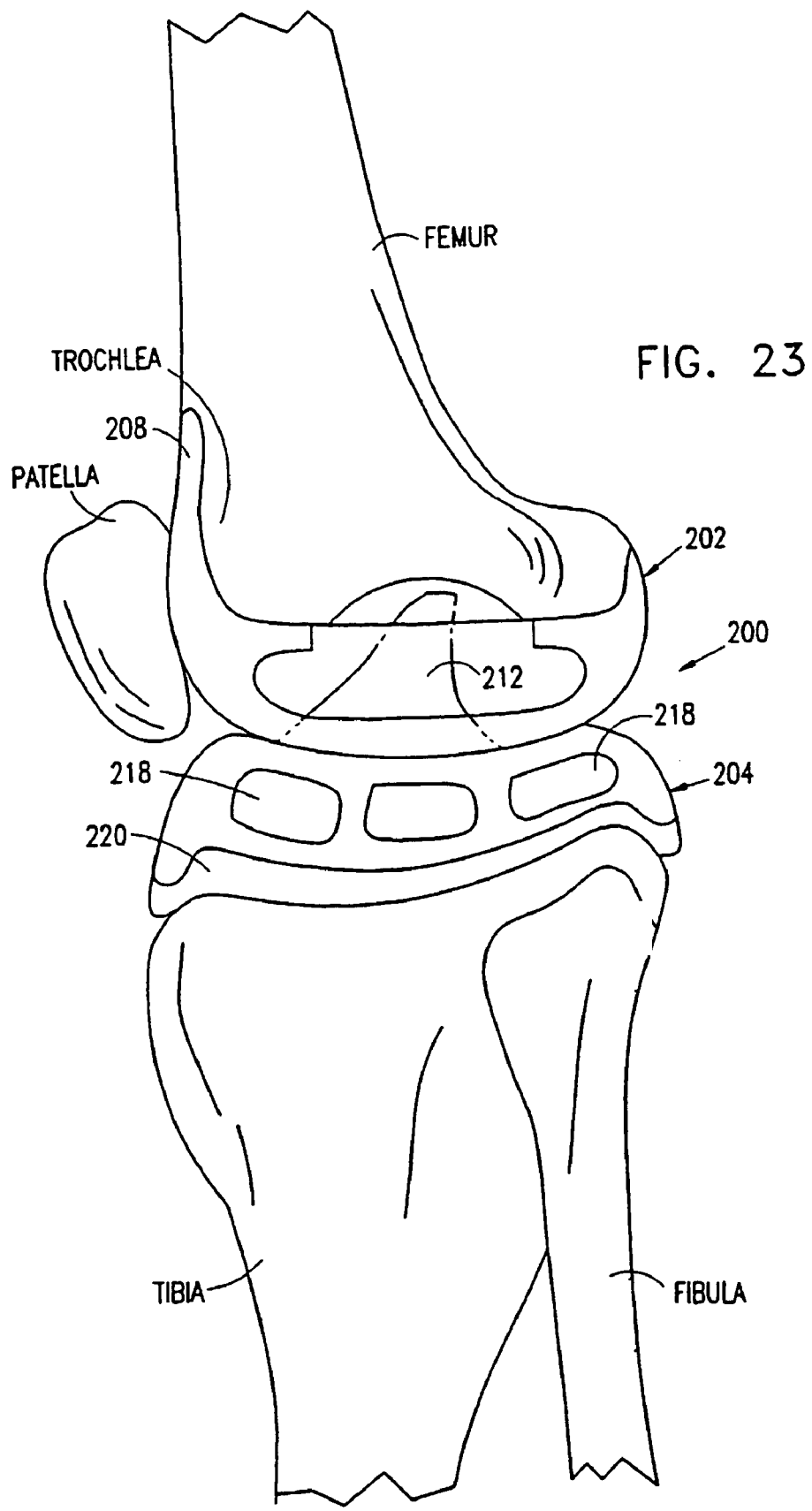
Figure 24:
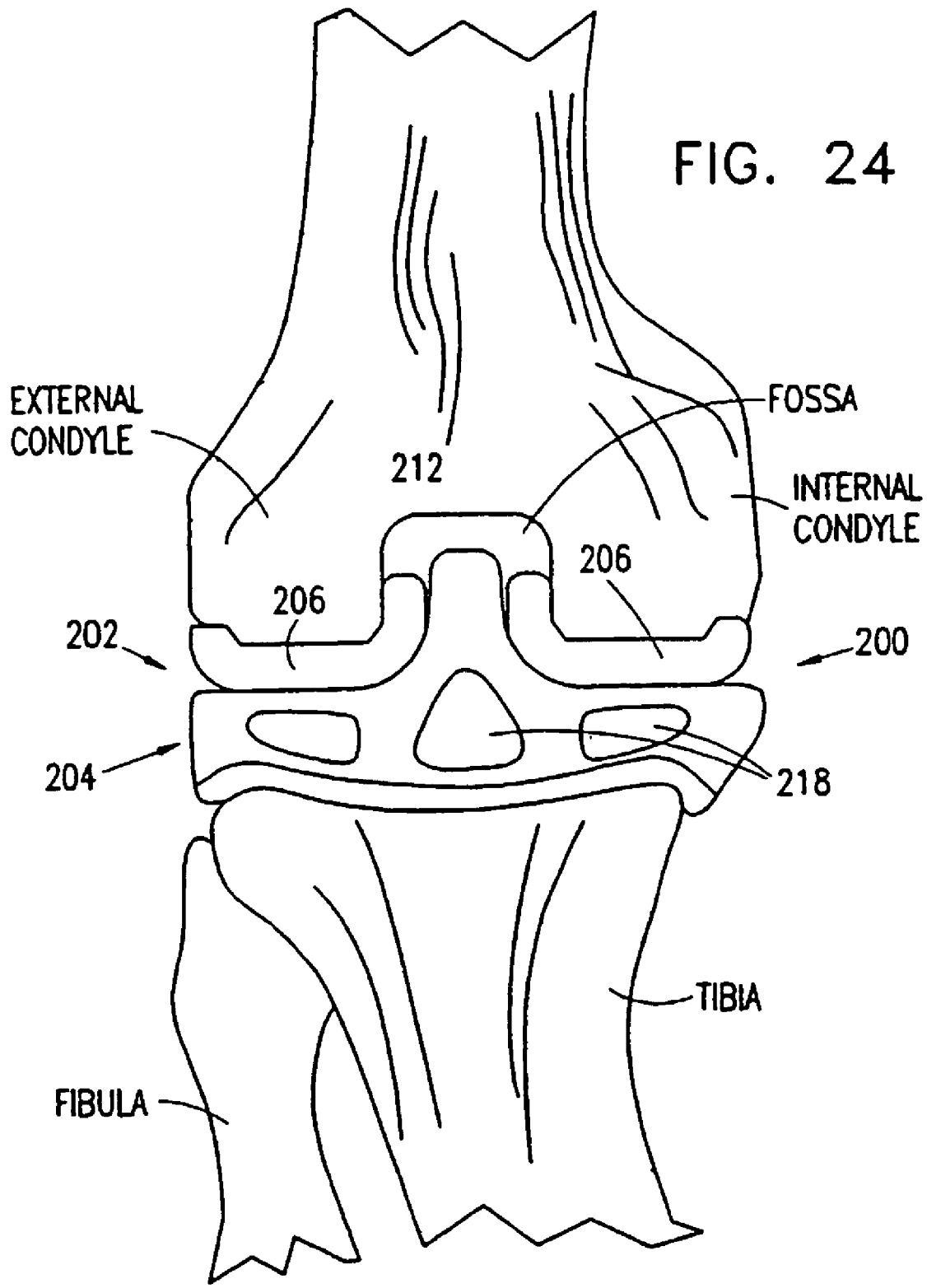
Figure 25:
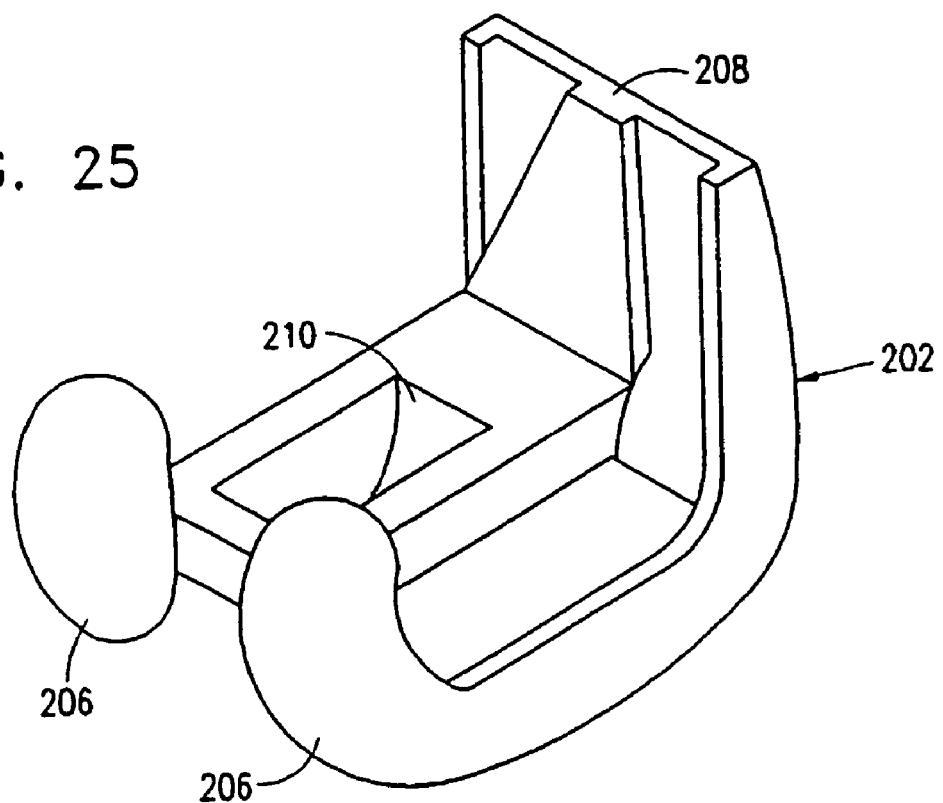
Figure 33:
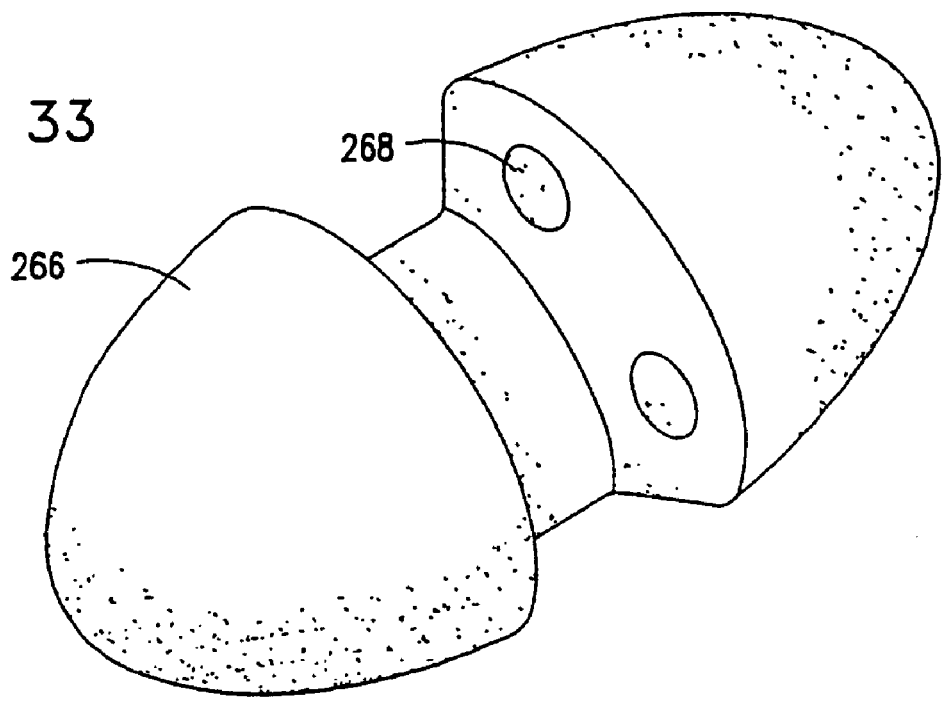
Figure 27:
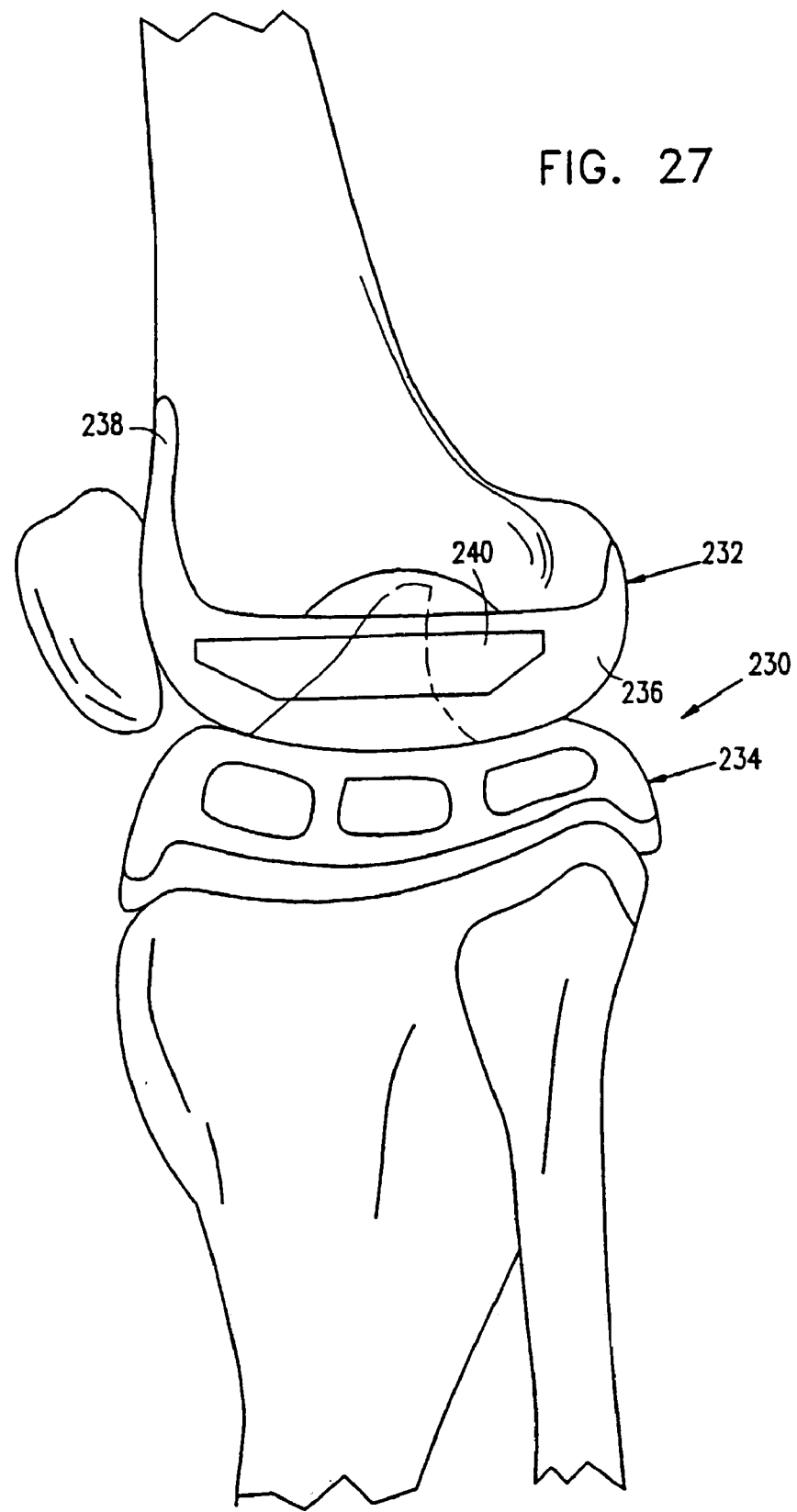
Figure 28:
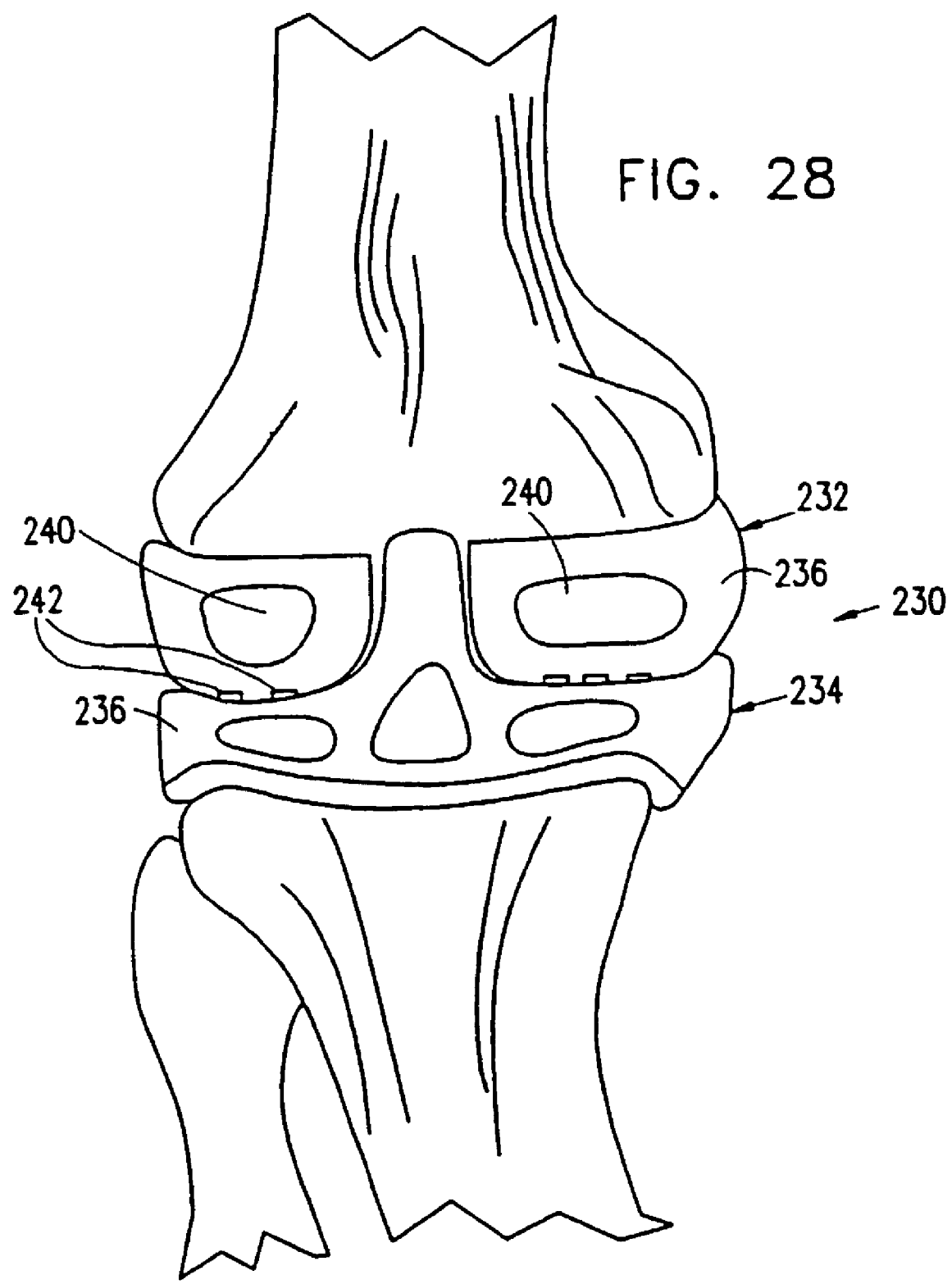
Figure 29:
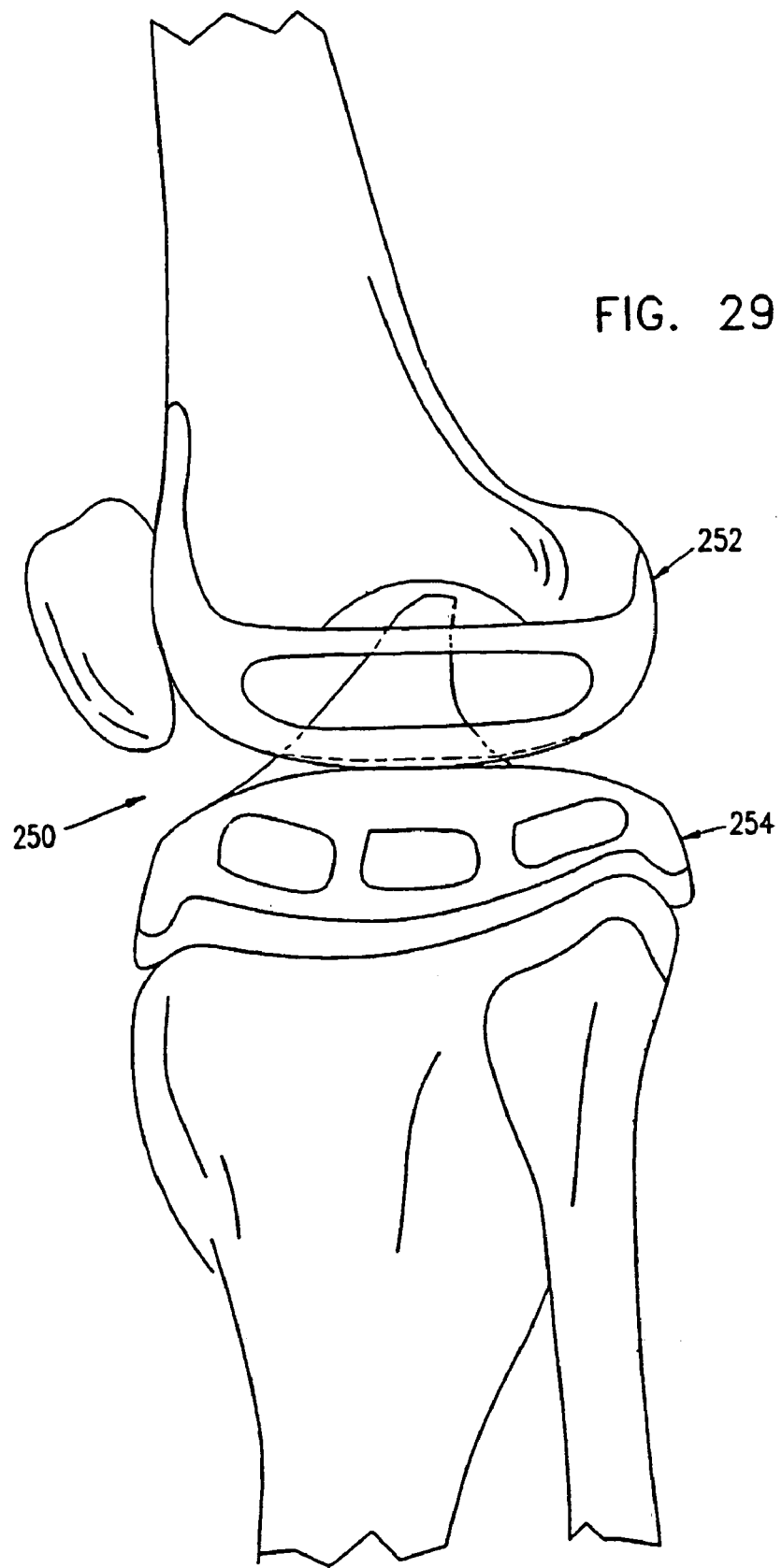
Figure 30:
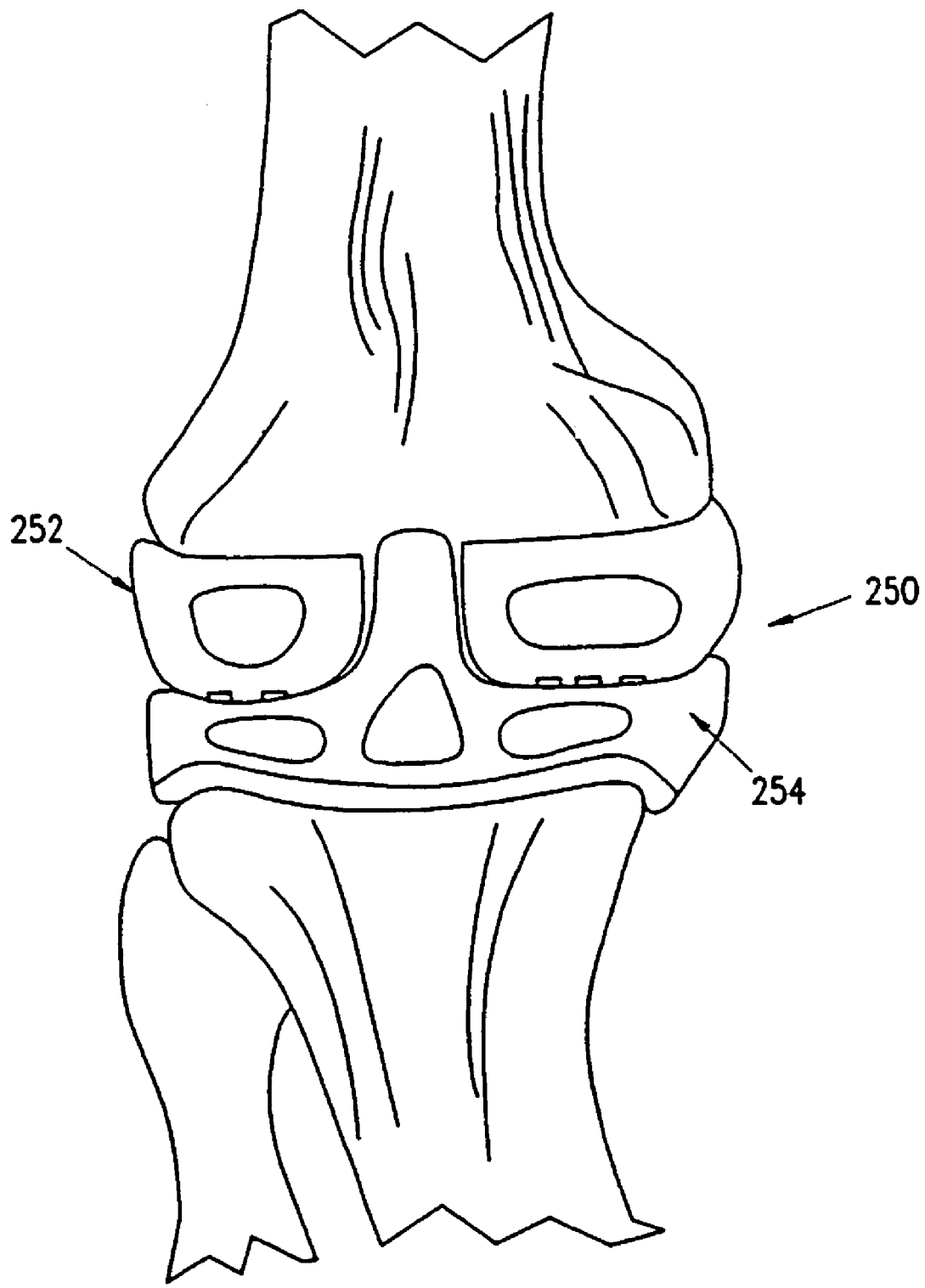
Figure 34:
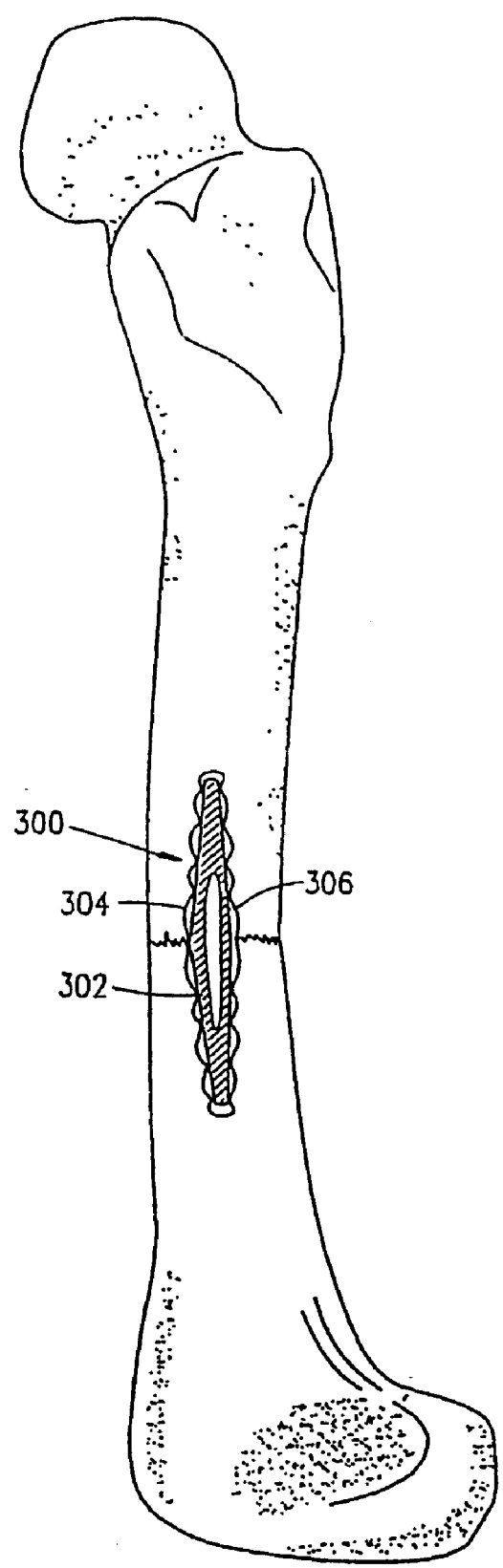
Figure 35:
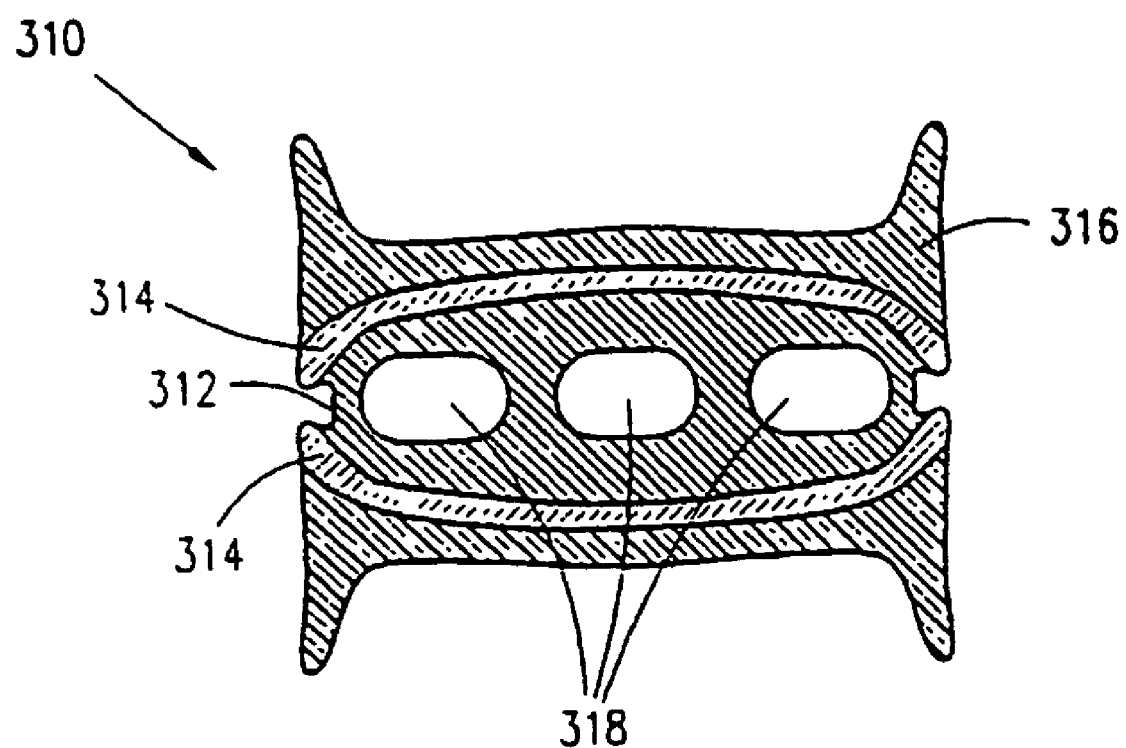

FIGS. 18A and 18B are simplified pictorial and sectional illustrations respectively of an artificial femoral head, constructed and operative in accordance with another preferred embodiment of the present invention, and wherein the femoral head comprises a plurality of alternating adjacent portions of substantially rigid and substantially resilient materials, FIG. 18B being taken along lines 18B-18B in FIG. 18A;

FIGS. 18C-18F are simplified pictorial illustrations of alternative constructions of a femoral head including a plurality of alternating adjacent-portions of substantially rigid and substantially resilient materials;

FIG. 18G is a simplified pictorial illustration of an artificial acetabulum, constructed and operative in accordance with a preferred embodiment of the present invention;

FIGS. 18H, 18I and 18J are simplified illustrations of installing the artificial acetabulum of FIG. 18G into a natural acetabulum, in accordance with a preferred embodiment of the present invention;

FIGS. 18K and 18L are simplified sectional illustrations of two artificial acetabula, constructed and operative in accordance with two preferred embodiments of the present invention;

FIGS. 19A-19C are simplified pictorial illustrations of a method of incision of ligaments, such as prior to insertion of a hip joint prosthesis, in accordance with a preferred embodiment of the present invention;

FIG. 20 is a simplified pictorial illustration of a sleeve for joining a femoral head with the innominate bone, constructed and operative in accordance with a preferred embodiment of the present invention;

FIG. 21 is a simplified sectional illustration of an expandable artificial femoral head, constructed and operative in accordance with a preferred embodiment of the present invention;

FIG. 22 is a simplified illustration of a human knee joint;

FIGS. 23 and 24 are respective simplified side and front view illustrations of a knee joint prosthesis, constructed and operative in accordance with a preferred embodiment of the present invention;

FIG. 25 is a simplified illustration of a femoral portion of the knee joint prosthesis of FIGS. 23 and 24;

FIG. 26 is a simplified illustration of a tibial portion of the knee joint prosthesis of FIGS. 23 and 24;

FIGS. 27 and 28 are respective simplified side and front view illustrations of a knee joint prosthesis, constructed and operative in accordance with another preferred embodiment of the present invention;

FIGS. 29 and 30 are respective simplified side and front view illustrations of a knee joint prosthesis, constructed and operative in accordance with yet another preferred embodiment of the present invention;

FIGS. 31 and 32 are respective simplified side and front view illustrations of a knee joint prosthesis, constructed and operative in accordance with still another preferred embodiment of the present invention;

FIG. 33 is a simplified illustration of a roller element included in the knee joint prosthesis of FIGS. 31 and 32;

FIG. 34 is a simplified, partially sectional illustration of a bone fastener, constructed and operative in accordance with a preferred embodiment of the present invention; and FIG. 35 is a simplified, partially sectional illustration of a vertebra replacement, constructed and operative in accordance with a preferred embodiment of the present invention.

The present invention will now be described in detail with respect to a prosthesis for an enarthrosis, an example being the hip joint, and to a prosthesis for a ginglymus, an example being the knee joint. It is appreciated, however, that a prosthesis for any true diarthrosis is in the scope of the present invention.

Figure 1:
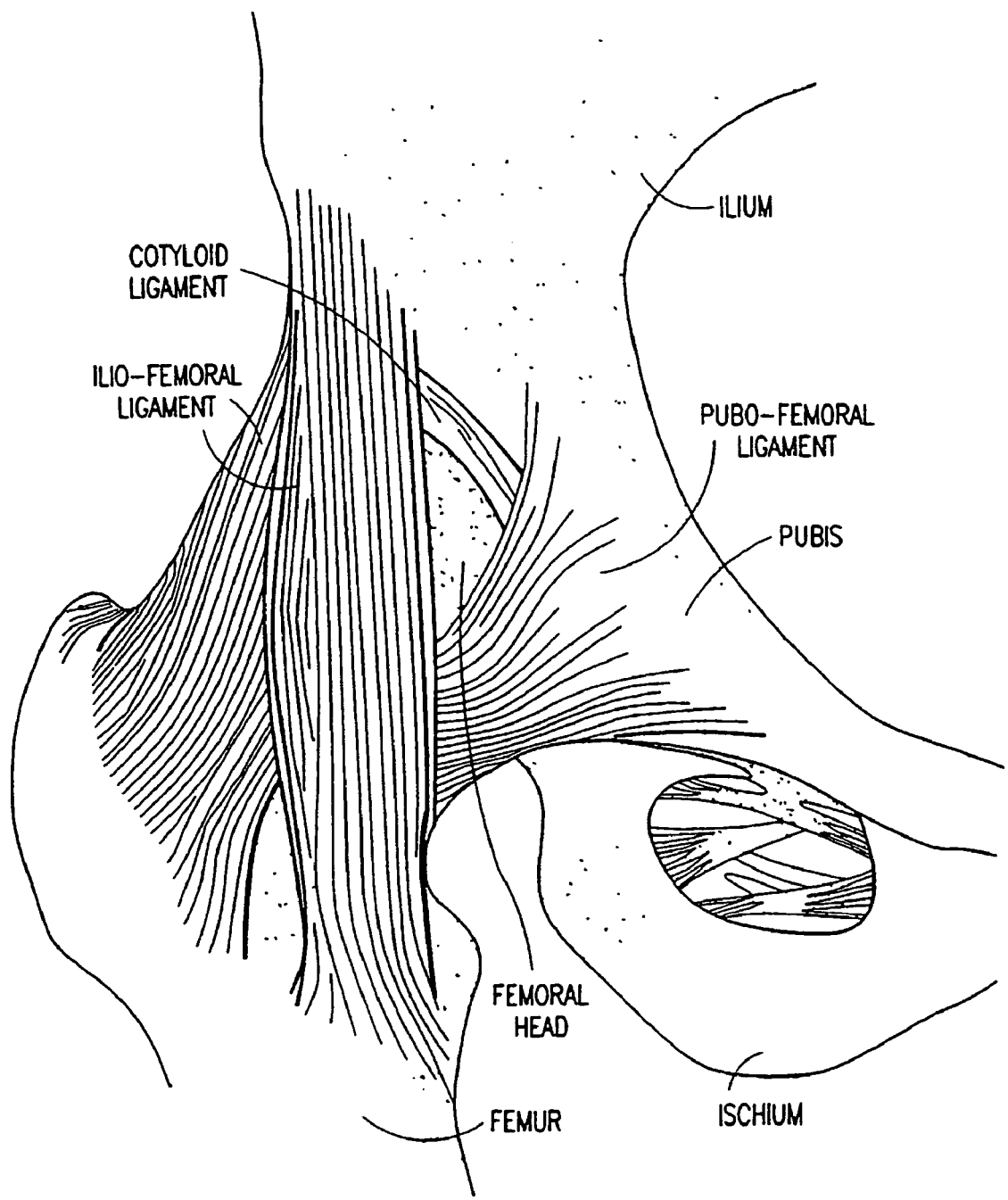
FIG. 1 is a simplified illustration of a human hip joint.

For a better understanding of a hip joint prosthesis, a basic description of the human hip joint is presented here with reference to FIG. 1, which illustrates the hip of the right side of the body. The hip joint is a ball and socket joint, the ball being the femoral head (head of the thigh bone) which articulates with the acetabulum of the innominate bone, known in nontechnical terms as the socket of the hip bone.

The innominate bone in the area of the hip joint is made of three portions: the upper portion is called the ilium, the middle portion is called the pubis and the lower portion is called the ischium. The femoral head is connected to the innominate bone by a plurality of ligaments. The ligaments shown in FIG. 1 are the iliofemoral ligaments and the pubofemoral ligament. There is also an ischio-femoral ligament, not seen in FIG. 1. The femoral head articulates with a fibrous rim of the acetabulum called the cotyloid ligament.

Generally a hip joint replacement of the prior art involves replacing the natural femoral head with a metallic artificial femoral head which is fixedly attached to a stem. The stem is generally inserted in the femur and the femoral head articulates with the acetabulum, if still intact, or some other depression, artificial or natural, in the innominate bone. Some or all of the illo-femoral, pubo-femoral and ischio-femoral ligaments may be removed to provide access to the femoral head and acetabulum.

Figure 2:
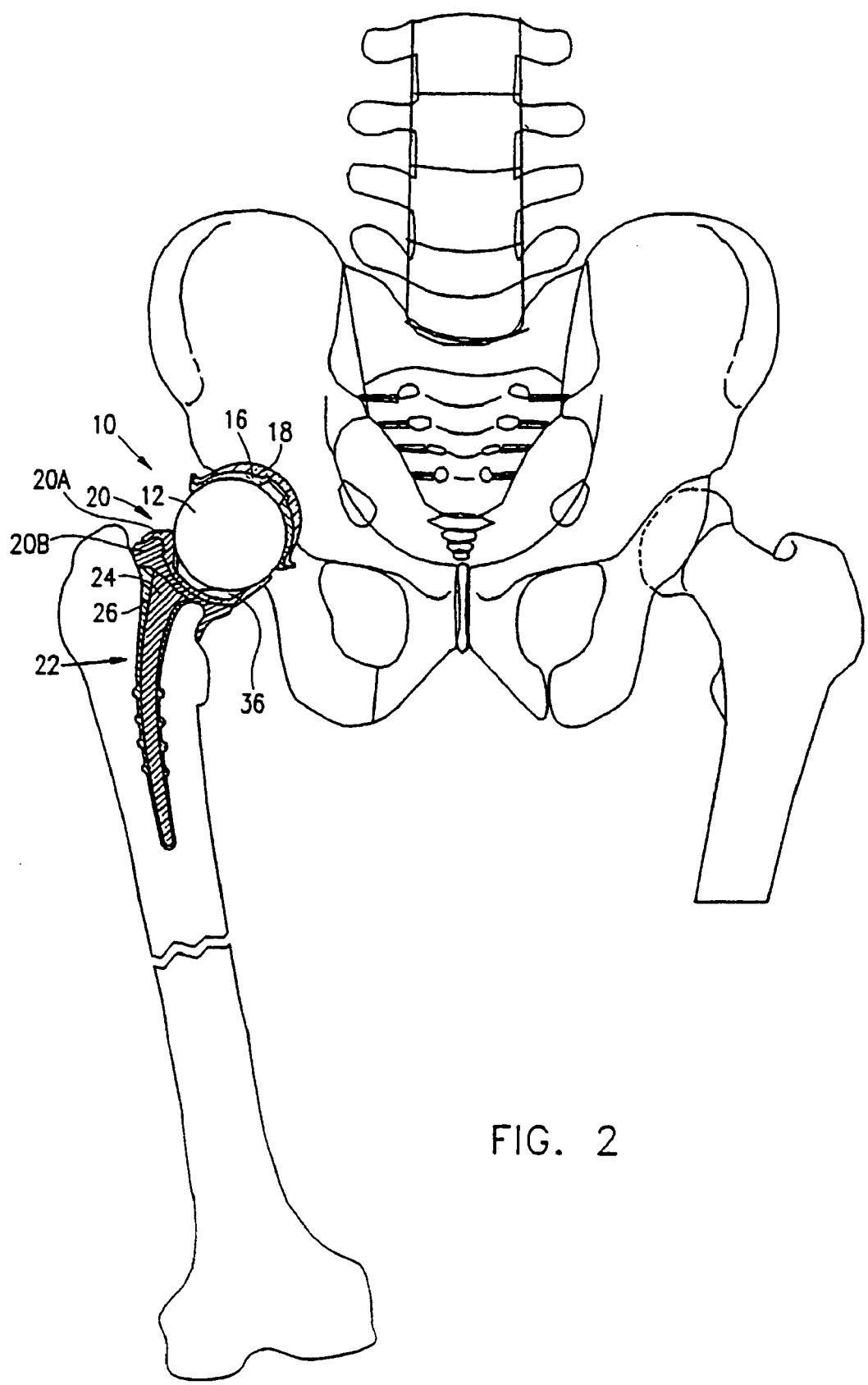
FIG. 2 is a simplified illustration of a hip joint prosthesis, constructed and operative in accordance with a preferred embodiment of the present invention.
Figure 3:
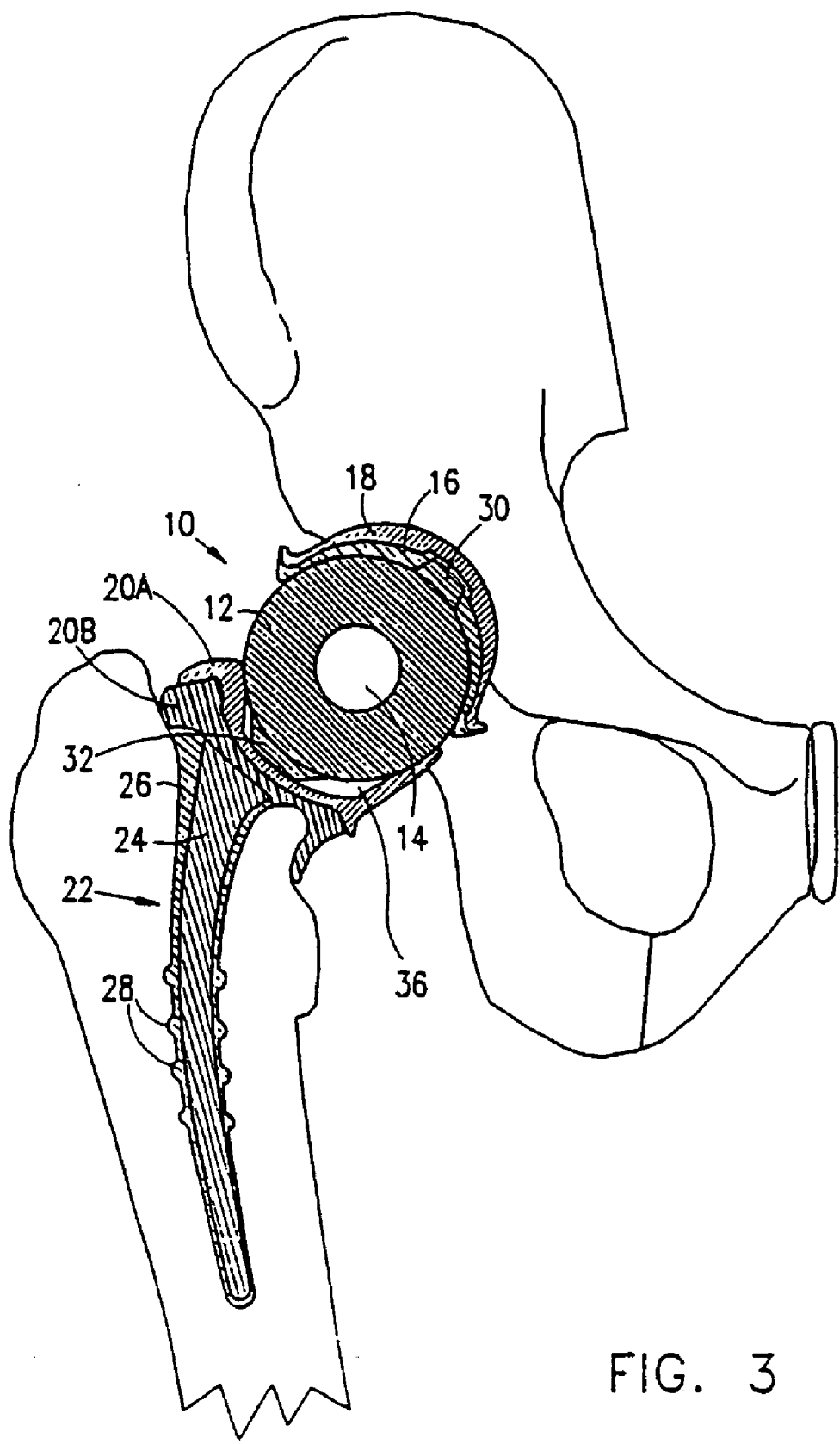
FIG. 3 is a partially sectional illustration of the hip joint prosthesis of FIG. 2.

Reference is now made to FIGS. 2 and 3 which illustrate a hip joint prosthesis 10, constructed and operative in accordance with a preferred embodiment of the present invention. In a radical departure from the prior art, hip joint prosthesis 10 comprises a femoral head 12 which is not fixedly attached to the femur, but rather is capable of articulating with both the thigh and the innominate bone. In accordance with a preferred embodiment of the present invention, femoral head 12 may be constructed of a rigid material compatible with human tissue, for example, a metal such as stainless steel, or a structural plastic.

In accordance with another preferred embodiment of the present invention, artificial femoral head 12 is constructed of a material which is shock absorbing, and additionally or alternatively provides damping, and additionally or alternatively is resilient. An example of such a material is polyurethane or synthetic rubber.

A resilient artificial femoral head, unlike the prior art, yields upon application of forces and substantially returns to its original shape after such forces are removed.

Artificial femoral head 12 is preferably, although not necessarily, generally spherical in shape. In accordance with a preferred embodiment of the present invention, and as shown in FIG. 3, femoral head 12 has a hollow core 14. Hollow core 14, inter alia, adds to the resiliency and shock absorbing characteristics of femoral head 12.

In accordance with a preferred embodiment of the present invention, hip joint prosthesis 10 also comprises an artificial acetabulum 16 which is preferably fixedly attached to the innominate bone via an acetabulum interface 18. Artificial femoral head 12 articulates with artificial acetabulum 16.

Additionally in accordance with a preferred embodiment of the present invention, hip joint prosthesis 10 comprises an artificial femoral socket 20 which is preferably fixedly attached to the femur via a stem 22. Alternatively, socket 20 may be attached to the femur without a stem, for example, by bonding. Artificial femoral head 12 articulates with artificial femoral socket 20. Socket 20 is shaped to facilitate this articulation, such as being generally concave. In addition, socket 20 is preferably shaped to overlap, or snugly fit, the upper portion of the natural femur. The generally concave, overlapping shape of artificial femoral socket 20 helps distribute stresses optimally on the femur, thereby stimulating regeneration of bone.

Socket 20 may overlap and "hug" the upper portion of the femur on the outside surface of the femur. Alternatively or additionally, socket 20 may be configured to fit snugly into an inner surface of the femur.

It is important to note that socket 20 serves two general tasks, as described above. The first task is articulation with artificial femoral head 12. The second task is fitting snugly with the femur and distributing stresses evenly thereon.

It is appreciated that in accordance with another preferred embodiment of the present invention, socket 20 may comprise two separate portions each generally dedicated to serving one of the above described tasks. A first portion 20A, generally concave in shape, may be generally dedicated to articulation with artificial femoral head 12. A second portion 20B, generally shaped as a "crown" to hug and snugly fit circumferentially aground and on top of the femur, may be generally dedicated to distributing stresses evenly on the femur. This is true of any of the sockets described herein with reference to any of the embodiments of the present invention. The "crown", i.e., second portion 20B, greatly changes the loading conditions of prosthesis 10, decreases stresses exerted on the femur by stem 22, and creates a new and healthier stress distribution on the surrounding bone and tissue. With the support of second portion 20B, stem 22 may have a much smaller section throughout and particularly at its neck.

Stem 22 preferably includes a core 24 and an outer layer 26, as seen in FIGS. 2 and 3. Outer layer 26 preferably includes one or more ridges 28, which, inter alia, help distribute stresses and help fasten stem 22 to the femur.

Core 24 of stem 22, artificial acetabulum 16 and artificial femoral socket 20 are preferably constructed of a rigid material, for example, stainless steel or a structural plastic. Alternatively, the rigid material may be a composite material, such as a lay-up of graphite fibers, which may be constructed to have mechanical or physical properties, such as modulus of elasticity or coefficient of thermal expansion, equivalent to that of the local human bone.

Stem 22 provides excellent three-dimensional anchorage to the bone, and induces three-dimensional loading stress conditions as close as possible to the natural conditions. The improved stress field distribution at the interface between the prosthesis and the bone helps prevent lysis. The stress field set up by the prosthesis inside the bone helps induce regeneration and strengthening of the bone.

Acetabulum interface 18 and outer layer 26 of stem 22 are preferably made of a resilient material compatible with human tissue, such as polyurethane, which helps distribute stresses optimally, thereby stimulating regeneration of bone. In accordance with a preferred embodiment of the present invention, acetabulum interface 18 and outer layer 26 of stem 22 are constructed of a material, such as polyurethane, which has one or more mechanical and/or physical properties substantially similar to human cartilage.

Hip joint prosthesis 10 may include a device for facilitating removal as is known in the art, such as a threaded boss or hole (both not shown).

It may sometimes be desired to limit the number of degrees of freedom of the hip joint or the range of a particular degree of freedom of movement of the femur with respect to the acetabulum, depending on the needs of the patient. It may also be desired to provide safeguards to substantially prevent dislocation of the joint. In accordance with a preferred embodiment of the present invention, apparatus is provided to achieve these goals, as is now described.

Figure 4:
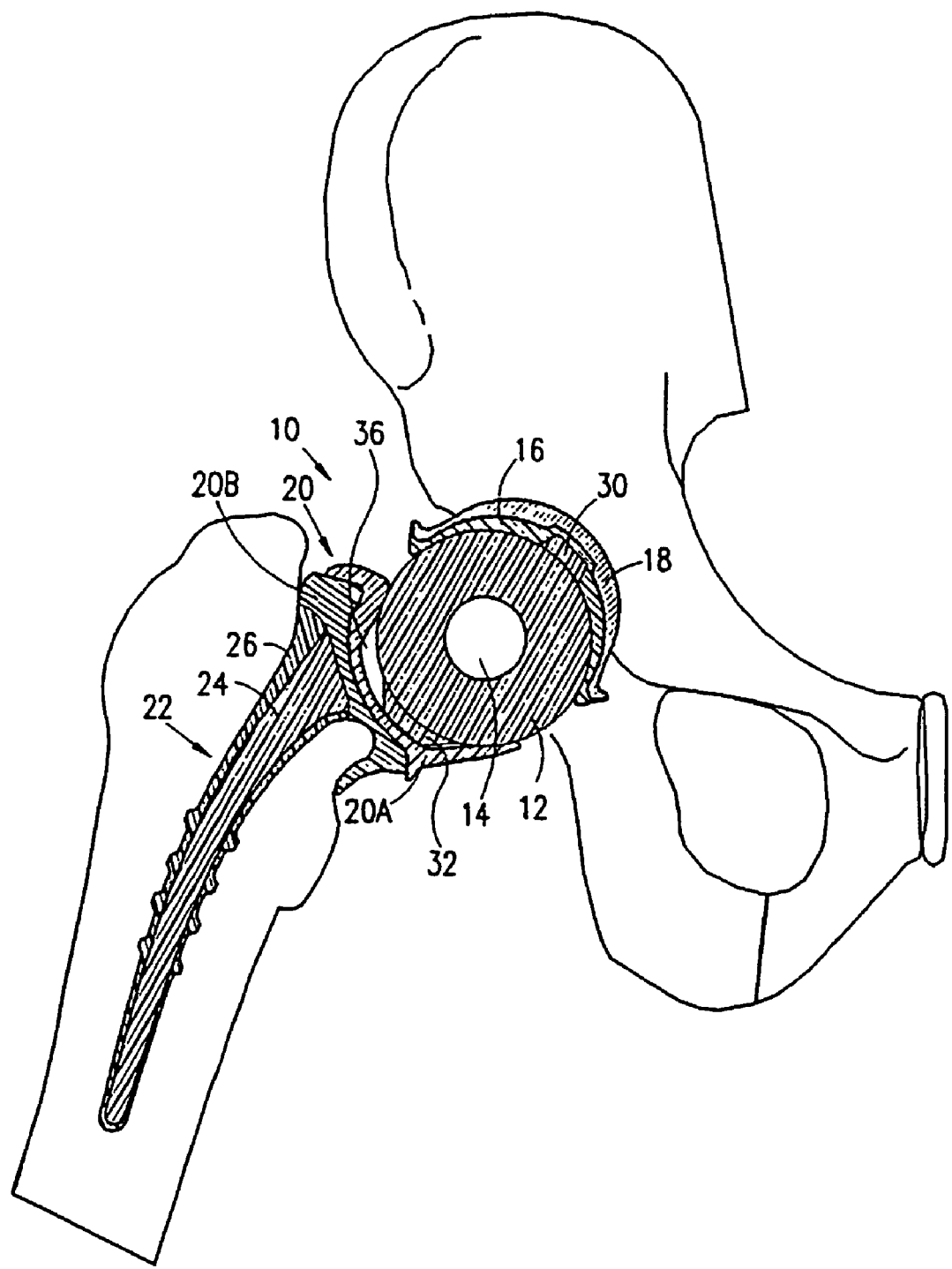
FIG. 4 is a partially sectional illustration of the hip joint prosthesis of FIG. 2, wherein the femur is rotated laterally.
Figure 5:
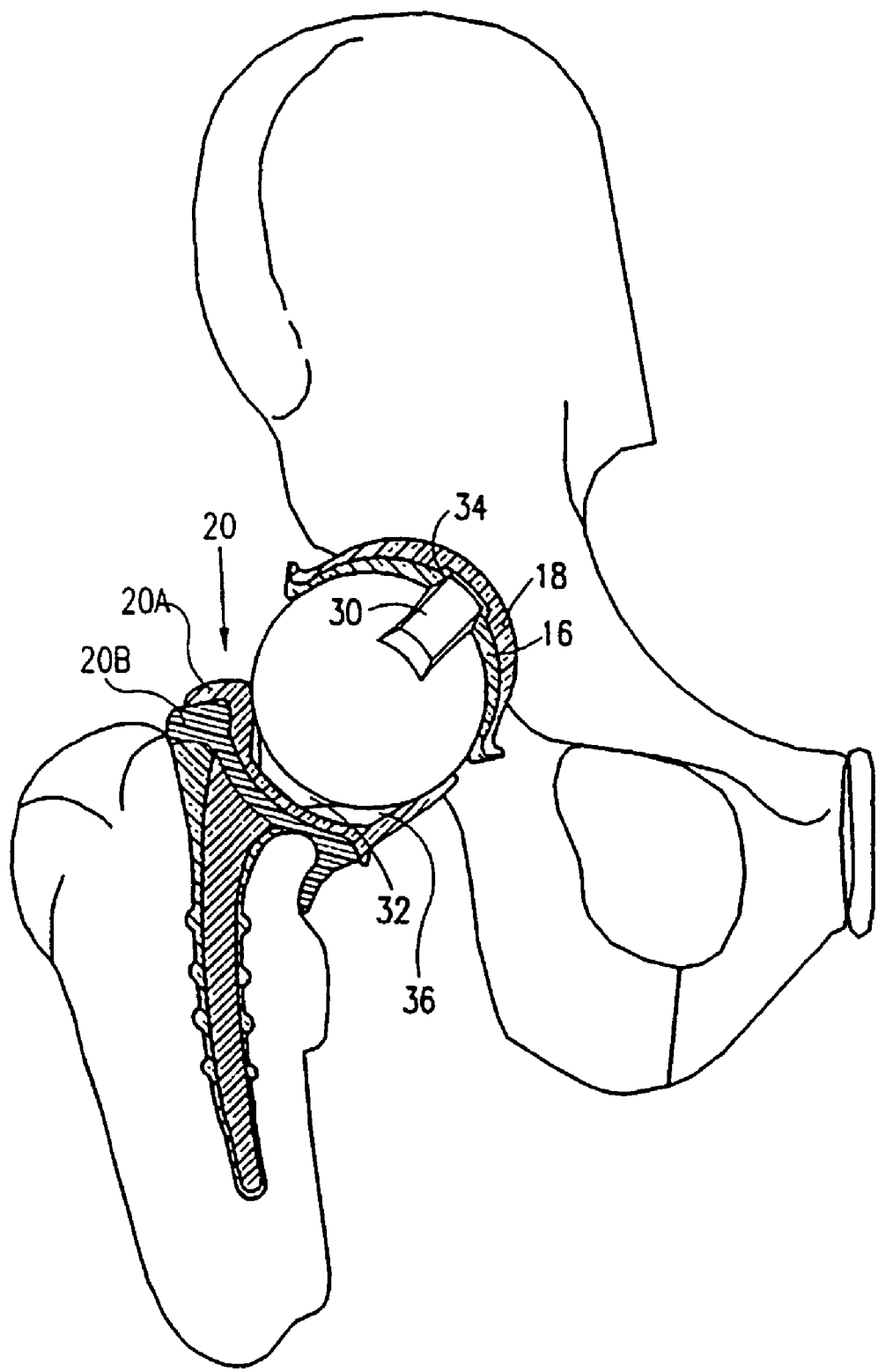
FIG. 5 is a partially sectional illustration of the hip joint prosthesis of FIG. 2, wherein the femur is rotated rearwardly.
Figure 6:
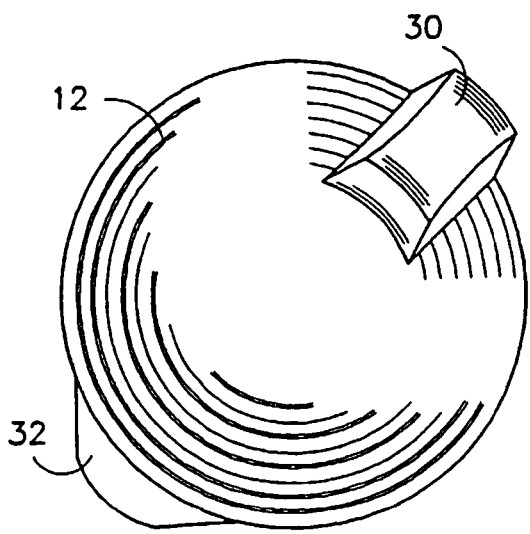
FIG. 6 is a simplified pictorial illustration of an artificial femoral head of the hip joint prosthesis of FIG. 2, the femoral head comprising two delimiting rails.

Reference is now made additionally to FIGS. 4-6. In accordance with a preferred embodiment of the present invention, artificial femoral head 12 is provided with an upper delimiting rail 30 and a lower delimiting rail 32. Upper delimiting rail 30 slides in a channel 34 in artificial acetabulum 16. Channel 34 is oriented generally forwards and rearwards with respect to the human body. As seen in FIG. 5, upper delimiting rail 30 slides forwards in channel 34 when the femur is moved backwards. It is appreciated that upper delimiting rail 30 slides backwards in channel 34 when the femur is moved forwards.

Lower rail 32 slides in a channel 36 in artificial femoral socket 20. As seen in FIG. 4, as the femur is moved laterally away from the body, lower rail 32 slides in channel 36 of socket 20 and butts thereagainst. Upper delimiting rail 30 is similarly constrained to slide in channel 34. Constraining the travel of rails 30 and 32 in channels 34 and 36, respectively, substantially prevents overtravel of the femur and substantially prevents dislocation of artificial femoral head 12 from artificial acetabulum 16 and artificial femoral socket 20. Moreover, since femoral head 12 is preferably constructed of a shock absorbing or resilient material, the butting of rails 30 and 32 against channels 34 and 36, respectively, is substantially cushioned and damped.

Figure 7A:
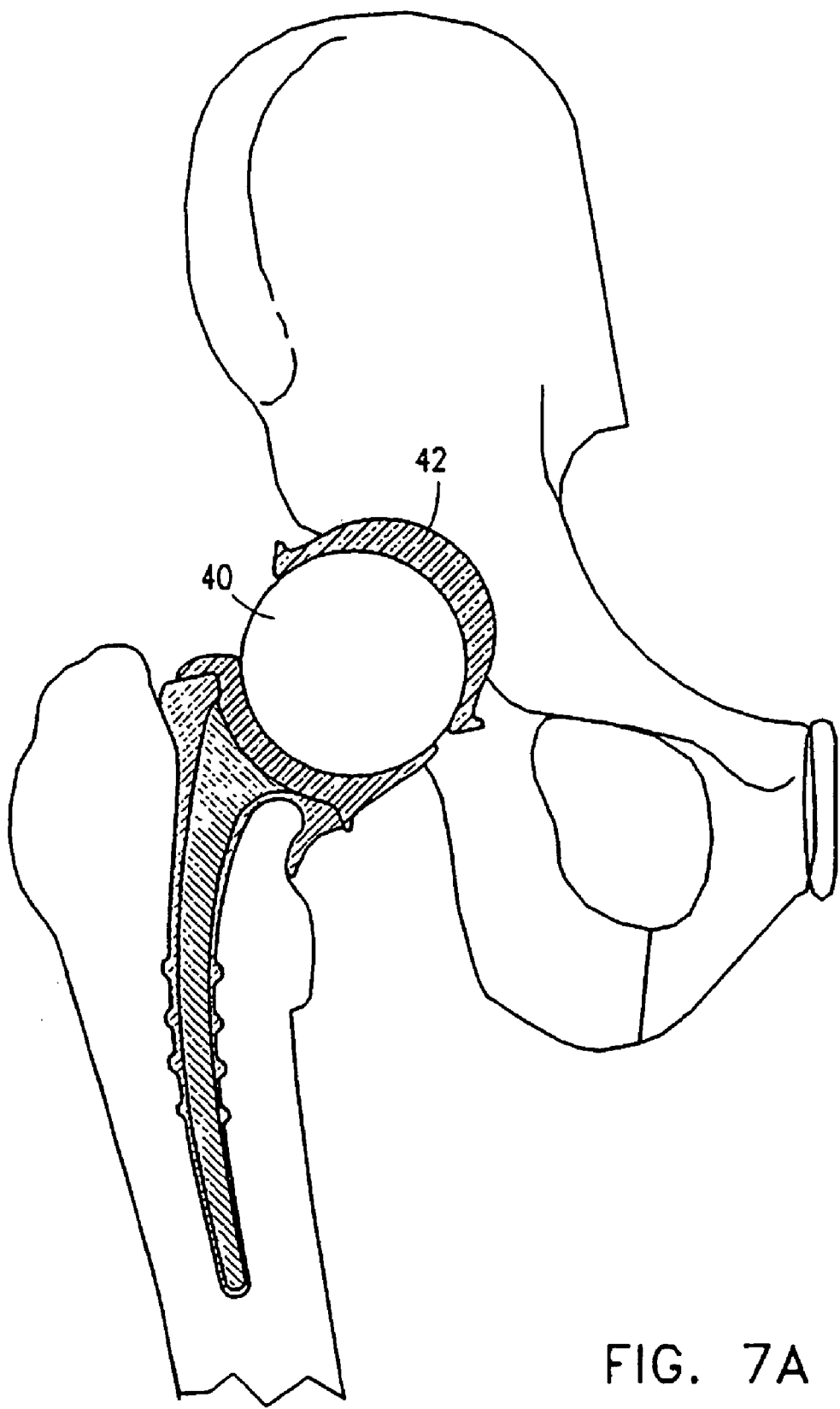
FIGS. 7A and 7B are simplified illustrations of an artificial femoral head, constructed and operative in accordance with another preferred embodiment of the present invention, articulating with artificial and natural acetabula respectively, and wherein the artificial femoral head has no delimiting rails.
Figure 7B:
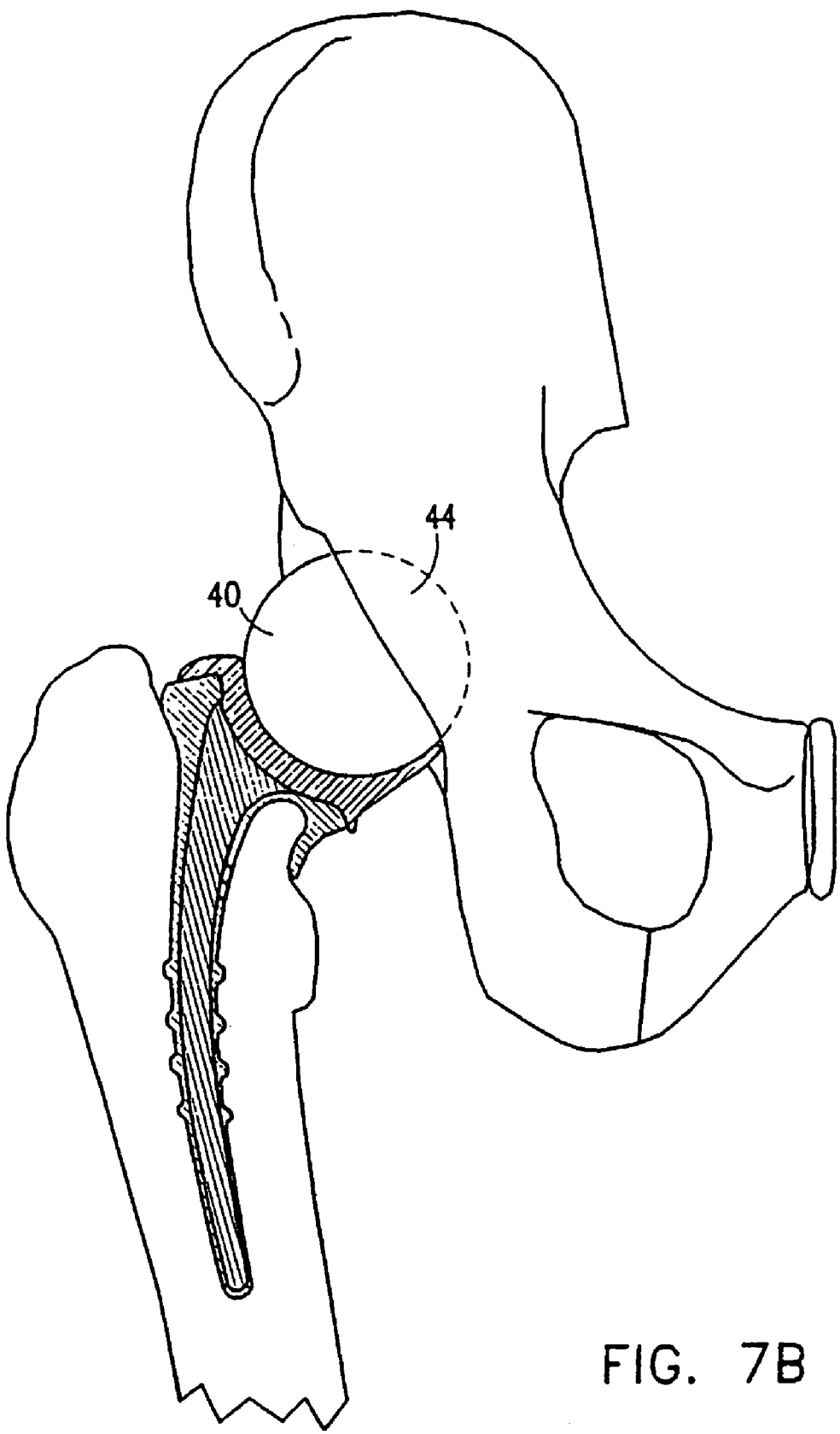

Variations of hip joint prosthesis 10 are possible within the scope of the present invention. Reference is now made to FIGS. 7A and 7B which illustrate an artificial femoral head 40, constructed and operative in accordance with another preferred embodiment of the present invention. Artificial femoral head 40 may be similar in construction and operation to artificial femoral head 12 or FIGS. 2-6. Femoral head 40 differs from femoral head 12 in that femoral head 40 has no delimiting rails. In FIG. 7A, femoral head 40 is shown articulating with an artificial acetabulum 42. In FIG. 7S, femoral head 40 is shown articulating with a natural acetabulum 44.

Figure 8A:
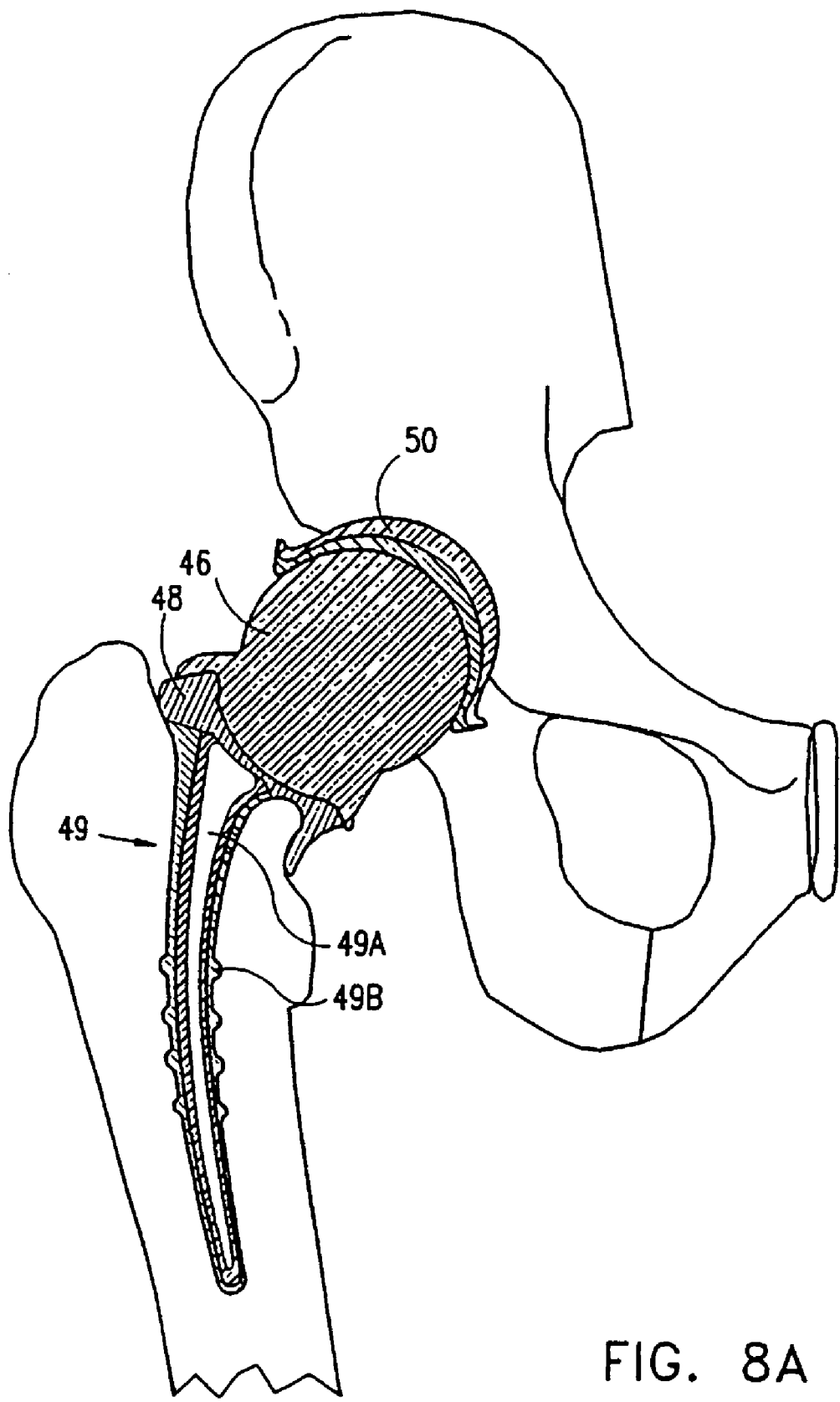
FIGS. 8A and 8B are simplified illustrations of an artificial femoral head fixedly attached to a stem, constructed and operative in accordance with yet another preferred embodiment of the present invention, articulating with artificial and natural acetabula respectively, and wherein the artificial femoral head has no delimiting rails.
Figure 8B:
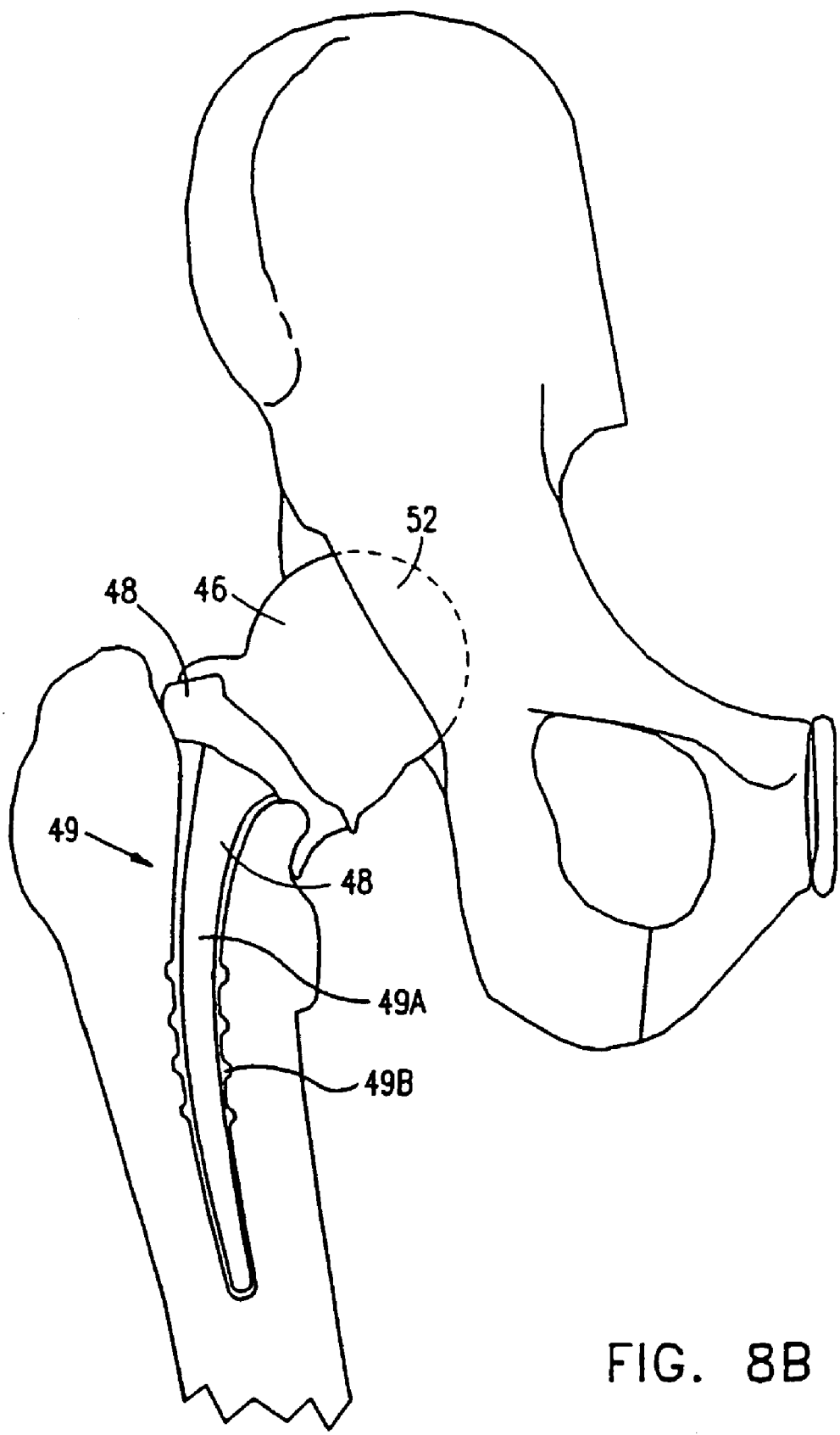

Reference is now made to FIGS. 8A and 8B which illustrate an artificial femoral head 46 fixedly attached to a crown 48, constructed and operative in accordance with yet another preferred embodiment of the present invention. Femoral head 46 and crown 48 may be constructed of a resilient material, such as polyurethane.

Crown 48 may be attached to an upper portion of the thigh. Alternatively, as shown in FIG. 8A, crown 48 may be attached to a stem 49. Stem 49 may include a core 49A and an outer layer 49B. Core 49A may be of solid construction, and additionally or alternatively, may include at least one hollow portion. Outer layer 49B may be constructed of a material with properties similar to human cartilage.

In FIG. 8A, femoral head 46 articulates with an artificial acetabulum 50. Femoral head 46 may have an upper delimiting rail (not shown) which articulates with a corresponding groove (not shown) in artificial acetabulum 50. Alternatively, femoral head 46 may have a delimiting groove with which articulates a corresponding rail in artificial acetabulum 50.

In FIG. 8B, femoral head 46 articulates with a natural acetabulum 52. Femoral head 46 may include a hollow portion (not shown), as described hereinabove for artificial femoral head 12 with respect to FIGS. 2-6.

Alternatively, in accordance with another preferred embodiment of the present invention, artificial femoral head 46 may be fixedly attached to artificial acetabulum 50. In such an embodiment, artificial femoral head 46 may articulate with crown 48.

Figure 8C:
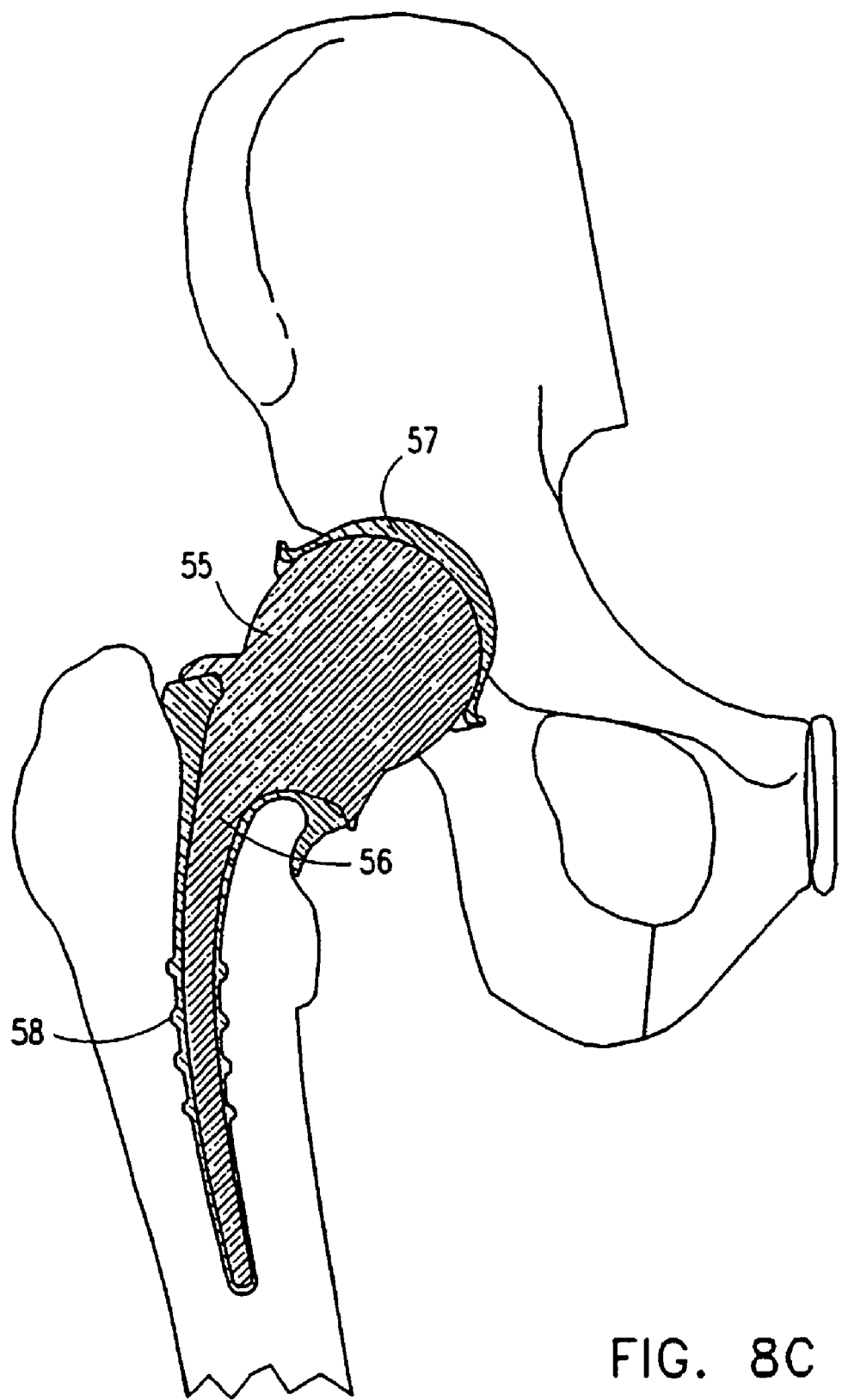
FIG. 8C is a simplified illustration of an artificial, self-articulating femoral head fixedly attached to a stem and to an acetabulum, constructed and operative in accordance with a preferred embodiment of the present invention.

Reference is now made to FIG. 8C which illustrates an artificial, self-articulating femoral head 55 fixedly attached to a stem 56 and to an artificial acetabulum 57, constructed and operative in accordance with a preferred embodiment of the present invention. Femoral head 55 is preferably constructed of a resilient material, such as polyurethane. Artificial acetabulum 57 may have any suitable shape, typically being generally shell shaped or spherical.

Articulation of the thigh with the innominate bone is not achieved by articulation of femoral head 55 with artificial acetabulum 57, but rather is achieved by the self-articulation of femoral head 55. "Self-articulation" is defined as the ability of femoral head 55 to permit rotary and translatory motion of the thigh with respect to the innominate bone due to the resilient and elastic properties and configuration of femoral head 55. Stem 56 may comprise an outer layer 58 which may have properties similar to human cartilage.

Figure 9B:
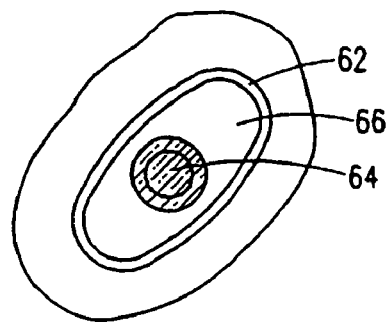
FIG. 9B is a simplified sectional illustration of the femoral head of FIG. 9A, taken along lines 9B-9B in FIG. 9A.
Figure 9A:
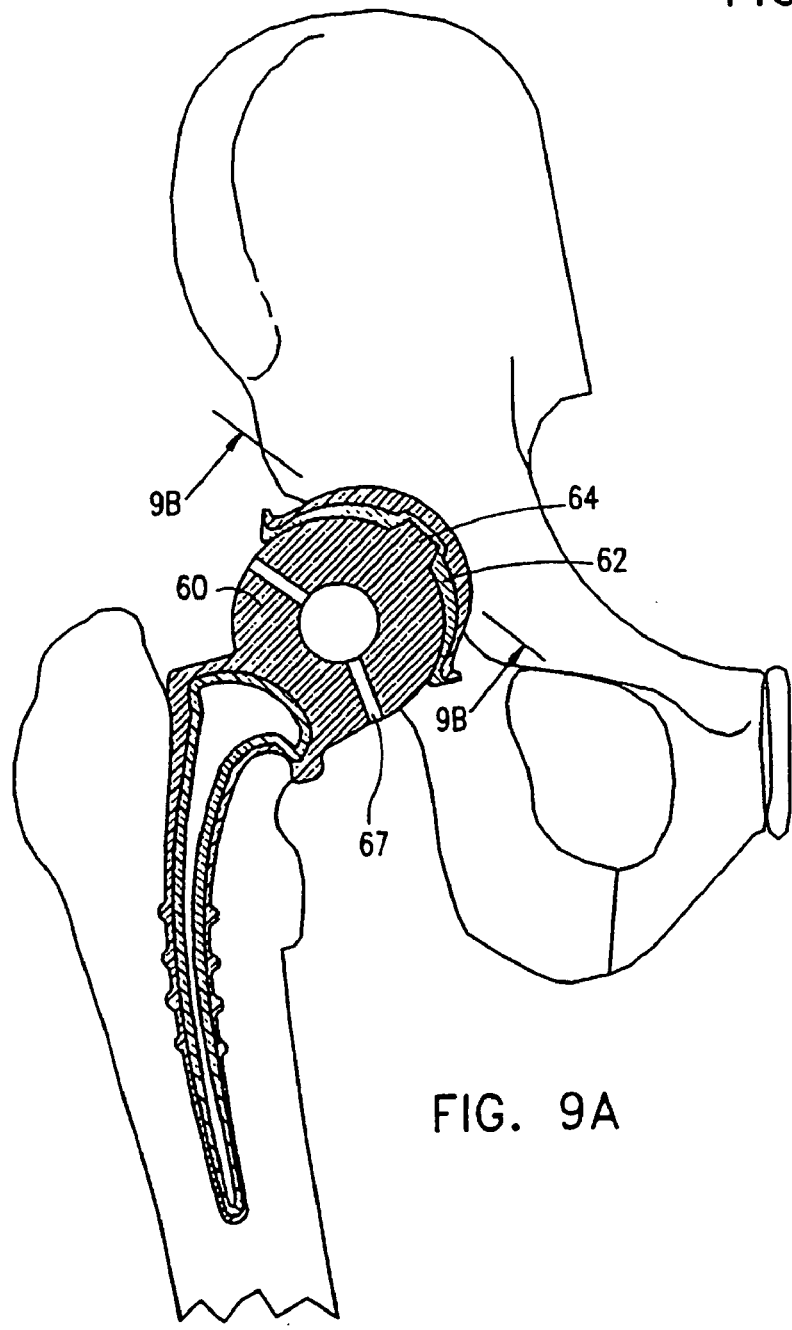
FIG. 9A is a simplified pictorial illustration of an artificial femoral head and an artificial acetabulum, constructed and operative in accordance with still another preferred embodiment of the present invention, and wherein the artificial femoral head has one delimiting rail which articulates with the generally elliptically shaped acetabulum.

Reference is now made to FIGS. 9A and 9B which illustrate an artificial femoral head 60 and an artificial acetabulum 62, constructed and operative in accordance with still another preferred embodiment of the present invention. Artificial femoral head 60 has one delimiting rail 64 which articulates with a generally elliptically shaped recess 66 in artificial acetabulum 62. It is appreciated that this type of rail may be employed in any of the other artificial femoral heads described herein, either as an upper rail or a lower rail or both.

Artificial femoral head 60 may be provided with one or more fluid passageways 67, as seen in FIG. 9A, for flow therethrough of a fluid (not shown), such as synovial fluid. It is appreciated that any of the artificial femoral heads of the present invention may be provided with fluid passageways. Fluid passageways 67 help lubricate artificial femoral head 60, and provide damping.

Figure 9C:
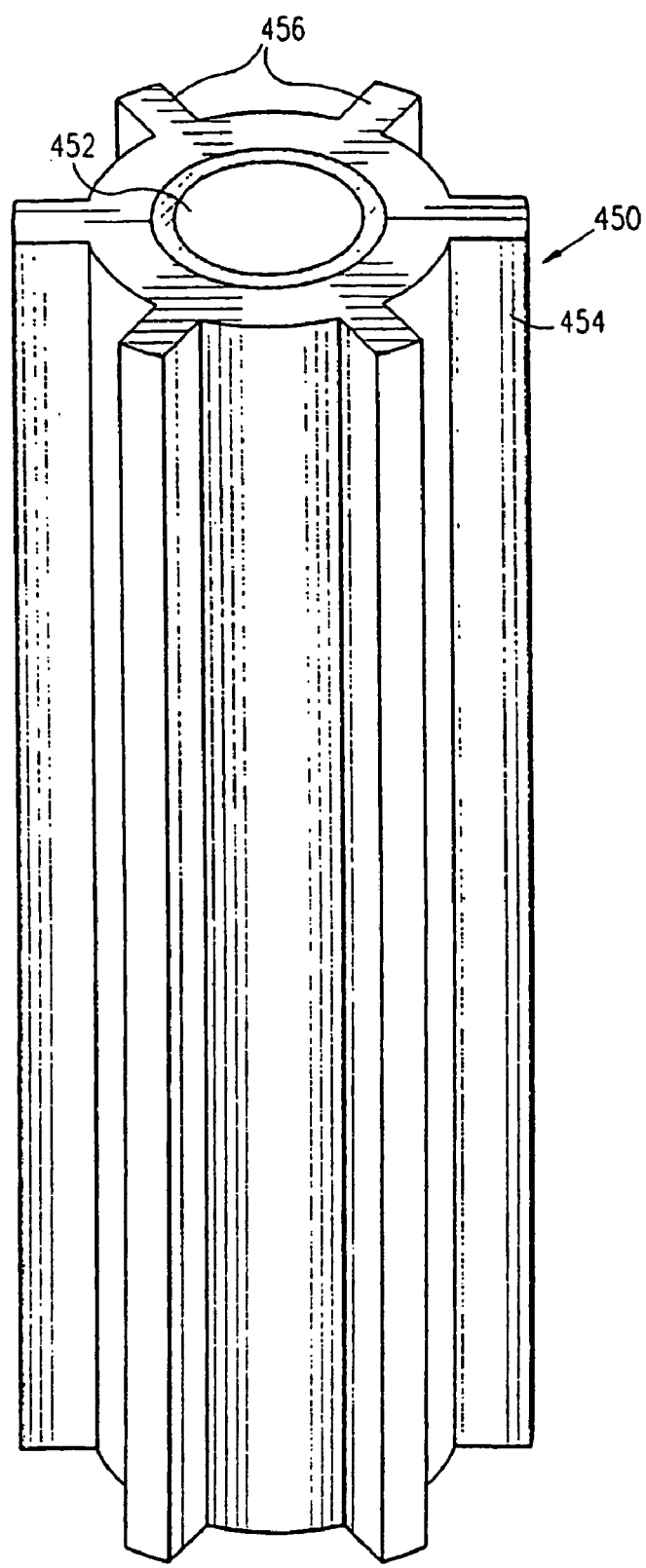
FIG. 9C is a simplified pictorial illustration of a flexible and stable bone connector, constructed and operative in accordance with a preferred embodiment of the present invention.

Reference is now made to FIG. 9C which illustrates a flexible and stable bone connector 450, constructed and operative in accordance with a preferred embodiment of the present invention. Connector 450 preferably includes a hollow, generally tubular portion 452 and a bone interface portion 454. Interface portion 454 is preferably shaped to snugly fit the inner geometry of the bone into which it is placed. The inner geometry of the bone may be determined by such methods as a computer tomography, and interface portion 454 may then be machined accordingly.

In accordance with a preferred embodiment of the present invention, interface portion 454 has a fluted shape with a plurality of protruding fins 456. The fluted shape of interface portion 454 and the hollowness of tubular portion 452 promote bone development and growth after implanting the prosthesis. Connector 450 may be fashioned in a variety of configurations, such as straight, curved, cylindrical or tapered, for example.

A known problem associated with the repair of broken bones and with the insertion of stems of femoral prostheses into femurs, is that the bone may have a curvature which changes along the length thereof in three dimensions. It is difficult to match the curvature of the stem of the prosthesis to the natural curvature of the bone. In practice, usually a set of standardized connecting pins or prostheses are used and the closest matching prosthesis is selected and further machined or filed in the operating theater to match the measured natural curvature of the femur. Even with this method, gaps are almost inevitable between the prosthesis and the inner bone tissue.

It is a particular feature of the present invention that connector 450 is sufficiently flexible so that it can be inserted into a bored portion of the bone, such as a femur, and deform to adapt to the changing curvature of the bone, thereby helping to solve the aforementioned problem. Connector 450 is preferably constructed of a material which provides flexibility to permit insertion into the bone, while at the same time providing sufficient structural stability once connector 450 is in place. A suitable material is one having a non-linear, "half-bell-shaped" stress-strain relationship, for example, a plastic such as polyurethane. The material may be reinforced with fibers, whose density and orientation may be selected in accordance with a particular engineering requirement.

Figure 9D:
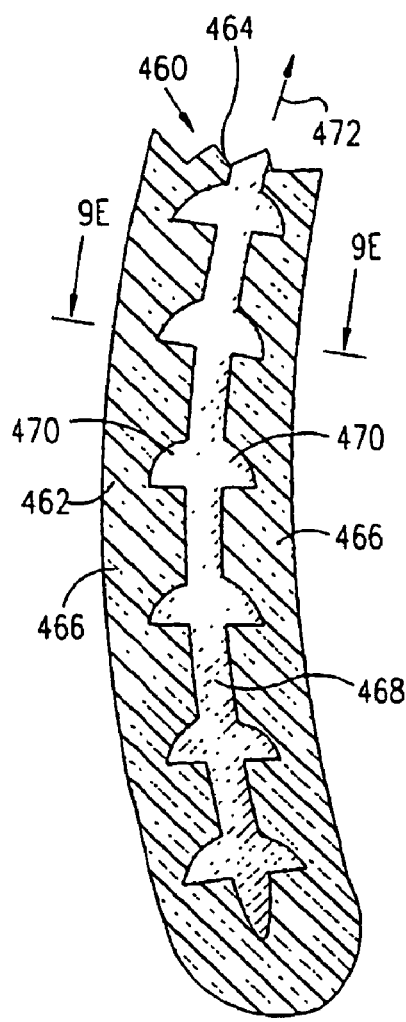
FIGS. 9D and 9E are simplified, sectional illustrations of a flexible and stable bone connector stem of a hip joint prosthesis, constructed and operative in accordance with a preferred embodiment of the present invention, before and after deployment, respectively.
Figure 9E:
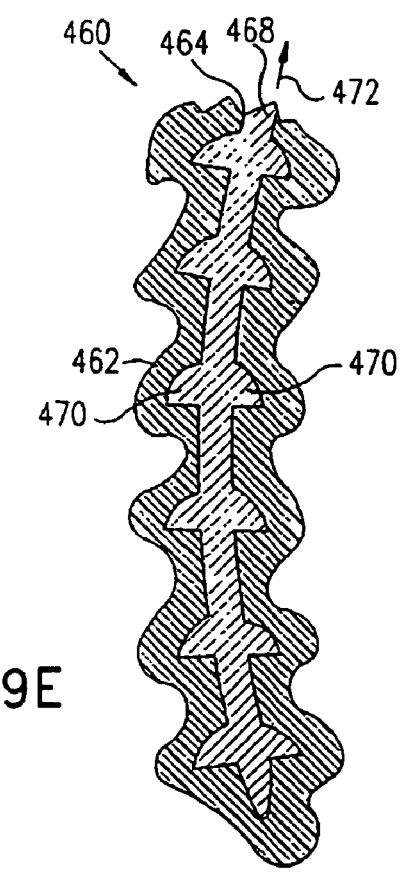

Reference is now made to FIGS. 9D and 9E which illustrate a flexible and stable bone connector stem 460 of a hip joint prosthesis, constructed and operative in accordance with a preferred embodiment of the present invention. Stem 460 may be readily employed in any of the femoral prostheses of the present invention.

Stem 460 is preferably constructed similarly to connector 450, and preferably includes a fluted elongated portion 462 having a hollow portion 464 and a plurality of protruding fins 466. A force transfer element 468, such as a wire, rod or cable, with a plurality of bulges 470 is preferably disposed in hollow portion 464. Element 468 may be made of any suitable stiff, biocompatible material, such as DYNEEMA.

Stem 460 is preferably inserted into the femur in the orientation shown in FIG. 9D. After insertion, element 468 is then moved generally in the direction of an arrow 472, thereby causing bulges 470 to deform fluted portion 462, as seen in FIG. 9D, and fix stem 460 firmly in the femur.

Figure 9F:
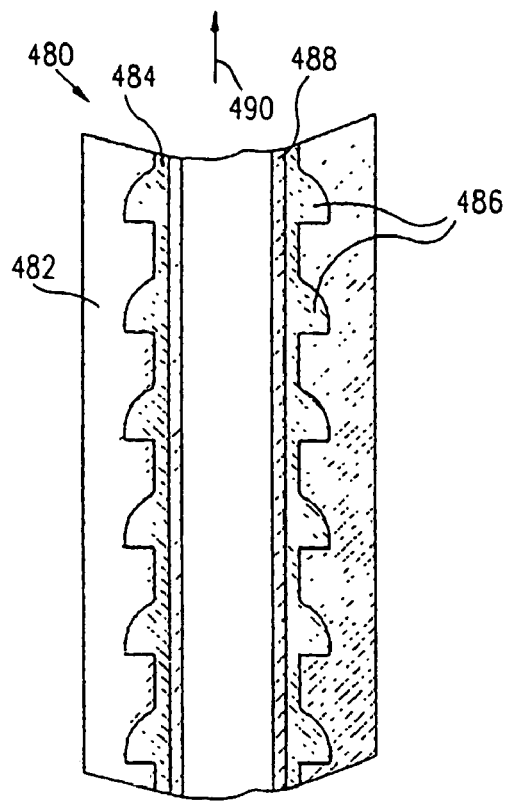
FIGS. 9F and 9G are simplified, sectional illustrations of a flexible and stable bone connector stem of a hip joint prosthesis, constructed and operative in accordance with another preferred embodiment of the present invention, before and after deployment, respectively.
Figure 9G:
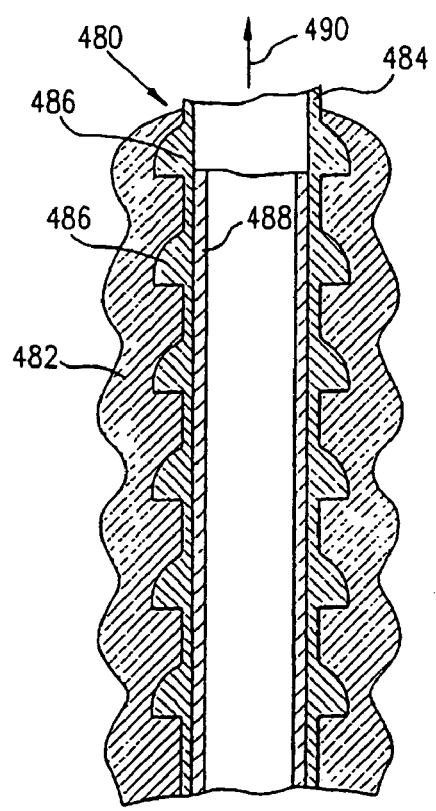

Reference is now made to FIGS. 9F and 9G which illustrate a flexible and stable bone connector stem 480 of a hip joint prosthesis, constructed and operative in accordance with another preferred embodiment of the present invention. Stem 480 may also be readily employed in any of the femoral prostheses of the present invention.

Stem 480 preferably includes a fluted elongated portion 482 in which is disposed a sleeve 484 having a plurality of bulges 486. Disposed inside sleeve 484 is hollow shaft 488. Sleeve 484 is arranged for sliding, axial motion with respect to fluted portion 482 and shaft 488.

As describe hereinabove for fluted portion 462, fluted portion 482 is sufficiently flexible so that it can be inserted into a bored portion of a femur and deform to adapt to the changing curvature of the femur.

Stem 480 is preferably inserted into the femur in the orientation shown in FIG. 9F. After insertion, sleeve 484 is then moved generally in the direction of an arrow 490, thereby causing bulges 486 to deform fluted portion 482, as seen in FIG. 9D, and fix stem 480 firmly in the femur.

Figure 10:
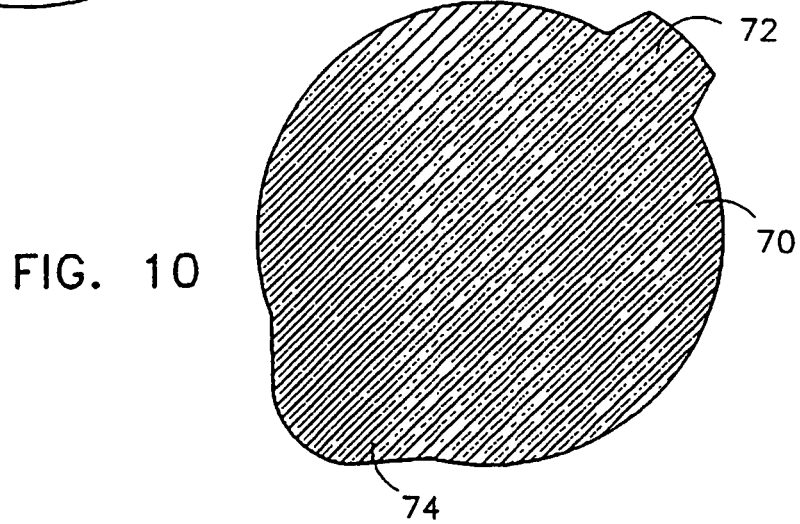
FIG. 10 is a simplified sectional illustration of a non-hollow artificial femoral head, constructed and operative in accordance with a preferred embodiment of the present invention.

Artificial femoral head 12 shown in FIGS. 2-6, has a hollow core 14. Reference is now made to FIG. 10 which illustrates a non-hollow artificial femoral head 70, constructed and operative in accordance with a preferred embodiment of the present invention. Artificial femoral head 70 may include an upper rail 72 and a lower rail 74.

Figure 11:
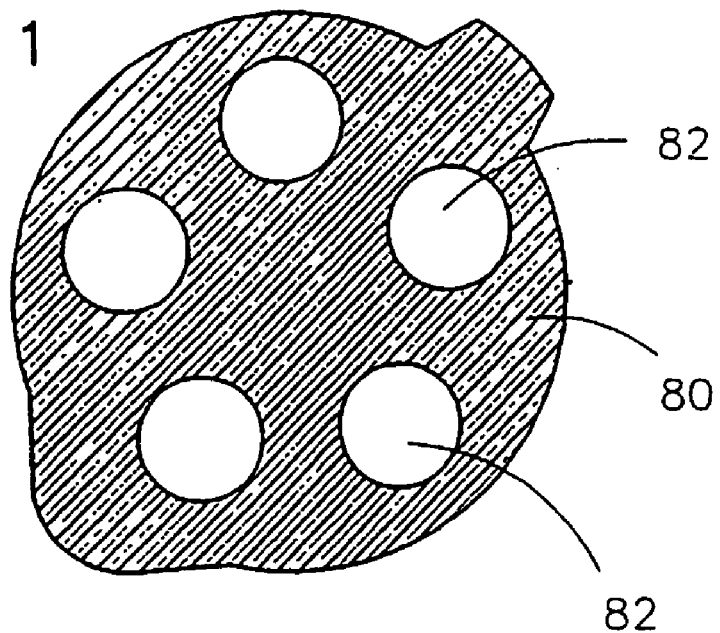
FIG. 11 is a simplified sectional illustration of an artificial femoral head, constructed and operative in accordance with another preferred embodiment of the present invention, and wherein the femoral head comprises a plurality of hollow portions.

Reference is now made to FIG. 11 which illustrates an artificial femoral head 80, constructed and operative in accordance with another preferred embodiment of the present invention. Femoral head 80 comprises a plurality of hollow portions 82.

Figure 12:
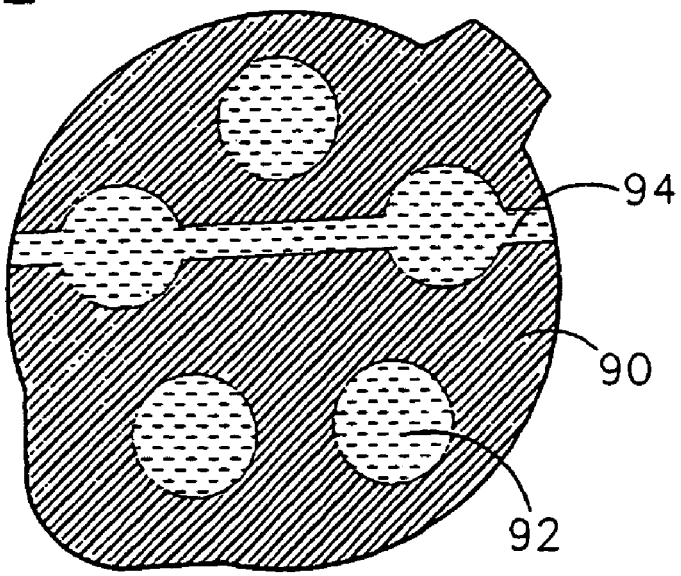
FIG. 12 is a simplified sectional illustration of an artificial femoral head, constructed and operative in accordance with yet another preferred embodiment of the present invention, and wherein the femoral head comprises a plurality of hollow portions filled with a fluid.

Reference is now made to FIG. 12 which illustrates an artificial femoral head 90, constructed and operative in accordance with yet another preferred embodiment of the present invention. Femoral head 90 comprises a plurality of hollow portions 92 filled with a fluid, such as synovial fluid. Additionally or alternatively, one or more fluid passageways 94 may be provided. The fluid in portions 92 or passageways 94 may enhance the shock absorbing and damping characteristics of femoral head 90.

Figure 13:
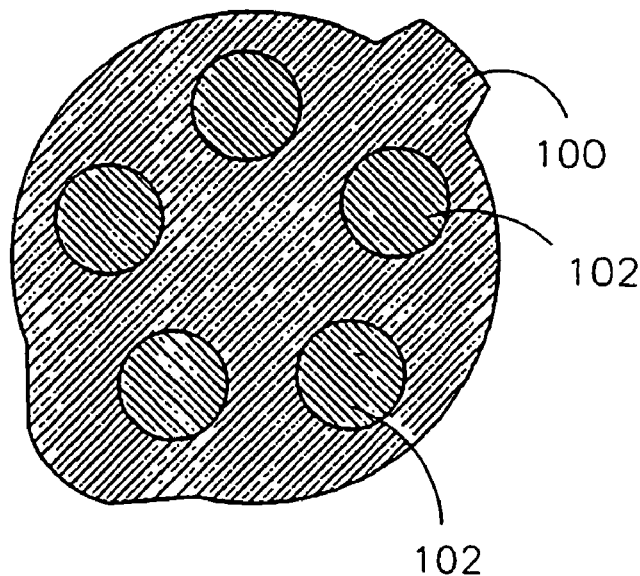
FIG. 13 is a simplified sectional illustration of an artificial femoral head, constructed and operative in accordance with still another preferred embodiment of the present invention, and wherein the femoral head comprises a plurality of portions, each portion not necessarily having the same mechanical or physical properties.

Reference is now made to FIG. 13 which illustrates an artificial femoral head 100, constructed and operative in accordance with still another preferred embodiment of the present invention. Femoral head 100 comprises a plurality of portions 102, each portion 102 not necessarily having the same mechanical or physical properties. Portions 102 may be used to enhance, to optimize or to customize the shock absorbing and damping characteristics of femoral head 100.

Figure 14A:
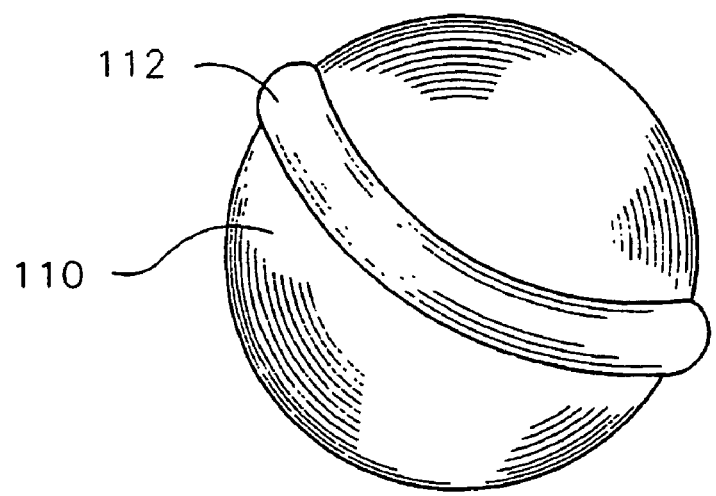
FIG. 14A is a simplified sectional illustration of an artificial femoral head, constructed and operative in accordance with another preferred embodiment of the present, invention, and wherein the femoral head comprises a protruding delimiting bumper.

Reference is now made to FIG. 14A which illustrates an artificial femoral head 110, constructed and operative in accordance with another preferred embodiment of the present invention. Femoral head 110 comprises a protruding delimiting bumper 112 instead of a delimiting rail.

Figure 14B:
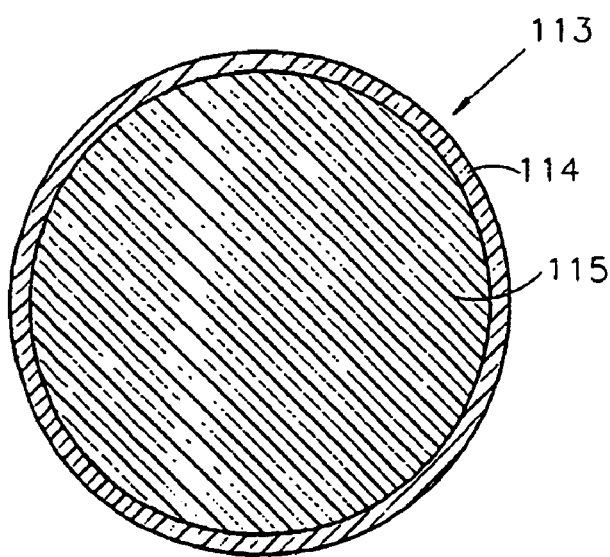
FIG. 14B is a simplified sectional illustration of an artificial femoral head, constructed and operative in accordance with yet another preferred embodiment of the present invention, and wherein the femoral head comprises a thin, resilient outer shell and a resilient core.

Reference is now made to FIG. 14B which illustrates an artificial femoral head 113, constructed and operative in accordance with yet another preferred embodiment of the present invention. Femoral head 113 comprises a thin, resilient outer shell 114 and a resilient core 115. Shell 114 may be constructed of DYNEEMA high performance polyethylene fibers, commercially available from DSM. Netherlands. DYNEEMA, particularly in the form of a woven fabric, provides a combination of high strength with excellent shock absorbing and damping characteristics, as well as being biocompatible. Core 115 may also be made of DYNEEMA with properties engineered to meet requirements such as strength or resilience, for example, and may be impregnated with other materials, such as a resin.

Figure 15:
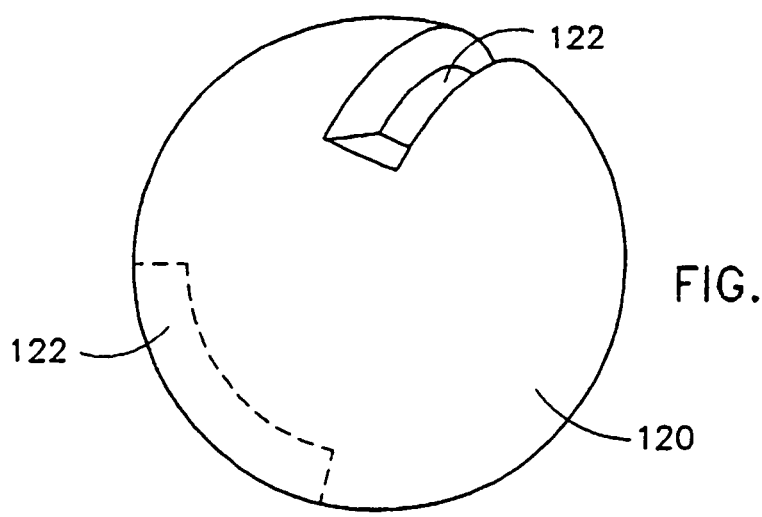
FIG. 15 is a simplified pictorial illustration of an artificial femoral head, constructed and operative in accordance with a preferred embodiment of the present invention, and including delimiting grooves.

Reference is now made to FIG. 15 which illustrates an artificial femoral head 120, constructed and operative in accordance with a preferred embodiment of the present invention. Femoral head 120 includes delimiting grooves 122 which articulate with corresponding rails (not shown) in an artificial acetabulum and an artificial socket (not shown).

Figure 16:
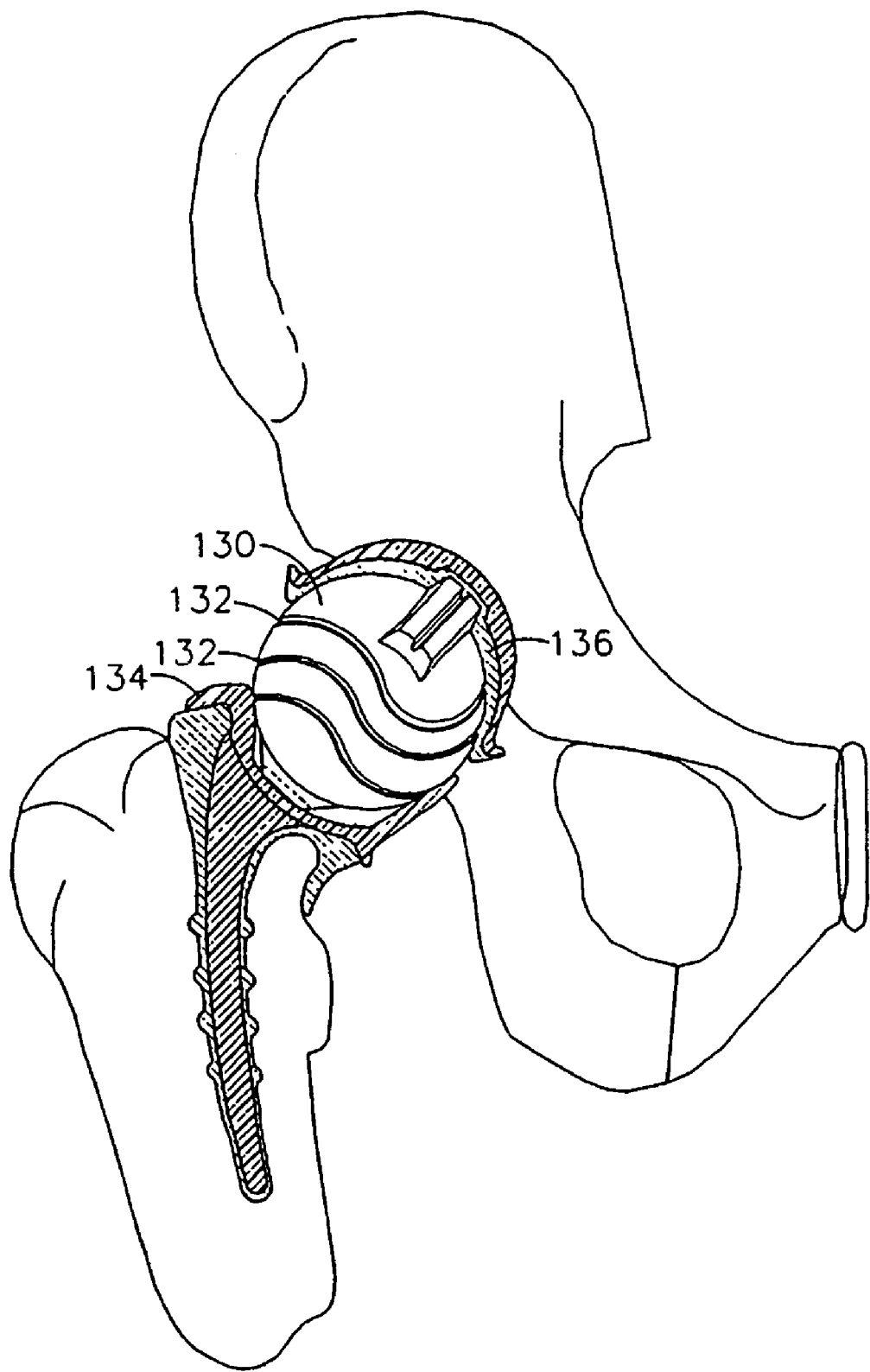
FIG. 16 is a simplified sectional illustration of an artificial femoral head, constructed and operative in accordance with another preferred embodiment of the present invention, and wherein the femoral head has fluid passageways.

Reference is now made to FIG. 16 which illustrates an artificial femoral head 130, constructed and operative in accordance with another preferred embodiment of the present invention. Femoral head 130 has fluid passageways 132 which allow flow therethrough of a fluid, preferably synovial fluid, the natural lubrication fluid of the human body. Fluid passageways 132 may be configured in a variety of orientations, configurations and sizes. Alternatively or additionally, passageways 132 may be provided in an artificial femoral socket 134 or an artificial acetabulum 136.

Fluid flowing in fluid passageways 132 may help lubricate femoral head 130. The presence of fluid in fluid passageways 132 may also enhance the shock absorbing and damping characteristics of femoral head 130.

As mentioned above, the ligaments connecting the femur and the innominate bone may be removed in the prior art, before placement of a hip joint prosthesis This is unfortunate because these ligaments are amongst the strongest ligaments in the body. These ligaments strengthen the joint and help prevent dislocation. Preserving some or all of the ligaments is therefore desirable.

Figure 17:
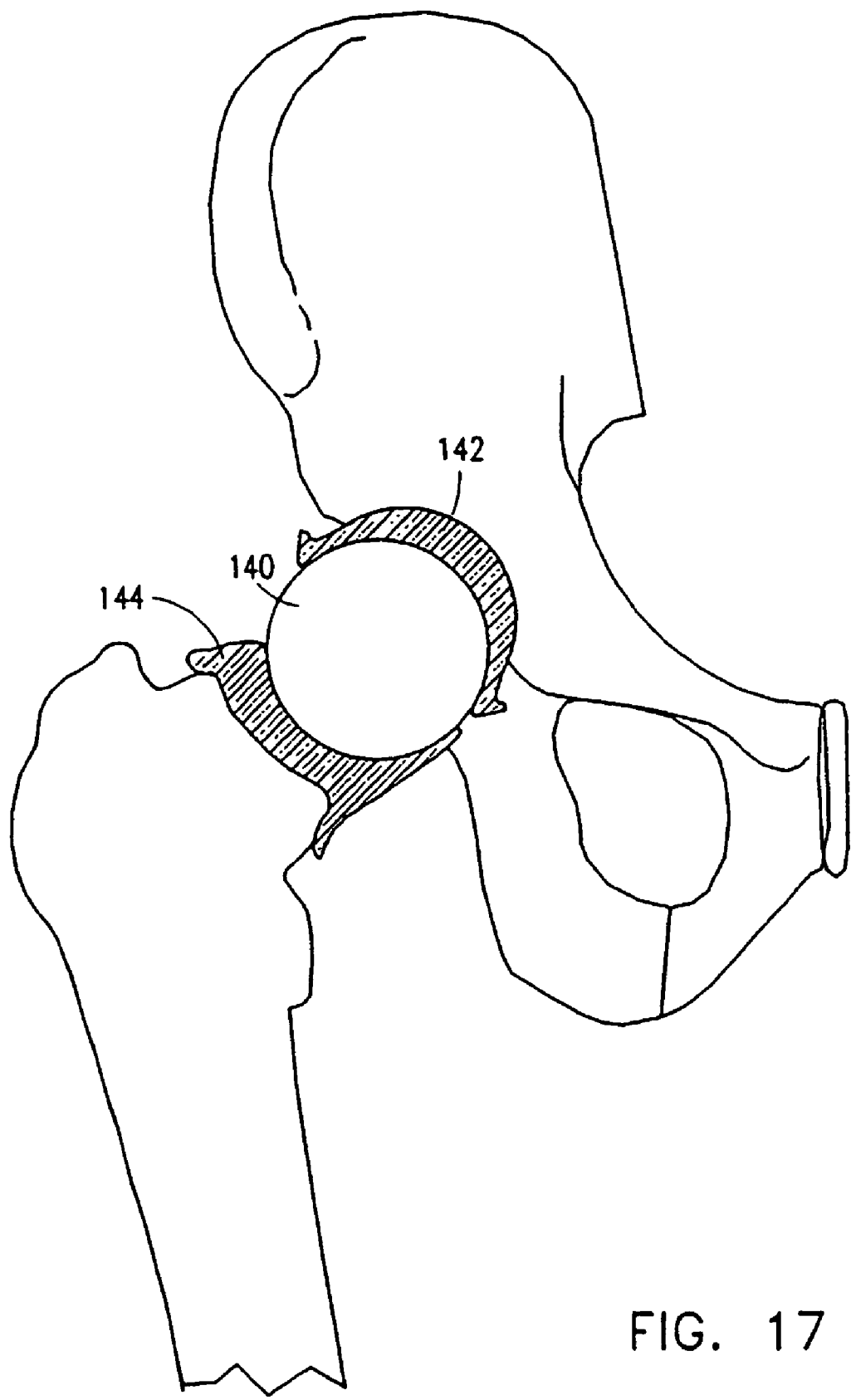
FIG. 17 is a simplified sectional illustration of an artificial femoral head, constructed and operative in accordance with yet another preferred embodiment of the present invention.

Reference is now made to FIG. 17 which illustrates an artificial femoral head 140, constructed and operative in accordance with yet another preferred embodiment of the present invention. Artificial femoral head 140 is preferably relatively small in size, thereby helping to reduce the need for tampering with some of the hip joint ligaments. In this embodiment, femoral head 140 articulates with an artificial acetabulum 142 and an artificial socket 144. Socket 144 may be attached directly to the femur without a stem, such as by bonding or via a crown (not shown) similar to the crown-shaped portion 20B described hereinabove with reference to FIGS. 2 and 3.

By eliminating the stem, the need for tampering with or drilling into the femur may also be eliminated. There may be no need to remove the entire natural femoral head, but rather a portion thereof may be preserved. Preserving part of the femur may simplify the surgical operation and may preserve most of the strength of the bone.

The need for tampering with some of the ligaments may also be reduced. Indeed, the intact ligaments themselves act together with the prosthesis of FIG. 17, because they tend to keep femoral head 140 properly installed. In addition, the embodiment of FIG. 17 may be more easily and quickly implanted than prostheses having stems.

Other embodiments of the present invention which address the problem of preserving the hip joint ligaments are described hereinbelow with respect to FIGS. 19A-21.

Reference is now made to FIGS. 18A and 18B which illustrate an artificial femoral head 150, constructed and operative in accordance with another preferred embodiment of the present invention. Femoral head 150 comprises a plurality of alternating adjacent portions 152 and 154 of substantially rigid and substantially resilient materials respectively. The rigid material is preferably a composite material and the resilient material is preferably polyurethane. In accordance with a preferred embodiment of the present invention, femoral head 150 is attached to an artificial acetabulum 156.

The material composition and the geometry of the portions 152 and 154 may be optimized to provide the desired rigidity and resiliency. In this manner, femoral head 150 may be constructed as a non-linear spring with multiple spring constants.

Femoral head 150 may have different rigidity and resiliency for forward-backward motion as opposed to lateral motion. For example, as seen in FIG. 18B, adjacent portions 152 and 154 are generally omega-shaped. Such a shape permits relatively easy swinging of the femur forwards and backwards with respect to the body, while at the same time constraining the swinging range to prevent overtravel of the femur. The resiliency of femoral head 150 damps the motion of the femur at the limits of its swing. The omega shape is stiffer in the lateral direction, thus limiting lateral motion of the femur with respect to the body. It is appreciated that femoral head 150 may be alternatively constructed to allow greater freedom of motion laterally than forwards and backwards.

Reference is now made to FIGS. 18C and 18D which show femoral heads 160 and 162 respectively, with adjacent layers 161 and 163 of substantially rigid and substantially resilient materials, respectively, constructed and operative in accordance with an alternative preferred embodiment of the present invention. As shown in FIGS. 18E and 18F, femoral heads 160 and 162 may be provided with apertures 164 and 166 respectively, which may, for example, provide a passageway for synovial fluid, nerves, blood vessels, ligaments, tissues, elongated force transmitting members or prosthetic controls. Fluid in apertures 164 and 166 may enhance the damping of femoral heads 160 and 162 respectively.

It is appreciated that the embodiments of FIGS. 18A-18F may be used as hinge or joint elements in other applications where it is desired to provide different rigidity or resiliency in different directions of motion.

Reference is now made to FIG. 18G which illustrates an, artificial acetabulum 400, constructed and operative in accordance with a preferred embodiment of the present invention.

Artificial acetabulum 400 preferably includes an interface 402 made of a resilient, cartilage-like material, and preferably has a generally triangular cutout 404. Acetabulum 400 preferably also includes an outer ridge 406 that "snap-fits" into the natural acetabulum socket, thereby substantially fixing artificial acetabulum 400 in the natural socket. The natural acetabulum may have to be drilled, cut or otherwise machined to ensure a proper snap fit so that acetabulum 400 is rigidly held in place. Ridge 406 may be continuous or may be formed of discrete portions that protrude into the natural acetabulum recesses. As seen in FIG. 18G, interface 402 may comprise a deformable, resilient flange 408 with expandable, accordion-like folds. Interface 402 may be one highly deformable piece, or may be slightly deformable, in which case it may fit into the natural acetabulum with a slight "click".

It is a particular feature of the present invention that ridge 406 provides shock absorption and positively locks interface 402 into a recess prepared in the natural socket, without any need for screws or adhesive. Interface 402 may comprise one or more layers. The large surface area of interface 402 provides a large load bearing and shock absorbing surface for a femoral head. Interface 402 may itself serve as an articulating surface for a femoral head, in which case the large surface area diminishes fretting and wearing of the articulating surfaces.

Reference is now made to FIGS. 18K and 18L which illustrate a cross section of interface 402 constructed in accordance with two preferred embodiments of the present invention. In FIG. 18K, it is seen that interface 402 preferably includes a plurality of protrusions 410 for locking interface 402 in recesses prepared in the natural socket. As seen in FIGS. 18G and 18L, interface 402 may also include an "umbilical" protrusion 412 that is configured to fit the natural or restructured "umbilical" recess of the natural acetabulum. This allows reduction of machining of the innominate bone and leaves a stronger bone.

Acetabulum 400 also preferably includes a locking piece 414 complementary shaped and sized to snugly fit into triangular cut-out 404. Interface 402 together with locking piece 414 may be used as the articulating portion of the prosthesis with the femur. Additionally, there is preferably provided an articulation portion 416 which snaps together with a recess 418 formed in interface 402. Articulation portion 416 may be made of metal, composite material, cartilage-like material, polyurethane or DYNEEMA. Articulation portion 416 may alternatively be attached to interface 402 by means of a bayonet type of connection or simply a press fit without clicking. Articulating portion 416 makes artificial acetabulum 400 into one stable integral assembly which is easily assembled in and removed from the innominate bone.

Reference is now made to FIGS. 18H, 18I and 18J which illustrate installing artificial acetabulum 400 into a natural acetabulum, in accordance with a preferred embodiment of the present invention. In FIG. 18H, an insertion tool 420 squeezes triangular cut-out 404 inwardly in the direction of arrows 422, to allow insertion of interface 402 into the natural socket. Upon release of insertion tool 420, cut-out 404 springs outwards much in the manner of a retaining ring, thereby pressing interface 402 firmly against and into the natural socket. Prongs of the insertion tool may be placed in prepared recesses or holes in interface 402.

In FIG. 18I, locking piece 414 is inserted into cut-out 404, thereby completing the shape of acetabulum 400 and firmly locking interface 402 into the natural socket when an articulating head or an additional articulating surface is assembled therewith. In FIG. 18J, articulation portion 416 is snapped together with interface 402, thereby making artificial acetabulum 400 into one integral assembly.

As mentioned above, the ligaments connecting the femur and the innominate bone may be removed in the prior art, before placement of a hip joint prosthesis. Methods for preserving the hip joint ligaments, or reinforcing or replacing them, are now described.

Reference is now made to FIGS. 19A-19C which illustrate a method of incision of ligaments, such as prior to insertion of a hip joint prosthesis, in accordance with a preferred embodiment of the present invention. A primary goal of the method of incision is to preserve the ligaments.

FIG. 19A illustrates a hip joint 170 prior to incision. As seen in FIG. 19B, a wave-like incision 172 may be made, such as with a laser device, in any or all of the ilio-femoral, pubo-femoral and ischio-femoral ligaments. As seen in FIG. 19C, the cut ligaments allow ample room for placement of a hip joint prosthesis (not shown).

As is known in the art, ligaments generally contract after incision, impairing mending of the ligament tissue. The wave-like shape of incision 172 permits slightly shifting the ligaments so that there is sufficient contact or overlap of the ligaments even after contraction, thereby helping to promote stitching and mending of the ligament tissue.

Reference is now made to FIG. 20 which illustrates a sleeve 180 for joining a femoral head 182 with the innominate bone, constructed and operative in accordance with a preferred embodiment of the present invention. Sleeve 180 is preferably made of a high strength woven fabric, such as DYNEEMA, polyethylene, nylon or polyurethane. Sleeve 180 preferably comprises filaments with a high elasticity modulus in the longitudinal direction of the ligaments, along an axis 184, and a circumferential stretching weave along an axis 186, generally perpendicular to axis 184, as seen in FIG. 20.

Sleeve 180 also preferably includes an anchoring band 188 for attaching sleeve 180 to the innominate bone. Anchoring band 188 may be attached to the innominate bone and sleeve 180 may be attached to the femoral head by any suitable means, such as bonding or with mechanical fasteners. Sleeve 180 may replace or assist the natural ligaments of the hip joint. Sleeve 180 may also help in mending of ligament tissue after surgery. All or portions of sleeve 180 may be constructed of a material, such as material used for dissolving sutures, which eventually dissolves after a predetermined period.

The present invention also provides a hip joint prosthesis which may substantially reduce the need for tampering with the hip joint ligaments. Reference is now made to FIG. 21 which illustrates an expandable artificial femoral head 190, constructed and operative in accordance with a preferred embodiment of the present invention. Femoral head 190 is preferably constructed of a resilient material, such as polyurethane. When expanded, femoral head 190 has substantially the same shape as femoral head 12, described hereinabove with reference to FIGS. 2 and 3.

In contrast to the prior art, femoral head 190, before expansion, may be inserted between the existing ligaments with minimum tampering thereof. Femoral head 190 may then be expanded to the desired shape. Femoral head 190 may be inflated by means of a fluid (not shown) introduced, for example, via a thin needle valve (not shown). Alternatively, femoral head 190 may be expanded by introducing therein components of an expandable foam (not shown), which expand inside femoral head 190.

The present invention will now be described in detail with respect to a prosthesis for a ginglymus, namely the knee joint. For a better understanding of a knee joint prosthesis, a basic description of the human knee joint is presented here with reference to FIG. 22, which illustrates the knee of the right leg.

The knee is a hinge comprising the internal and external condyles of the femur which articulate with the upper end of the tibia. The femoral condyles are separated by a deep fossa. The upper end of the tibia comprises two tuberosities, the external of which articulates with the head of the fibula.

The knee also comprises the trochlea of the femur (not shown in FIG. 22) which is located forward and upward of the condyles. The patella slides along the trochlea. The patella is shown pulled down in FIG. 22 in order to show some of the ligaments and cartilage which connect the femur, tibia, fibula and patella. These ligaments and cartilage include, inter alia, the external lateral ligament which connects the external femoral condyle to the fibula, the internal lateral ligament which connects the internal femoral condyle to the tibia, the ligamentum patellae to which is attached the patella, and the transverse ligament and internal semilunar cartilage which are attached to the head of the tibia. The transverse ligament, internal semilunar cartilage and the anterior crucial ligament are attached to the spine (not shown in FIG. 22) of the tibia. The spine is a series of elevations on the head of the tibia opposite the fossa between the femoral condyles.

Reference is now made to FIGS. 23 and 24 which illustrate a knee prosthesis 200, constructed and operative in accordance with a preferred embodiment of the present invention. Knee prosthesis 200 comprises an upper or femoral portion 202 and a lower or tibial portion 204, as seen in FIGS. 23 and 24.

Referring additionally to FIG. 25, it is seen that femoral portion 202 preferably comprises two pads 206 upon which rest the internal and external condyles of the femur, as seen in FIG. 24, and a trochlear portion 208 which is intermediate the patella and the trochlea, as seen in FIG. 23. Pads 206 articulate with tibial portion 204. As seen in FIG. 25, femoral portion 202 also preferably has a socket 210, whose function is described hereinbelow with reference to tibial portion 204.

Referring additionally to FIG. 26, it is seen that tibial portion 204 includes an artificial spine 212 which extends into socket 210. It is appreciated that when the knee flexes, socket 210 restricts the movement of spine 212 therein. Socket 210 and/or spine 212 are preferably constructed of a shock absorbing or resilient material, such that the movement of spine 212 is cushioned at the limits of travel in socket 210.

As seen in FIG. 23, spine 212 may extend beyond socket 210 into the fossa of the femur. Tibial portion 204 also preferably has two depressions 214 with which pads 206 may articulate. Tibial portion 204 preferably includes a stem 216 for attachment to the tibia. Tibial portion 204 may have one or more hollow portions 218 to increase shock absorption, damping or resiliency.

As seen in FIG. 23, a tibial cushion 220 may be placed intermediate tibial portion 204 and the head of the tibia, tibial cushion 220 preferably being constructed of a material compatible with human tissue, such as polyurethane. In accordance with a preferred embodiment of the present invention, femoral portion 202 may be constructed of a substantially rigid material, such as a composite material, and tibial portion 204 may be constructed of a substantially resilient material, such as polyurethane.

In accordance with another preferred embodiment of the present invention, femoral portion 202 may be constructed of a substantially resilient material and tibial portion 204 may be constructed of a substantially rigid material.

In accordance with yet another preferred embodiment of the present invention, femoral portion 202 may be constructed of a substantially resilient material and tibial portion 204 may be constructed of a substantially resilient material.

It is appreciated that knee prosthesis 200 is operative to absorb static and dynamic shocks.

It is a particular feature of the present invention that the resiliency of either femoral portion 202 or tibial portion 204 allows the configuration of the contact surfaces between portions 202 and 204 to change according to physical factors, such as load or motion. For example, when bearing loads directed downwards on the tibia, the contact area between portions 202 and 204 becomes relatively large, thereby increasing stability and decreasing pressure on the tibia. When the knee flexes, the contact area is relatively small, which facilitates motion of the tibia with respect to the femur. Femoral portion 202 and tibial portion 204 have different radii of curvature when not exposed to forces. The radii of curvature approach equality when bearing forces directed downwards on the tibia.

Reference is now made to FIGS. 27 and 28 which illustrate a knee prosthesis 230, constructed and operative in accordance with another preferred embodiment of the present invention. Knee prosthesis 230 comprises an upper or femoral portion 232 and a lower or tibial portion 234, as seen in FIGS. 27 and 28. Tibial portion 234 is substantially identical to tibial portion 204 described hereinabove with reference to FIGS. 23, 24 and 26.

Femoral portion 232 preferably comprises two pads 236 upon which rest the internal and external condyles of the femur, as seen in FIG. 28, and a trochlear portion 238 which is intermediate the patella and the trochlea, as seen in FIG. 27. Pads 236 articulate with tibial portion 234. Pads 236 preferably have one or more hollow portions 240, and may have one or more fluid passageways 242, for permitting flow therethrough of synovial fluid, thereby providing lubrication and enhancing the shock absorbing and damping characteristics of knee prosthesis 230.

Femoral portion 232 articulates with tibial portion 234 of knee prosthesis 230 by sliding along the generally concave surface of tibial portion 234. Reference is now made to FIGS. 29 and 30 which illustrate a knee prosthesis 250, constructed and operative in accordance with another preferred embodiment of the present invention. Knee prosthesis 250 comprises an upper or femoral portion 252 and a lower or tibial portion 254, as seen in FIGS. 29 and 30. Femoral portion 252 is preferably generally convex and articulates with tibial portion 254 by rolling along the generally convex surface of tibial portion 254.

As described hereinabove with reference to FIG. 23, the resiliency of either femoral portion 252 or tibial portion 254 allows the configuration of the contact, surfaces between portions 252 and 254 to change according to physical factors, such as load or motion.

Reference is now made to FIGS. 31 and 32 which illustrate a knee prosthesis 260, constructed and operative in accordance with another preferred embodiment of the present invention. Knee prosthesis 260 comprises an upper or femoral portion 262 which articulates with a lower or tibial portion 264 by means of one or more roller elements 266, as seen in FIGS. 31 and 32.

Portions 262 and 264 may be substantially rigid and roller elements 266 may be substantially resilient. Conversely, portions 262 and 264 may be substantially resilient and roller elements 266 may be substantially rigid.

Roller elements 266 may permit articulation of femoral portion 262 with tibial portion 264 by means of rolling, sliding, a combination of rolling and sliding, or rolling combined with a deformation of one or more of roller elements 266. Roller elements 266 may be formed in any shape which provides such rolling and sliding, such as being generally cylindrical in shape. An alternative shape is shown in FIG. 33.

At least one fluid passageway 268 may be provided in each roller element 266 for passage therethrough of a fluid, such as synovial fluid, thereby providing lubrication and enhancing the shock absorbing and damping characteristics of knee joint prosthesis 260.

Alternatively or additionally, each roller element 266 may have at least one hollow portion. Alternatively or additionally, each roller element 266 may comprise a plurality of portions, each portion not necessarily having the same mechanical or physical properties. These portions may be used to enhance, to optimize or to customize the shock absorbing and damping characteristics of the roller element 266.

Femoral portion 262 may be attached directly to the femoral condyles. Alternatively, as shown in FIG. 32, a femoral pad 270 may be placed intermediate femoral portion 262 and the femoral condyles. Femoral pad 270 may be constructed of a material with properties similar to human cartilage, such as polyurethane.

Reference is now made to FIG. 34 which illustrates a bone fastener 300 for fastening bone fractures, constructed and operative in accordance with a preferred embodiment of the present invention.

Bone fastener 300 preferably includes a core 302 and an outer layer 304. Outer layer 304 preferably includes one or more ridges 306, which, inter alia, help distribute stresses and help fasten bone fastener 300 to a bone. Core 302 may be of solid or hollow construction. Bone fastener 300 may have any suitable cross sectional shape, such as circular or elliptical.

In accordance with a preferred embodiment of the present invention, core 302 is preferably constructed of a rigid material, for example, stainless steel or a structural plastic. Alternatively, the rigid material may be a composite material, such as graphite fibers, which may be constructed to have mechanical or physical properties, such as modulus of elasticity or coefficient of thermal expansion, equivalent to that of the local human bone.

Outer layer 304 is preferably made of a resilient material compatible with human tissue, such as polyurethane, which helps distribute stresses optimally, thereby stimulating regeneration of bone. In accordance with a preferred embodiment of the present invention, outer layer 304 is constructed of a material, such as polyurethane, which has one or more mechanical and/or physical properties substantially similar to human cartilage.

Reference is now made to FIG. 35 which illustrates a vertebra replacement 310, constructed and operative in accordance with a preferred embodiment of the present invention.

Vertebra replacement 310 preferably includes at least one inner member 312, at least one intermediate member 314 and at least one outer member 316. Inner member 312 is preferably constructed of a substantially resilient material and may have one or more hollow portions 318. Alternatively, portions 318 may be filled with a fluid, such as synovial fluid. Additionally or alternatively, a fluid passageway (not shown) may be provided for fluid flow therethrough, thereby providing lubrication and enhancing the shock absorbing and damping characteristics of vertebra replacement 310.

Intermediate portion 314 may be less flexible than inner member 312, and is preferably constructed of a rigid material, for example, stainless steel or a structural plastic. Alternatively, the rigid material may be a composite material, such as graphite fibers, which may be constructed to have mechanical or physical properties, such as modulus of elasticity or coefficient of thermal expansion, equivalent to that of the local human bone.

Outer members 314 are preferably made of a resilient material compatible with human tissue, such as polyurethane, which helps distribute stresses optimally. In accordance with a preferred embodiment of the present invention, outer members 314 may be constructed of a material, such as polyurethane, which has one or more mechanical and/or physical properties substantially similar to human cartilage.

In accordance with a preferred embodiment of the present invention, geometrical data may be provided, such as by computerized tomography, and be used to prepare and select an optimal prosthesis or bone fastener prior to surgery. Data input, such as from the results of computerized tomography, may be used to match the geometry of the prosthesis or bone fastener to the needs of the patient. Either the prosthesis or the bone, or both, may be shaped, such as by computerized machining, using the geometrical data obtained.

Alternatively, the geometry of a preformed, standard prosthesis may be used to reshape the bone to match the prosthesis. Alternatively, the geometrical data used to reshape the bone may be used generally to form the prosthesis in real time.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited to what has been particularly shown and described hereinabove. Rather, the scope of the present invention is defined only by the claims that follow:

What is claimed is:

1. A tibial component for positioning in the knee joint, the component comprising:
a body formed of a resilient polyurethane having a non-linear stress-strain relationship, the lower portion of the body defining a lower surface having a central convex portion for abuttingly engaging the head of the tibia without penetrating the head of tibia, the upper portion of the body defining an upper contact surface having at least one concave depression with a first radius of curvature, an outside portion of the body defining a maximum outside height between the lower surface and the upper surface, the upper contact surface configured for engagement with a femoral portion having a convex outer surface having a second radius of curvature, the first and second radii of curvature being different in a first bearing configuration when not exposed to loading forces to define a first contact area between the depression and the convex surface, the first contact surface being resiliently deformable to a second bearing configuration in response to bearing forces directed downward on the depression to thereby define a second contact area between the depression and the convex outer surface, the second contact area being larger than the first contact area and the first radius of curvature substantially matching the second radius of curvature; and
a spine formed on said body, said spine extending upwardly toward the femur beyond the upper contact surface, the body and the spine defining an inside height, the inside height being substantially greater than the maximum outside height such that the upwardly extending spine is configured for at least partial engagement in the fossa between the femoral condyles to restrict movement,
wherein the resiliency of the body allows the contact surface area configuration to change during use according to physical loading factors.

2. The device of claim 1, wherein the spine has an anterior portion with an anterior height, a posterior portion with a posterior height and a central portion between the anterior and the posterior portions, wherein the central portion has a maximum height that is greater than the anterior height and the posterior height.

3. The device of claim 1, wherein the body has mechanical and physical properties substantially similar to human cartilage.

4. The device of claim 3, wherein the body has at least one of strength and elasticity generally similar to human cartilage.

5. The device of claim 1, wherein the polyurethane includes one or more reinforcing fibers.

6. The device of claim 5, wherein the fibers are oriented to permit the body to yield to increase the second contact surface upon the application of a force downward onto the tibia and substantially return to its original shape after such force is removed.

7. The device of claim 1, wherein the body includes a second concave depression, the concave depressions separated by the central spine.

8. The tibial component of claim 1, wherein the body portion comprises a plurality of hollow portions between the upper portion and the lower portion.

9. The tibial component of claim 8, wherein the plurality of hollow portions are positioned at an interior portion of the body portion spaced from the upper contact surface and the lower surface.

10. A knee prosthesis comprising:
a femoral component configured for secure engagement with a lower portion of a femur without penetrating the femur, the femoral component comprising:
a first portion for mating with an internal condyle of the femur;
a second portion for mating with an external condyle of the femur;
a central portion positioned between the first and second portions, the central portion of the femoral component having an upper surface portion, an opposing lower surface portion, and a socket extending through the central portion between the upper and lower surface portions; and
a third portion for positioning between a patella and a trochlea; and
a tibial component configured for secure engagement with an upper portion of a tibia without penetrating the tibia and configured for moving engagement with the femoral component, the tibial component comprising:
a lower portion for engaging with the upper portion of the tibia;
an upper portion comprising a projection for moving engagement with the socket of the femoral component, the projection extending up through the socket from the lower surface portion such that an upper portion of the projection extends beyond the upper surface portion of the central portion of the femoral component; and
a central portion extending between the upper and lower portions of the tibial component, the central portion of the tibial component including at least one hollow portion therein;
wherein the femoral component is constructed of a rigid material;
wherein the tibial component is constructed of a resilient material
wherein the femoral component includes a first articulating pad portion opposite the first portion for mating with an internal condyle of the femur and a second articulating pad portion opposite the second portion for mating with an external condyle of the femur; and wherein the upper portion of the tibial component further comprises a first depression for receiving the first articulating pad portion and a second depression for receiving the second articulating pad portion; and
wherein the first articulating pad portion comprises a first convex surface having a first radius of curvature and the first depression comprises a first concave surface, the first concave surface having a second radius of curvature different than the first radius of curvature in an unloaded state and having a third radius of curvature substantially similar to the first radius of curvature in a loaded state of the knee.

11. A knee prosthesis comprising:
a femoral component configured for secure engagement with a lower portion of a femur without penetrating the femur, the femoral component comprising:
a first portion for mating with an internal condyle of the femur;
a second portion for mating with an external condyle of the femur;
a central portion positioned between the first and second portions, the central portion of the femoral component having an upper surface portion, an opposing lower surface portion, and a socket extending through the central portion between the upper and lower surface portions; and
a third portion for positioning between a patella and a trochlea; and
a tibial component configured for secure engagement with an upper portion of a tibia without penetrating the tibia and configured for moving engagement with the femoral component, the tibial component comprising:
a lower portion for engaging with the upper portion of the tibia;
an upper portion comprising a projection for moving engagement with the socket of the femoral component, the projection extending up through the socket from the lower surface portion such that an upper portion of the projection extends beyond the upper surface portion of the central portion of the femoral component; and
a central portion extending between the upper and lower portions of the tibial component, the central portion of the tibial component including at least one hollow portion therein;
wherein the femoral component is constructed of a rigid material;
wherein the tibial component is constructed of a resilient material
wherein the femoral component includes a first articulating pad portion opposite the first portion for mating with an internal condyle of the femur and a second articulating pad portion opposite the second portion for mating with an external condyle of the femur; and wherein the upper portion of the tibial component further comprises a first depression for receiving the first articulating pad portion and a second depression for receiving the second articulating pad portion; and
wherein the resilient material of the tibial component allows a radius of curvature of the first and second depressions to change during use according to physical loading factors of the knee.

12. The knee prosthesis of claim 11, wherein the first and second depressions have a first radius of curvature in an unloaded state and a second radius of curvature in a loaded state of the knee, the second radius of curvature substantially matching a radius of curvature of the first and second articulation pad portions.

13. The knee prosthesis of claim 12, wherein the first and second depressions and the first and second articulation pad portions have a first contact area in the unloaded state and a second contact area in the loaded state, the second contact area being greater than the first contact area.

* * * * *